US007005511B2

(12) United States Patent
Tsien et al.

(10) Patent No.: US 7,005,511 B2
(45) Date of Patent: *Feb. 28, 2006

(54) FLUORESCENT PROTEIN VARIANTS AND METHODS FOR MAKING SAME

(75) Inventors: Roger Y. Tsien, LaJolla, CA (US); Robert E. Campbell, San Diego, CA (US); Geoffrey S. Baird, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 202 days.

This patent is subject to a terminal disclaimer.

(21) Appl. No.: 10/209,208

(22) Filed: Jul. 29, 2002

(65) Prior Publication Data
US 2005/0244921 A1 Nov. 3, 2005

Related U.S. Application Data

(63) Continuation-in-part of application No. 10/121,258, filed on Apr. 10, 2002, which is a continuation-in-part of application No. 09/866,538, filed on May 24, 2001, now Pat. No. 6,852,849, which is a continuation-in-part of application No. 09/794,308, filed on Feb. 26, 2001.

(51) Int. Cl.
 *C07H 21/04* (2006.01)
(52) U.S. Cl. .................. 536/23.1; 435/320.1; 435/69.1; 435/366; 435/9.6; 435/69.7; 530/350
(58) Field of Classification Search ............... 530/23.1, 530/350; 435/320.1, 69.1, 366, 9.6, 69.7; 536/23.1
See application file for complete search history.

(56) References Cited

U.S. PATENT DOCUMENTS 5,625,048 A    4/1997  Tsien et al.

FOREIGN PATENT DOCUMENTS

| WO | WO 96/23810    | 8/1996 |
| WO | WO 00/34318 A  | 6/2000 |
| WO | WO 00/34326    | 6/2000 |
| WO | WO 00/34526    | 6/2000 |
| WO | WO 01/62919    | 8/2001 |
| WO | WO 01/96373    | 12/2001 |
| WO | WO 02/068605 A2 | 9/2002 |

OTHER PUBLICATIONS

Bevis, B. J. et al. (2002) Rapidly maturing variants of the Discosoma red fluorescent protein (DsRed). Nat. Biotechnol. vol. 20,pp. 83-87.*
Yanushevich, Y. G. et al. (2002) strategy for the generation of non-aggregating mutants of Anthozoa fluorescent proteins. FEBS Lett. vol. 511, pp. 11-14.*
Terskikh, A. V. et al. (Mar. 2002) Analysis of DsRed Mutants. Space around the fluorophore accelerates fluorescence development. J. Biol. Chem. vol. 277, pp. 7633-7636.*
Wall, M. A. (2000) The structural basis for red fluorescence in the tetrameric GFP homolog DsRed. Nat. Struct. Biol. vol. 7, pp. 1133-1138.*
Attachment 1: ClonTech (Jan. 2002) DsRed2 Subcellular Localization Vectors, "New products", pp. 1-2.*
Attachment 2: pQE-30 and pQE-31 (2003) from Qiagen.*
Matz, M. V. et al. (1999) Fluorescent proteins from nonbioluminescent Anthozoa species. Nat. Biotechnol. vol. 17, pp. 969-973.*
Campbell et al. "A monomeric red fluorescent protein" *PNAS* 99(12):7877-7882 (2002).
Tsien, R. "Rosy dawn for fluorescent proteins" *Nature Biotechnology* 17: 956-957 (1999) and Nucleotide search results, Accession No. AF168419.
Yang et al., "The Molecular Structure of Green Fluorescent Protein." Nature Biotechnology 14:1246-1251 (1996).
Baird, G.S., "Designing Fluorescent Biosensors by Exploiting Structure-Function Relationships in Fluorescent Proteins," *Ph. D. Thesis*, Biomedical Sciences, University of California, San Diego (2001).
Baird et al., "Circular Permutation and Receptor Insertion within Green Fluorescent Proteins" *Proc. Natl. Acad. Sci. USA* 96:11241-11246 (1999).
Baird et al., "Biochemistry, Mutagenesis, and Oligomerization of DsRed, a Red Fluorescent Protein from Coral" *Proc. Natl. Acad. Sci., USA*, 97:11984-11989, 2000.
BD Biosciences/Clontech, Product literature, "Living Colors DsRed C-Terminal Fusion Vector" *CLONTECHniques*, p. 22, (Jan. 2000).
BD Biosciences/Clontech, Product literature, "Living Colors DsRed Express" *CLONTECHniques*, pp. 16-17, (Jul. 2002).
BD Biosciences/Clontech, Product literature, "Living Colors HcRed" *CLONTECHniques*, (Apr. 2002).
BD Biosciences/Clontech, Product literature, "Living Colors Red Fluorescent Protein" *CLONTECHniques*, vol. XIV, No. 4 pp. 2-6, (Oct. 1999).
BD Biosciences/Clontech, Product literature, "Mercury DsRed I Signaling Probes" *CLONTECHniques*, pp. 22 & 23, (Apr. 2000).

(Continued)

*Primary Examiner*—Jon Weber
*Assistant Examiner*—Samuel W. Liu
(74) *Attorney, Agent, or Firm*—Townsend and Townsend and Crew LLP

(57) ABSTRACT

The present invention relates generally to variant fluorescent proteins, and more specifically to monomeric and dimeric forms of Anthozoan fluorescent proteins. In one aspect, the present invention provides variants of fluorescent proteins, where the variants have a reduced propensity to tetramerize, and form dimeric or monomeric structures. The invention also relates to methods of making and using such fluorescent protein monomers and dimers.

44 Claims, 39 Drawing Sheets

OTHER PUBLICATIONS

Bevis and Glick, "Rapidly Maturing Variants of the Discosoma Red Fluorescent Protein", *Nat. Biotechnol.*, 20:83-87 [2002].

Campbell et al., "A Monomeric Red Fluorescent Protein" *Proc. Natl. Acad. Sci. USA*, 99:7877-7882 [Jun. 11, 2002].

Gross et al., "The Structure of the Chromophore within DSRed, a Red Fluorescent Protein from Coral" *Proc. Natl. Acad. Sci., USA*, 97:11990-11995, 2000.

Gurskaya et al., "GFP-like Chromoproteins as a Source of Far-Red Fluorescent Proteins", *FEBS Lett.*, 507:16-20 [2001].

Heim et al., "Improved Green Fluorescence" *Nature*. 373: 663-664, 1995.

Heim et al., "Wavelength Mutations and Posttranslational Autoxidation of Green Fluorescent Protein", *Proc. Natl. Acad. Sci. USA*, 91:12501-12504, 1994.

Labas et al., "Diversity and Evolution of the Green Fluorescent Protein Family" *Proc. Natl. Acad. Sci. USA*, 99:4256-4261 [2002].

Lauf et al., "Expression of Fluorescently Tagged Connexins: A Novel Approach to Rescue Function of Oligomeric DsRed-Tagged Proteins" *FEBS Lett.*, 498:11-15 [2001].

Lukyanov et al., "Natural Animal Coloration Can Be Determined by a Nonfluorescent Green Fluorescent Protein Homolog" *J. Biol. Chem.*, 275:25879-25882, 2000.

Matz et al., "Fluorescent Proteins from Nonbioluminescent Anthozoa Species", *Nature Biotechnology*, 17:969-973 (1999).

Miyawaki and Tsien, "Monitoring Protein Conformations and Interactions by Fluorescence Resonance Energy Transfer Between Mutants of Green Fluorescent Protein" *Methods Enzymol., Application of Chimeras in Cell Physiology*, 327:472-500 (2000).

Miyawaki et al., "Dynamic and Quantitative Ca2+ Measurements Using Improved Cameleons" *Proc. Natl. Acad. Sci., USA*, 96:2135-2140, 1999.

Prasher et al., "Summary Structure of the *Aequorea victoria* Green-Fluorescent Protein" *Gene*, 111:229-233 (1992).

Remington, "Negotiating the Speed Bumps to Fluorescence" *Nat. Biotechnol.*, 20:28-29 [2002].

Roth, "Purification & Protease Susceptibility of the Green-Fluorescent Protein of *Aequorea* with a Note on Hlistaura" Thesis from the Graduate Program in Biochemistry from Rutgers, the State University of New Jersey (1985).

Terskikh et al., "Analysis of DsRed Mutants" *J. Biol. Chem.*, 277:7633-7636 [2002].

Verkhusha et al., "Kinetic Analysis of Maturation & Denaturation of DsRed, a Coral-Derived Red Fluorescent Protein", *Biochemistry*, vol. 66, No. 12, 1342-1351 [2001].

Wall et al., "The Structural Basis for Red Fluorescence in the Tetrameric GFP Homolog DsRed" *Nature Struct. Biol.*, 7:1133-1138 [2000].

Wiehler et al., "Mutants of Discosoma Red Fluorescent Protein with a GFP-like Chromophore" *FEBS Letters* 487: 384-389 (2001).

Yanushevich et al., "A Strategy for the Generation of Non-aggregating Mutants of *Anthozoa* Fluorescent Proteins" *FEBS Letters.*, 511:11-14 [2002].

Yarbrough et al., "Refined Crystal Structure of DsRed, a Red Fluorescent Protein from Coral, at 2.0—A Resolution" *Proc. Natl. Acad. Sci. USA*. 98:462-467 [2001].

Magierowska, M., et al., "Highly Uneven Distribution of Tenofovir-Selected Simian Immunodeficiency Virus in Different Anatomical Sites of Rhesus Macaques," *Journal of Virology*—78(5):2434-2444 (2004).

Ormö, Mats, et al., "Crystal Structure of the *Aequorea victoria* Green Fluorescent Protein", Science, vol. 273, pp 1392-1395, Sep. 6, 1996.

Gavin, Paul et al, *An Approach for Reducing Unwanted Oligomerisation of DsRed Fusion Proteins*, Biochemical and Biophysical Research Communications, 2002, pp. 707-713, 298.

* cited by examiner

FIG. 10A

| Library* | Template | Method† | Targeted positions | Top clone‡ | Name |
|---|---|---|---|---|---|
| D1 | T1§ + I125R | MOE | I161/K163/S179/S197 | T1 + S117C_rev/I125R/ K163Q/S179T/S197T | dimer1 |
| D2 | dimer1 | EPM | n/a | dimer1 + V71A/S131P | dimer1.02 |
| D3 | dimer1.02 | MOE | K70/S197/T217 | dimer1.02 + K70R/ F118L/T217S | dimer1.56 |
| D4 | dimer1.56 | MOE | C117/F118/F124/ V127T | dimer1.56 + R70K_rev/ C117T/F118L/V127T | dimer2 |
| D5 | T1 + I125R | MOE | I161/K163/S179/ S197/H222G/F224G | a. T1 + S117C_rev/F124L/ I125R/K163Q/S179T/ S197T/H222G/F224G | a.HF2Ga |
|  |  |  |  | b. As in a with K163H | b.HF2Gb |
| M1 | dimer1 | MOE | E144/A145/S146/ I161/H162/K163/ A164/H222G/F224G | dimer1 + E144A/ A145R/H162K/K163M/ A164R/ H222G/F224G | mRFP0.1 |
| M2 | mRFP0.1 | EPM | n/a | mRFP0.1 + Y192C | mRFP0.2 |
| M3 | dimer1.56 & HF2Ga & HF2Gb & mRFP0.2 | MOE | C117/F124/V127T/ S131/H162/K163/ A164/Y192A/Y194A/ H222G/F224G | mRFP0.2 + K70R/ C117E/ F124L/V127T/ A144E_rev/ R145A_rev/ Y192A/Y194A/T217S | mRFP0.3 |

*Libraries are labeled either 'M' or 'D' if they are composed of monomers or dimers respectively. †In each round libraries were constructed by either the multiple overlap extension (MOE) or error-prone PCR mutagenesis (EPM). ‡Unless otherwise indicated, the top clone contains all mutations present in the starting template. All mutations are relative to wild type DsRed except reversions, which are identified with the subscript 'rev'. § The T1 construct used in this work differs from the original T1 construct(7) by the absence of the P(-4)L mutation and the inserted valine residue (V1a) which is present in all constructs except mRFP1.

| Library* | Template | Method† | Targeted positions | Top clone‡ | Name |
|---|---|---|---|---|---|
| M4 | mRFP0.3 | MOE | K70/V71/K83/ Y192/Y194/V195/ S197/ T217/L223/ L225 | a. mRFP0.3 + K83I/ L223E/L225A<br>b. mRFP0.3 + R70K rev/ V71A/ K83L/Y194K/ V195T/S197I/T217A/ H222C/ L223T/L225A | a. mRFP0.4a<br>b. mRFP0.4b |
| M5 | mRFP0.4a & mRFP0.4b | EPM | n/a | a. mRFP0.4a + F177S<br>b. mRFP0.4b + L150M/ V156A | a. mRFP0.5a<br>b. mRFP0.5b |
| M6 | mRFP0.5a & mRFP0.5b | MOE | L174/ V175/F177/ F180 | mRFP0.5b + L174D/ V175A/F177V/I180T | mRFP0.6 |
| M7 | mRFP0.6 | MOE | V1a del/A145/R149/L150/ R153/V156/H222S | mRFP0.6 + V1a del/ R153E/H222S | mRFP1 |

*Libraries are labeled either 'M' or 'D' if they are composed of monomers or dimers respectively. †In each round libraries were constructed by either multiple overlap extension (MOE) or error-prone PCR mutagenesis (EPM). ‡Unless otherwise indicated, the top clone contains all mutations present in the starting template. All mutations are relative to wild type DsRed except reversions, which are identified with the subscript 'rev'. § The T1 construct used in this work differs from the original T1 construct(7) by the absence of the P(-4)L mutation and the inserted valine residue (V1a) which is present in all constructs except mRFP1.

| Library | Primer pairs for fragment amplification | Positions | Codon * | Possible substitutions |
|---|---|---|---|---|
| D1 | 1. PRSET_BamH1_FW/I161X_K163X_RV<br>2. I161X_K163X_FW/S179X_RV<br>3. S179X_FW/S197X_A_RV<br>4. S197X_A_FW/PRSET_EcoR1_RV | I161<br>K163<br>S179<br>S197 | VYC<br>MWS<br>NCC<br>NCC | T/I/A/V/P/L<br>Q/H/L/K/N/M/I<br>A/S/T/P<br>A/S/T/P |
| D3 | 1. PRSET_BamH1_FW/S197X_B_RV<br>2. S197X_B_FW/T217X_RV<br>3. T217X_FW/PRSET_EcoR1_RV | K70†<br>S197<br>T217 | ARG<br>NNK<br>DYC | K/R<br>All 20 a.a.<br>A/T/S/V/I/F |
| D4 | 1. PRSET_BamH1_FW/C117X_V127T_RV<br>2. C117X_V127T_FW/PRSET_EcoR1_RV | C117<br>F118<br>F124<br>V127 | RVS<br>NTS<br>NTS<br>ACC | T/K/S/N/R/A/E/G/D<br>L/M/V/I/F<br>L/M/V/I/F<br>T |
| D5 | 1. PRSET_BamH1_FW/I161X_K163X_RV<br>2. I161X_K163X_FW/S179X_RV<br>3. S179X_FW/S197X_RV<br>4. S197X_FW/H222G_F224G_RV | I161<br>K163<br>S179<br>S197<br>H222<br>F224 | VYC<br>MWS<br>NCC<br>NCC<br>GGC<br>GGC | T/I/A/V/P/L<br>Q/H/L/K/N/M/I<br>A/S/T/P<br>A/S/T/P<br>G<br>G |

*The standard mixed base definitions are R = A/G, Y = C/T, M = A/C, K = G/T, S = C/G, W = A/T, H = A/C/T, B = C/G/T, V=A/C/G, D=A/G/T, N=A/C/G/T  Multiple templates were used to introduce these K70 substitutions.

FIG. 11B

| Library | Primer pairs for fragment amplification | Positions | Codon * | Possible substitutions |
|---|---|---|---|---|
| M1 | 1. PRSET_BamH1_FW/E144X_A164X_RV<br>2. E144X_A164X_FW/H222G_F224G_RV | E144<br>A145<br>S146<br>I161<br>H162<br>K163<br>A164<br>H222<br>F224 | VVS<br>VVS<br>ASC<br>NHC<br>ARG<br>NWS<br>ARG<br>GGC<br>GGC | G/R/A/P/T/E/Q/K/S/D/H/N<br>G/R/A/P/T/E/Q/K/S/D/H/N<br>S/T<br>N/D/H/Y/T/A/P/S/I/L/V/F<br>K/R<br>K/E/Q/M/V/L/N/D/H/Y/I/F<br>K/R<br>G<br>G |
| M3 | 1. PRSET_BamH1_FW/C117X_S131X_RV<br>2. C117X_S131X_FW/H162X_A164X_RV<br>3. H162X_A164X_FW/Y192A_Y194A_RV<br>4. Y192A_Y194A_FW/H222G_F224G_RV | C117<br>F124<br>V127<br>S131<br>H162<br>K163<br>A164<br>Y192<br>Y194<br>H222<br>F224 | RVS<br>NTS<br>ACC<br>YCC<br>ARG<br>MWS<br>ARG<br>GCC<br>GCC<br>GGC<br>GGC | T/K/S/N/R/A/E/G/D<br>L/M/V/I/F<br>T<br>S/P<br>K/R<br>Q/H/L/K/N/M/I<br>K/R<br>A<br>A<br>G<br>G |

*The standard mixed base definitions are R = A/G, Y = C/T, M = A/C, K = G/T, S = C/G, W = A/T, H = A/C/T, B = C/G/T, V=A/C/G, D=A/G/T, N=A/C/G/T Multiple templates were used to introduce these K70 substitutions.

FIG. 11C

| Library | Primer pairs for fragment amplification | Positions | Codon * | Possible substitutions |
|---|---|---|---|---|
| M4 | 1. PRSET_BamH1_FW/K70X_K83X_RV | K70 | ARG | K/R |
| | 2. K70X_K83X_FW/Y192X_S197X_RV | V71 | GYC | V/A |
| | 3. Y192X_S197X_FW/T217X_L225X_RV | K83 | WWK | N/K/I/M/Y/F/L |
| | | Y192 | RMS | E/D/A/K/N/T |
| | | Y194 | RMS | E/D/A/K/N/T |
| | | V195 | RYC | T/I/A/V |
| | | S197 | RYC | T/I/A/V |
| | | T217 | DCC | S/T/A |
| | | L223 | RMS | E/D/A/K/N/T |
| | | L225 | RMS | E/D/A/K/N/T |
| M6 | 1. PRSET_BamH1_FW/L174X_I180X_RV | L174 | VVC | A/D/G/H/N/P/R/S/T |
| | 2. L174X_I180X_FW/PRSET_EcoR1_RV | V175 | NYC | P/T/S/A/L/I/F/V |
| | | F177 | NYC | P/T/S/A/L/I/F/V |
| | | I180 | AYC | I/T |
| M7 | 1. PRSET_BamH1_FW/A145X_V156X_RV | V1a | deletion | deletion |
| | 2. A145X_V156X_FW/PRSET_EcoR1_RV | A145 | SCC | A/P |
| | then | R149 | CRS | Q/H/R/R |
| | 3. V1a_del_FW/H222S_REV | L150 | NTS | L/M/V/I/F |
| | | R153 | VAS | E/Q/D/H/K/N |
| | | V156 | RBC | V/A/T/I/S/G |
| | | H222 | TCC | S |

*The standard mixed base definitions are R = A/G, Y = C/T, M = A/C, K = G/T, S = C/G, W = A/T, H = A/C/T, B = C/G/T, V=A/C/G, D=A/G/T, N=A/C/G/T Multiple templates were used to introduce these K70 substitutions.

FIG. 12A

| Primer Name | Sequence | SEQ ID No. |
|---|---|---|
| Primers for General Use | | |
| PRSET_BamH1_FW | GTA CGA CGA TGA CGA TAA GGA TCC | 41 |
| PRSET_EcoR1_RV | GCA GCC GGA TCA AGC TTC GAA TTC | 42 |
| Primers Used to Construct Libraries for DsRed Dimer Evolution | | |
| N42X_V44X_FW | CGC CCC TAC GAG GGC CAC MWS ACC VYC AAG CTG AAG GTG ACC AAGG | 43 |
| N42X_V44X_RV | CCT TGG TCA CCT TCA GCT TCA GGT TGR BGG TSW KGT GGC CCT CGT AGG GGC G | 44 |
| K70X_V71X_FW | CAG TTC CAG TAC GGC TCC NNK NYC TAC GTG AAG CAC CCC GCC | 45 |
| K70X_V71X_RV | GGC GGG GTG CTT CAC GTA GRN MNN GGA GCC GTA CTG GAA CTG | 46 |
| C117X_V127T_FW | CAG GAC GGC RVS NTS ATC TAC AAG GTG AAG NTS CGC GGC ACC AAC TTC | 47 |
| C117X_V127T_RV | GAA GTT GGT GCC GCG SAN CTT GTA GAT SAN SBY GCC GTC CTG | 48 |
| I161X_K163X_FW | GGC GTG CTG AAG GGC GAG VYC CAC MWS GCC CTG AAG CTG AAG GACG | 49 |
| I161X_K163X_RV | CGT CCT TCA GCT TCA GGG CSW KGT GGR BCT CGC CCT TCA GCA CGC C | 50 |
| S179X_FW | GGT GGA GTT CAA GNC CAT CTA GNC CAT GGC CAA G | 51 |
| S179X_RV | CTT GGC CAT GTA GAT GGN CTT GAA CTC CAC C | 52 |
| S197X_A_FW | CTA CTA CTA CGT GGA CNC CAA GCT GGA CAT CAC C | 53 |
| S197X_A_RV | P-GGT GAT GTC CAG CTT GKN GTC CAC GTA GTA G | 54 |
| S197_B_FW | C TAC TAC TAC GTG GAC NNK AAG CTG GAC ATC ACC | 55 |
| S197_B_RV | GGT GAT GTC CAG CTT MNN GTC CAC GTA GTA G | 56 |
| T217X_FW | CAG TAC GAG CGC NCC GAG GGC CAC | 57 |
| T217X_RV | GTG GCG GCC CTC GGN GCG CTC GTA CTG | 58 |

The standard mixed base definitions are R = A/G, Y = C/T, M = A/C, K = G/T, S = C/G, W = A/T, H = A/C/T, B = C/G/T, V = A/C/G, D = A/G/T, N=A/C/G/T.

FIG. 12B

| Primer Name | Sequence | SEQ ID No. |
|---|---|---|
| Primers used for DsRed Monomer Evolution | | |
| K70X_K83X_FW | AAG CAC CCC GCC GAC ATC CCC GAC TAC WWK AAG CTG TCC | 59 |
| K70X_K83X_RV | GAT GTC GGC GGG GTG CTT CAC GTA GRC CYT GGA GCC GTA CTG | 60 |
| C117X_S131X_FW | GTG AAG NTS CGC GGC ACC AAC TTC CCC YCC GAC GCC | 61 |
| C117X_S131X_RV | GAA GTT GGT GCC GCG SAN CTT CAC CTT GTA GAT GAA SBY GCC GTC CTG | 62 |
| E144X_A164X_FW | CTG TAC CCC CGC GAC GGC GTG CTG AAG GGC GAG NHC ARG NWS ARG CTG AAG GAC GGC GGC | 63 |
| E144X_A164X_RV | CTT CAG CAC GCC GTC GCG GGG GTA CAG GCG CTC GGT GST SBB SBB CCA GCC CAT RGT CTT CTT CTG | 64 |
| A145X_V156X_FW | TCC ACC GAG CRS NTS TAC CCC VAS GAC GGC RBC CTG AAG GGC | 65 |
| A145X_V156X_RV | GCC GTC STB GGG GTA SAN SYG CTC GGT GGA GGS CTC CCA GCC | 66 |
| H162X_A164X_FW | CTG AAG GGC GAG ATC ARG MWS ARG CTG AAG GAC | 67 |
| H162X_A164X_RV | GTC CTT CAG CTT CYT SWK CYT GAT CTC GCC CTT CAG | 68 |
| L174X_180X_FW | GGC CAC TAC VVC NYC GAG NYC AAG ACC AYC TAC ATG GCC | 69 |
| L174X_180X_RV | GGC CAT GTA GRT GGT CTT GRN CTC GRN GBB GTA GTG GCC | 70 |
| Y192A_Y194A_FW | GTG CAG CTG CCC GGC GCC TAC GCC GTG GAC ACC AAG CTG | 71 |
| Y192A_Y194A_RV | CAG CTT GGT GTC CAC GGC GTA GGC GCC GGG CAG CTG CAC | 72 |
| Y192X_S197X_FW | GGC RMS TAC RMS RYC GAC RYC AAG CTG GAC ATC ACC | 73 |
| Y192X_S197X_RV | CTT GRY GTC GRY SKY GTA SKY GCC GGG CAG CTG CAC | 74 |
| T217X_L225X_RV | C GAA TTC TTA SKY GCC SKY GCC GTG GCC GCC CTC GGH GCG CTC | 75 |
| H222G_F224G_RV | P-GCT TCG AAT TCT TAC AGG CCC AGG CCG TGG CGG CCC TCG G | 76 |
| V1a_del_FW | AAG GAT CCG ATG GCC TCC TCC GAG GAC GTC | 77 |
| H222S_REV | TTC GAA TTC TTA GGC GCC GGT GGA GTG GTG GCG GCC | 78 |

The standard mixed base definitions are R = A/G, Y = C/T, M = A/C, K = G/T, S = C/G, W = A/T, H = A/C/T, B = C/G/T, V = A/C/G, D=A/G/T, N= A/C/G/T.

FIG. 13

| Construct/Injection | Number of Cells (and %) Showing Lucifer Yellow Passage | Did not pass lucifer yellow |
|---|---|---|
| Cx43-mRFP1 | 8 (100%) | 0 |
| Cx43-mRFP0.5a | 36 (100%) | 0 |
| Cx43-tdimer2(12)* | 13 (33.5%) | 27 |
| Cx43-dimer2 | 16 (35%) | 29 |
| Cx43-T1 | 1 (2.5%) | 38 |
| Injected untransfected cells | 0 (0%) | 22 |
| Injected transfected cell in contact with an untransfected cell. | 0 (0%) | 76 |

* Found one obvious gap junction with Cx43-tdimer2(12)

FIG. 14

| | Excitation maximum (nm) | Emission maximum (nm) | $\varepsilon$ (M$^{-1}$cm$^{-1}$) | Quantum Yield (QY) | QY of photobleach | pK$_a$ | t$_{0.5}$ for maturation at 37°C |
|---|---|---|---|---|---|---|---|
| DsRed* | 558 | 583 | 57 × 10$^3$ | 0.79 | 2.7 × 10$^{-7}$ | 4.7 | ~10 h |
| T1 | 555 | 584 | 35 × 10$^3$ | 0.51 | 2.1 × 10$^{-7}$ | 4.8 | <1 h |
| dimer2 | 552 | 579 | 60 × 10$^3$ | 0.69 | 2.5 × 10$^{-7}$ | 4.9 | ~2 h |
| tdimer2(12) | 552 | 579 | 120 × 10$^3$ | 0.68 | 2.0 × 10$^{-7}$ | 4.8 | ~2 h |
| mRFP1 | 584 | 607 | 44 × 10$^3$ | 0.25 | 2.9 × 10$^{-6}$ | 4.5 | <1 h |
| *Published values for the $\varepsilon$ and QY of photobleach of DsRed are highly variable, suggesting that these values depend critically on the conditions of the purification or handling. All values were determined in parallel on identically treated ||||||||

FIG. 15

| Mutation | Red Species Exc (nm) | Red Species Em (nm) | Green Species Exc (nm) | Green Species Em (nm) | Maturation Speed | Red/Green Ratio |
|---|---|---|---|---|---|---|
| None | 558 | 583 | 475 | 499 | ++ | 840 |
| K83R | 558 | 582 | 480 | 499 | -- | 0.05 |
| K83E | 550 | 584 | 474 | 497 | -- | 0.43 |
| K83N | 558 | 592 | 474 | 497 | - | 9.8 |
| K83P | 558 | 594 | 474 | 497 | - | 3.3 |
| K83F | 560 | 594 | 474 | 499 | -- | 0.29 |
| K83W | 562 | 594 | 478 | 501 | - | 0.44 |
| K83M | 564 | 602 | 474 | 499 | -- | 49 |
| Y120H | 562 | 600 | 478 | 499 | - | 0.4 |
| S197T | 558 | 584 | 478 | 499 | + | 53 |
| K70R | 562 | 585 | 480 | 503 | - | 13.8 |
| K70M | N/a | n/a | 480 | 499 | n/a | 0 |

FIG. 16  SEQ ID NO: 2 nucleotide sequence of the *Discosoma* wild-type red fluorescent protein open reading frame

```
atgaggtcttccaagaatgttatcaaggagttcatgaggttcatgaggttcgcatggaagga
acggtcaatgggcacgagtttgaaatagaaggcgaaggagaggggaggccatacgaaggc
cacaataccgtaaagcttaaggtaaccaaggggggaccttttgccatttgcttggatatt
ttgtcaccacaatttcagtatggaagcaaggtatatgtcaagcaccctgccgacatacca
gactataaaagctgtcatttcctgaaggattaaatgggaaaggtcatgaactttgaa
gacggtggcgtcgttactgtaacccagattccagtttgcaggatggctgtttcatctac
aaggtcaagttcattggcgtgaacttcctccgatgacctgttatgcaaaagaagaca
atgggctgggaagccagcagcgtctgagcgtgtatccctcgtgatgcgtgttgaaaggagag
attcataaggctctgaagctgaaagacggtggtcattacctagttgaattcaaaagtatt
tacatggcaaagaagccacaaggctaccaggtactactatgttgactccaaactggat
ataacaagccacaacgaagactatacaatcgttgagcagtatgaaagaaccgagggacgc
caccatctgttcctttaa
```

FIG. 17   SEQ ID NO: 1 amino acid sequence of the *Discosoma* wild-type red fluorescent protein

```
M R S S K N V I K E F M R F K V R M E G
T V N G H E F E I E G E G E G R P Y E G
H N T V K L K V T K G G P L P F A W D I
L S P Q F Q Y G S K V Y V K H P A D I P
D Y K K L S F P E G F K W E R V M N F E
D G G V V T V T Q D S S L Q D G C F I Y
K V K F I G V N F P S D G P V M Q K K T
M G W E A S T E R L Y P R D G V L K G E
I H K A L K L K D G G H Y L V E F K S I
Y M A K K P V Q L P G Y Y Y V D S K L D
I T S H N E D Y T I V E Q Y E R T E G R
H H L F L
```

FIG. 18   SEQ ID NO: 5 nucleotide sequence of the *Discosoma* variant fast T1 red fluorescent protein open reading frame atggcctcctccgaggacgtcatcaaggagttcatgcgcttcaaggtgcgcatggagggc
tccgtgaacggccacgagttcgagatcgagggcgagggcgagggccgcccctacgagggc
acccagaccgccaagctgaaggtgaccaaggggcggcccctgcccttcgcctggacatc
ctgtcccccagttccagtacggctccaagtgtacgtgaagcacccgacatcccc
gactacaagaagctgtccttcccgaggctccaagtgggagcgcgtgatgaacttcgag
gacggcggcgtggtgaccgtgacccaggactcctccctgcaggacggctccttcatctac
aaggtgaagttcatcggcgtgaacttcccctccgagcgcctgtaccccgacgcctaatgcagaagaagact
atgggctggaggccctcgaagctgaaggacggccgcactacctggtggagttcaagtccatc
tacatggccaagaagcccgtgcagctgccccgctactactacgtggactccaagctggac
atcacctcccacaacgaggactacaccatcgtggagcagtacgagcgcgccgagggccgc
caccacctgttcctgtag

FIG. 19 SEQ ID NO: 4 amino acid sequence of the *Discosoma* variant fast T1 red fluorescent protein

| | | | | | | | | | | | |
|---|---|---|---|---|---|---|---|---|---|---|---|
| T1 (as received from B. Glick) | P-4L | R2A | K5E | N6D | | T21S | H41T | N42Q | V44A | | |
| T1 + I125R (after subcloning into our preferred vector) | V1a | R2A | K5E | N6D | | T21S | H41T | N42Q | V44A | | |
| dimer1 | V1a | R2A | K5E | N6D | | T21S | H41T | N42Q | V44A | | |
| dimer1.02 | V1a | R2A | K5E | N6D | | T21S | H41T | N42Q | V44A | | | V71A |
| 1.26 | V1a | R2A | K5E | N6D | | T21S | H41T | N42Q | V44A | | | V71A |
| 1.28 | V1a | R2A | K5E | N6D | | T21S | H41T | N42Q | V44A | K47R | | V71A |
| 1.34 | V1a | R2A | K5E | N6D | | T21S | H41T | N42Q | V44A | | K70R | V71A |
| dimer1.56 | V1a | R2A | K5E | N6D | | T21S | H41T | N42Q | V44A | | K70R | V71A |
| 1.61 | V1a | R2A | K5E | N6D | | T21S | H41T | N42Q | V44A | | K70R | |
| 1.76 | V1a | R2A | K5E | N6D | | T21S | H41T | N42Q | V44A | | K70R | |
| dimer2 | V1a | R2A | K5E | N6D | | T21S | H41T | N42Q | V44A | | | V71A |
| non-aggregating mutations | | X | X | X | | | | | | | | |
| AB interface | | | | | | | | | | | | |
| AC interface | | | | | | | | | | | | |
| external to barrel | X | | | | | X | X | | | | | |
| internal to barrel | | | | | | | | X | X | | | X |
| mRFP0.1 | V1a | R2A | K5E | N6D | | T21S | H41T | N42Q | V44A | | | |
| mRFP0.2 | V1a | R2A | K5E | N6D | | T21S | H41T | N42Q | V44A | | | |
| mRFP0.3 | V1a | R2A | K5E | N6D | | T21S | H41T | N42Q | V44A | | K70R | |
| mRFP0.4a | V1a | R2A | K5E | N6D | | T21S | H41T | N42Q | V44A | | K70R | |
| mRFP0.4b | V1a | R2A | K5E | N6D | | T21S | H41T | N42Q | V44A | | | V71A |
| mP11 | V1a | R2A | K5E | N6D | | T21S | H41T | N42Q | V44A | | K70R | |
| mP17 | V1a | R2A | K5E | N6D | | T21S | H41T | N42Q | V44A | | K70R | |
| m1.01 | V1a | R2A | K5E | N6D | | T21S | H41T | N42Q | V44A | | K70R | |
| m1.02 | V1a | R2A | K5E | N6D | | T21S | H41T | N42Q | V44A | | K70R | |
| mRFP0.5a | V1a | R2A | K5E | N6D | | T21S | H41T | N42Q | V44A | | K70R | |
| m1.12 | V1a | R2A | K5E | N6D | | T21S | H41T | N42Q | V44A | | K70R | |
| mRFP0.5b | V1a | R2A | K5E | N6D | | T21S | H41T | N42Q | V44A | | | V71A |
| m1.15 | V1a | R2A | K5E | N6D | F11S | T21S | H41T | N42Q | V44A | | K70R | |
| m1.19 | V1a | R2A | K5E | N6D | | T21S | H41T | N42Q | V44A | | K70R | |
| mRFP0.6 | V1a | R2A | K5E | N6D | | T21S | H41T | N42Q | V44A | | | V71A |
| m124 | V1a | R2A | K5E | N6D | | T21S | H41T | N42Q | V44A | | | V71A |
| m131 | V1a | R2A | K5E | N6D | | T21S | H41T | N42Q | V44A | | | V71A |
| m141 | V1a | R2A | K5E | N6D | | T21S | H41T | N42Q | V44A | | | V71A |
| m163 | V1a | R2A | K5E | N6D | | T21S | H41T | N42Q | V44A | | | V71A |
| m173 | V1a | R2A | K5E | N6D | | T21S | H41T | N42Q | V44A | | | V71A |
| m187 | V1a | R2A | K5E | N6D | | T21S | H41T | N42Q | V44A | | | V71A |
| m193 | V1a | R2A | K5E | N6D | | T21S | H41T | N42Q | V44A | | | V71A |
| m200 | V1a | R2A | K5E | N6D | | T21S | H41T | N42Q | V44A | | | V71A |
| m205 | V1a | R2A | K5E | N6D | | T21S | H41T | N42Q | V44A | | | V71A |
| m220 | V1a | R2A | K5E | N6D | | T21S | H41T | N42Q | V44A | | | V71A |
| mRFP1 | | R2A | K5E | N6D | | T21S | H41T | N42Q | V44A | | | V71A |
| non-aggregating mutations | | X | X | X | | | | | | | | |
| AB interface | | | | | | | | | | | | |
| AC interface | | | | | | | | | | | | |
| external to barrel | | | | | | X | X | | | | | |
| internal to barrel | | | | | | | | X | X | | | X |

FIG. 20B

| Variant | 78 | 83 | 117 | 118 | 124 | 125 | 127 | 131 | 144 | 145 | 149 | 150 |
|---|---|---|---|---|---|---|---|---|---|---|---|---|
| T1 (as received from B. Glick) | | | C117S | | | | | | | | | |
| T1 + I125R (after subcloning into our preferred vector) | | | C117S | | | I125R | | | | | | |
| dimer1 | | | | | | I125R | | | | | | |
| dimer1.02 | | | | | | I125R | | S131P | | | | |
| 1.26 | | | | | | I125R | | S131P | | | | |
| 1.28 | D78G | | | | | I125R | | S131P | | | | |
| 1.34 | | | | | | I125R | | S131P | | | | |
| dimer1.56 | | | | F118L | | I125R | | S131P | | | | |
| 1.61 | | | | | | I125R | | S131P | | | | |
| 1.76 | | | | F118L | | I125R | | S131P | | | | |
| dimer2 | | | C117T | F118L | | I125R | V127T | S131P | | | | |
| non-aggregating mutations | | | | | | | | | | | | |
| AB interface | | | | | | x | x | | | | | |
| AC interface | | | | | | | | | | | | |
| external to barrel | | | x | | | | x | | | | | |
| internal to barrel | | | | x | | | | | | | | |
| | | | | | | | | | | | | |
| mRFP0.1 | | | | | | I125R | | | E144A | A145R | | |
| mRFP0.2 | | | | | | I125R | | | E144A | A145R | | |
| mRFP0.3 | | | C117E | | F124L | I125R | V127T | | | | | |
| mRFP0.4a | | K83I | C117E | | F124L | I125R | V127T | | | | | |
| mRFP0.4b | | K83L | C117E | | F124L | I125R | V127T | | | | | |
| mP11 | | K83I | C117E | | F124L | I125R | V127T | | | | | |
| mP17 | | K83I | C117E | | F124L | I125R | V127T | | | | | |
| m1.01 | | K83I | C117E | | F124L | I125R | V127T | | | | | |
| m1.02 | | K83I | C117E | | F124L | I125R | V127T | | | | | |
| mRFP0.5a | | K83I | C117E | | F124L | I125R | V127T | | | | | |
| m1.12 | | K83I | C117E | | F124L | I125R | V127T | | | | | |
| mRFP0.5b | | K83L | C117E | | F124L | I125R | V127T | | | | | L150M |
| m1.15 | | K83I | C117E | | F124L | I125R | V127T | | | | | |
| m1.19 | | K83I | C117E | | F124L | I125R | V127T | | | | | |
| mRFP0.6 | | K83L | C117E | | F124L | I125R | V127T | | | | | L150M |
| m124 | | K83L | C117E | | F124L | I125R | V127T | | | | | L150M |
| m131 | | K83L | C117E | | F124L | I125R | V127T | | | | | |
| m141 | | K83L | C117E | | F124L | I125R | V127T | | | | | |
| m163 | | K83L | C117E | | F124L | I125R | V127T | | | A145P | | L150M |
| m173 | | K83L | C117E | | F124L | I125R | V127T | | | | | L150M |
| m187 | | K83L | C117E | | F124L | I125R | V127T | | | | R149H | L150M |
| m193 | | K83L | C117E | | F124L | I125R | V127T | | | | | L150M |
| m200 | | K83L | C117E | | F124L | I125R | V127T | | | A145P | R149H | L150M |
| m205 | | K83L | C117E | | F124L | I125R | V127T | | | A145P | R149H | |
| m220 | | K83L | C117E | | F124L | I125R | V127T | | | | | L150M |
| mRFP1 | | K83L | C117E | | F124L | I125R | V127T | | | | | L150M |
| non-aggregating mutations | | | | | | | | | | | | |
| AB interface | | | | | | x | x | | | | | |
| AC interface | | | | | | | | | | | | |
| external to barrel | | x | | | | | | | | | | |
| internal to barrel | x | | | | x | | | | | | | x |

FIG. 20C

| Variant | 153 | 156 | 162 | 163 | 164 | 168 | 174 | 175 | 177 | 179 | 180 |
|---|---|---|---|---|---|---|---|---|---|---|---|
| T1 (as received from B. Glick) | | | | | | | | | | | |
| T1 + I125R (after subcloning into our preferred vector) | | | | | | | | | | | |
| dimer1 | | | | K163Q | | | | | | S179T | |
| dimer1.02 | | | | K163Q | | | | | | S179T | |
| 1.26 | | | | K163Q | | | | | | S179T | |
| 1.28 | | | | K163Q | | | | | | S179T | |
| 1.34 | | | | K163Q | | K168R | | | | S179T | |
| dimer1.56 | | | | K163Q | | | | | | S179T | |
| 1.61 | | | | K163Q | | | | | | S179T | |
| 1.76 | | | | K163Q | | | | | | S179T | |
| dimer2 | | | | K163Q | | | | | | S179T | |
| non-aggregating mutations | | | | | | | | | | | |
| AB interface | | | | | | | | | | | |
| AC interface | | | | | | | | | | | |
| external to barrel | | | | | | | | | | | |
| internal to barrel | | | | X | | | | | | X | |
| mRFP0.1 | | | H162K | K163M | A164R | | | | | S179T | |
| mRFP0.2 | | | H162K | K163M | A164R | | | | | S179T | |
| mRFP0.3 | | | H162K | K163M | A164R | | | | | S179T | |
| mRFP0.4a | | | H162K | K163M | A164R | | | | | S179T | |
| mRFP0.4b | | | H162K | K163M | A164R | | | | | S179T | |
| mP11 | | | H162K | K163M | A164R | | | | | S179T | |
| mP17 | | | H162K | K163M | A164R | | | | | S179T | |
| m1.01 | | | H162K | K163M | A164R | | | | F177C | S179T | |
| m1.02 | | | H162K | K163M | A164R | | | V175A | | S179T | |
| mRFP0.5a | | | H162K | K163M | A164R | | | | F177S | S179T | |
| m1.12 | | | H162K | K163T | A164R | | | | | S179T | |
| mRFP0.5b | | V156A | H162K | K163M | A164R | | | | | S179T | |
| m1.15 | | | H162K | K163M | A164R | | | V175A | | S179T | |
| m1.19 | | | H162K | K163M | A164R | | L174P | | | S179T | |
| mRFP0.6 | | V156A | H162K | K163M | A164R | | L174D | V175A | F177V | S179T | I180T |
| m124 | | V156A | H162K | K163M | A164R | | L174A | V175A | F177V | S179T | I180T |
| m131 | | | H162K | K163M | A164R | | L174G | | F177T | S179T | |
| m141 | | V156A | H162K | K163M | A164R | | L174T | V175A | F177V | S179T | |
| m163 | R153E | V156A | H162K | K163M | A164R | | L174D | V175A | F177V | S179T | |
| m173 | R153E | V156A | H162K | K163M | A164R | | L174D | V175A | F177V | S179T | I180T |
| m187 | R153E | V156S | H162K | K163M | A164K | | L174G | | F177T | S179T | |
| m193 | R153E | V156A | H162R | K163M | A164R | | L174D | V175A | F177V | S179T | I180T |
| m200 | R153E | | H162K | K163M | A164R | | L174G | | F177T | S179T | |
| m205 | R153E | V156A | H162K | K163M | A164R | | L174D | V175A | F177V | S179T | I180T |
| m220 | R153E | V156A | H162R | K163M | A164R | | L174D | V175A | F177V | S179T | I180T |
| mRFP1 | R153E | V156A | H162K | K163M | A164R | | L174D | V175A | F177V | S179T | I180T |
| non-aggregating mutations | | | | | | | | | | | |
| AB interface | | | | | | | | | | | X |
| AC interface | X | | X | | X | | X | | | | |
| external to barrel | | X | | | | | | | | | |
| internal to barrel | | | | X | | | | X | X | X | |

FIG. 20D

| Variant | 192 | 194 | 195 | 197 | 209 | 217 | 220 | 222 | 223 | 224 | 225 |
|---|---|---|---|---|---|---|---|---|---|---|---|
| T1 (as received from B. Glick) | | | | | | T217A | | | | | |
| T1 + I125R (after subcloning into our preferred vector) | | | | | | T217A | | | | | |
| dimer1 | | | | S197T | | T217A | | | | | |
| dimer1.02 | | | | S197T | | T217A | | | | | |
| 1.26 | | | | S197T | | T217S | | | | | |
| 1.28 | | | | S197A | | T217A | | | | | |
| 1.34 | | | | S197T | | T217A | | | | | |
| dimer1.56 | | | | S197T | | T217S | | | | | |
| 1.61 | | | | S197T | | T217A | | | | | |
| 1.76 | | | | S197T | | T217S | | | | | |
| dimer2 | | | | S197T | | T217S | | | | | |
| non-aggregating mutations | | | | | | | | | | | |
| AB interface | | | | | | | | | | | |
| AC interface | | | | | | | | | | | |
| external to barrel | | | | | | | | | | | |
| internal to barrel | | | | X | | X | | | | | |
| mRFP0.1 | | | | S197T | | T217A | | H222G | | F224G | |
| mRFP0.2 | Y192C | | | S197T | | T217A | | H222G | | F224G | |
| mRFP0.3 | Y192A | Y194A | | S197T | | T217S | | H222G | | F224G | |
| mRFP0.4a | Y192A | Y194A | | S197T | | T217S | | H222G | L223E | F224G | L225A |
| mRFP0.4b | Y192A | Y194K | V195T | S197I | | T217A | | H222C | L223T | F224G | L225A |
| mP11 | Y192A | Y194A | | S197T | | T217S | | H222G | L223A | F224G | L225A |
| mP17 | Y192A | Y194A | | S197T | | T217S | | H222G | L223T | F224G | L225E |
| m1.01 | Y192A | Y194A | | S197T | T209S | T217S | R220H | H222G | L223E | F224G | L225A |
| m1.02 | Y192A | Y194A | | S197T | | T217S | | H222G | L223E | F224G | L225A |
| mRFP0.5a | Y192A | Y194A | | S197T | | T217S | | H222G | L223E | F224G | L225A |
| m1.12 | Y192A | Y194A | | S197T | | T217S | | H222G | L223E | F224G | L225A |
| mRFP0.5b | Y192A | Y194K | V195T | S197I | | T217A | | H222C | L223T | F224G | L225A |
| m1.15 | Y192A | Y194A | | S197T | | T217S | | H222G | L223E | F224G | L225A |
| m1.19 | Y192A | Y194A | | S197T | | T217S | | H222G | L223E | F224G | L225A |
| mRFP0.6 | Y192A | Y194K | V195T | S197I | | T217A | | H222C | L223T | F224G | L225A |
| m124 | Y192A | Y194K | V195T | S197I | | T217A | | H222C | L223T | F224G | L225A |
| m131 | Y192A | Y194K | V195T | S197I | | T217A | | H222C | L223T | F224G | L225A |
| m141 | Y192A | Y194K | V195T | S197I | | T217A | | H222C | L223T | F224G | L225A |
| m163 | Y192A | Y194K | V195T | S197I | | T217A | | H222C | L223T | F224G | L225A |
| m173 | Y192A | Y194K | V195T | S197I | | T217A | | H222C | L223T | F224G | L225A |
| m187 | Y192A | Y194K | V195T | S197I | | T217A | | H222G | L223T | F224G | L225E |
| m193 | Y192A | Y194K | V195T | S197I | | T217A | | H222G | L223S | F224G | L225E |
| m200 | Y192A | Y194K | V195T | S197I | | T217S | | H222G | L223T | F224G | L225T |
| m205 | Y192A | Y194K | V195T | S197I | | T217A | | H222G | L223T | F224G | L225T |
| m220 | Y192A | Y194K | V195T | S197I | | T217A | | H222G | L223S | F224G | L225E |
| mRFP1 | Y192A | Y194K | V195T | S197I | | T217A | | H222S | L223T | F224G | L225A |
| non-aggregating mutations | | | | | | | | | | | |
| AB interface | | | | | | | | | | | |
| AC interface | X | X | | | | | | X | X | X | X |
| external to barrel | | | | | | | | | | | |
| internal to barrel | | | X | X | | X | | | | | |

FIG. 21   SEQ ID NO: 7 nucleotide sequence of the *Discosoma* variant red fluorescent protein dimer2 open reading frame atggtggcctcctccgaggacgtcatcaaagagttcatgcgcttcaaggtgcgcatggag
ggctccgtgaacggccacgagttcgagatcgagggcgagggcgagggccgcccctacgag
ggcacccagaccgccaagctgaaggtgaccaaggggcccccctgcccttcgcctgggac
atcctgtccccccagttccagtacggctccaaggcctacgtgaagcaccccgccgacatc
cccgactacaagaagctgtccttcccgagggcttcaagtgggagcgcgtgatgaacttc
gaggacggcgcgtggtgaccgtgacccaggactcctccctgcaggacggcacgctgatc
tacaaggtgaagttccgcggcaccaacttcccccccgacgcccgtaatgcagaagaag
accatgggctgggaggcctgaagctgaaggacggcggccactacctggtggagttcaagacc
gagatccaccaggccctgaagctgaaggacggcggccactacctggtggagttcaagacc
atctacatggccaagaagcccgtgcagctgcccggctactactgtggacaccaagctg
gacatccacctcccaacgaggactacaccatcgtgaacagtacgagcgctccgaggc
cgccaccaccctgttcctgtag

FIG. 22    SEQ ID NO: 6 amino acid sequence of the *Discosoma* variant red fluorescent protein dimer2

```
M V A S S E D V I K E F M R F K V R M E
G S N G H E F E I E G E G R P Y E
G T Q T A K L K V T K G G P L P F A D I
I L P D Y K K L S F P E G F K W E R V M N F
P D Y K K L S F P E G F K W E R V M N F
E D G V F R G T N F P P D G P V L K G
Y K V K F E G V N F P S D G P V M Q K K
T M G W E A S T E R L Y P R D G V L K G
E I H Q A L K P V Q L P G Y Y Y V D T K L
I Y M A K K P V Q L P G A Y Y V D T K L
D I T S H N E D Y T I V E Q Y E R S E G
R H H L F L
```

FIG. 23  SEQ ID NO: 9 nucleotide sequence of the *Discosoma* variant red fluorescent protein mRFP1 open reading frame

```
atggcctcctccgaggacgtcatcaaggagttcatgcgcttcaaggtgcgcatggagggc
tccgtgaacggccacgagttcgagatcgagggcgagggcgagggccgcccctacgagggc
acccagaccgccaagctgaaggtgaccaagggcggccccctgccctttgcctggacatc
ctgtcccctcagttccagtacggctccaaggcctacgtgaagcaccccgacatcccc
gactacttgaagctgtccttccccgagggcttcaagtgggagcgcgtgatgaacttcgag
gacggcggcgtgtgtgaccgtgaccagcaccaacttccccctgcaggacggcgagttcatctac
aaggtgaagctgcgcggcaccaacttccccctgcaggacggcccgtaatgcagaagaagacc
atgggctgggaggcctccaccgagcgcatgtacccgaggacggcgccctgaagggcgag
atcaagatgaggctgaaggctgaaggacgcggcactacgacgccgaggtcaagaccacc
tacatggccaagaagcccgtgcagctgcccggcgcctacaagaccgacatcaagctggac
atcacctcccacaacgaggactacaccatcgtggaacagtacgagcgcgccgagggccgc
cactccaccggcgcctaa
```

FIG. 24  SEQ ID NO: 8 amino acid sequence of the *Discosoma* variant red fluorescent protein mRFP1

```
M A S S E D V I K E F M R F K V R M E G
S V N G H E F E I E G E G R P Y E G  
T Q T A K L K V T K G G P L P F A W D I
L S P Q F Q Y G S K A Y V K H P A D I P
D Y L K L S F P E G F K W E R V M N F E
D G G V V T V T Q D S S L Q D G E F I Y
K V K L R G T N F P S D G P V M Q K K T
M G W E A S T E R M Y P E D G A L K G E
I K M R L K L K D G G H Y D A E V K T T
Y M A K K P V Q L P G A Y K T D I K L D
I T S H N E D Y T I V E Q Y E R A E G R
H S T G G M D E L Y K
```

FIG. 25  SEQ ID NO: 23 nucleotide sequence of a modified *Discosoma* wild-type red fluorescent protein open reading frame with humanized codon usage

```
atggtgcgctcctccaagaacgtcatcaaggagttcatgcgcttcaaggtgcgcatggag
ggcaccgtgaacggccacgagttcgagatcgagggcgagggcgagggccgcccctacgag
ggccacaacaccgtgaagctgaaggtgaccaagggcggccccctgccctttcgcctggac
atcctgtcccccagttccagtacggctccaagaggagctccccgcgagggcttcaagtgggagcgcgtgatgaacttc
cccgactacaagaagctgtcccttcccccgagggcttcaagtgggagcgcgtgatgaacttc
gaggacggcggcgtggtgaccgtgacccaggactcctccctgcaggacggctgcttcatc
tacaaggtgaagttcatcggcgtgaacttcccctccgacggccccgtaatgcagaagaag
accatgggctgggaggccctgaagctgaaggacggcggccactacctggtggagttcaagtcc
gagatccacaaggccaagaagccctgcagctgcccgctactactacgtggactccaagctg
atctacatggccaagaagccctgcagctgcccgctactactacgtggactccaagctg
gacatcacctccacaagagcggactacaccatcgtggagcagtacgagcgcaccgaggg
cgccacccctgttcctgtag
```

FIG. 30    SEQ ID NO: 79 mRFP1.1 amino acid sequence

```
M A S S E D V I K E F M R F K V R M E G
S V N G H E F E I E G E G E G R P Y E G
T Q T A K L K V T K G G P L P F A W D I
L S P Q F M Y G S K A Y V K H P A D I P
D Y L K L S F P E G F K W E R V M N F E
D G G V V T V T Q D S S L Q D G C F I Y
K V K F I G V N F P S D G P V M Q K K T
M G W E A S T E R L Y P R D G V L K G E
I H K A L K L K D G G H Y L V E F K T I
Y M A K K P V Q L P G Y Y Y V D S K L D
H T S H N E D Y T I V E Q Y E R T E G R
H S T G G M D E L Y K —
```

FIG. 31  SEQ ID NO: 80 mRFP1.1 DNA sequence atggcctcctccgaggacgtcatcaaggagttcatgcgcttcaaggtgcgcatggagggc
tccgtgaacggccacgagttcgagatcgagggcgagggcgagggccgcccctacgagggc
acccagaccgccaagctgaaggtgaccaaggggcgcccctgcccttcgcctggacatc
ctgtcccctcagttcatgtacggctccaaggcctacgtgaagcaccccgacatccccc
gactacttgaagctgtccttccccgagggcttcaagtgggagcgcgtgatgaacttcgag
gacggcggcgtggtgaccgtgacccagactcctcccgacggctacgtggagttcatctac
aaggtgaagctgcgcggaggcctcctccgagcggatgtacccgaggacggccctgaagggcgag
atgggctgggaggcctcctccgagcggatgtacccgaggacggccctgaagggcgag
atcaagatgaggctgaagctgaaggactgaagctacgcgccgaggtcaagaccaccacc
tacatggccaagaagcccgtgcagctgcccggctacttaccgctctaagccgctggac
atcacctcccacaacgaggactacaccatcgtggaacagtacgagcgcgcgagggccgc
cactccaccggcgcctaa

US 7,005,511 B2

FLUORESCENT PROTEIN VARIANTS AND METHODS FOR MAKING SAME

This application is a continuation-in-part application claiming priority under 35 U.S.C. § 120 to copending U.S. patent application Ser. No. 10/121,258 filed on Apr. 10, 2002, which is a continuation-in-part of U.S. patent application Ser. No. 09/866,538, filed May 24, 2001 now U.S. Pat. No. 6,852,849, which is a continuation-in-part of U.S. patent application Ser. No. 09/794,308, filed Feb. 26, 2001, the disclosures of which are hereby expressly incorporated by reference in their entirety.

This invention was made in part with Government support under Grant No. NS27177, awarded by the National Institute of Neurological Disorders and Stroke, and under Grant No. GM62114-01, awarded by the National Institute of General Medical Sciences. The Government may have certain rights in this invention.

BACKGROUND OF THE INVENTION

1. Field of the Invention

The present invention relates generally to variant red fluorescent proteins (RFPs), and more specifically to Anthozoan fluorescent proteins (AnFP), having at least one amino acid alteration that results in more efficient maturation than the corresponding wild-type protein or another variant RFP from which such variants derive. The invention further concerns RFP variants that additionally have reduced propensity tetramerize, and thus form predominantly monomeric and/or dimeric structures. The invention also relates to methods of making and using such RFP variants.

2. Description of the Related Art

The identification and isolation of fluorescent proteins in various organisms, including marine organisms, has provided a valuable tool to molecular biology. The green fluorescent protein (GFP) of the jellyfish *Aequorea victoria*, for example, has become a commonly used reporter molecule for examining various cellular processes, including the regulation of gene expression, the localization and interactions of cellular proteins, the pH of intracellular compartments, and the activities of enzymes.

The usefulness of *Aequorea* GFP has led to the identification of numerous other fluorescent proteins in an effort to obtain proteins having different useful fluorescence characteristics. In addition, spectral variants of *Aequorea* GFP have been engineered, thus providing proteins that are excited or fluoresce at different wavelengths, for different periods of time, and under different conditions. The identification and cloning of a red fluorescent protein from *Discosoma* coral, termed DsRed or drFP583, has raised a great deal of interest due to its ability to fluoresce at red wavelengths.

The DsRed from *Discosoma* (Matz et al., *Nature Biotechnology* 17:969–973 [1999]) holds great promise for biotechnology and cell biology as a spectrally distinct companion or substitute for the green fluorescent protein (GFP) from the *Aequorea* jellyfish (Tsien, *Ann. Rev. Biochem.,* 67:509–544 [1998]). GFP and its blue, cyan, and yellow variants have found widespread use as genetically encoded indicators for tracking gene expression and protein localization and as donor/acceptor pairs for fluorescence resonance energy transfer (FRET). Extending the spectrum of available colors to red wavelengths would provide a distinct new label for multicolor tracking of fusion proteins and together with GFP (or a suitable variant) would provide a new FRET donor/acceptor pair that should be superior to the currently preferred cyan/yellow pair (Mizuno et al., *Biochemistry* 40:2502–2510 [2001]).

One problem associated with the use of DsRed as a fluorescent report is its slow and inefficient chromophore maturation. Most previous attempts to improve the rate and/or extent of maturation of DsRed (Verkhusha et al., *J. Biol. Chem.,* 276:29621–29624 [2001]; and Terskikh et al., *J. Biol. Chem.,* 277:7633–7636 [2002]) including the commercially available DsRed2 (CLONTECH, Palo Alto, Calif.), have provided only modest improvements. Recently, an engineered variant of DsRed, known as T1 (shown in FIG. 1A), has become available and effectively solved the problem of the slow maturation (Bevis and Glick, *Nat. Biotechnol.,* 20:83–87 [2002]). However this variant appears to still suffer from an incomplete maturation and therefore like DsRed, a significant fraction of the protein remains as the green fluorescent intermediate in the aged tetramer.

Furthermore, all coelenterate fluorescent proteins cloned to date display some form of quaternary structure, including the weak tendency of *Aequorea* green fluorescent protein (GFP) to dimerize, the obligate dimerization of *Renilla* GFP, and the obligate tetramerization of the *Discosoma* DsRed (Baird et al., *Proc. Natl. Acad. Sci. USA* 97:11984–11989 [2000]; and Vrzheshch et al., *FEBS Lett.,* 487:203–208 [2000]). While the weak dimerization of *Aequorea* GFP has not impeded its acceptance as an indispensable tool of cell biology, the obligate tetramerization of DsRed has greatly hindered its development from a scientific curiosity to a generally applicable and robust tool, most notably as genetically encoded fusion tag.

DsRed tetramerization presents an obstacle for the researcher who wishes to image the subcellular localization of a red fluorescent chimera, as the question exists as to what extent will fusing tetrameric DsRed to the protein of interest affect the location and function of the latter. Furthermore, it can be difficult in some cases to confirm whether a result is due, for example, to a specific interaction of two proteins under investigation, or whether a perceived interaction is an artifact caused by the oligomerization of fluorescent proteins linked to each of the two proteins under investigation. There have been several published reports (see, e.g., Mizuno et al., *Biochemistry* 40:2502–2510 [2001]; and Lauf et al., *FEBS Lett.,* 498:11–15 [2001]) and many unpublished anecdotal communications, in which DsRed chimeras have been described as forming intracellular aggregates that have lost their biological activity. DsRed also suffers from slow and incomplete maturation (Baird et al., *Proc. Natl. Acad. Sci. USA* 97:11984–11989 [2000]).

One approach to overcome these shortcomings has been to continue the search for DsRed homologues in sea coral and anemon; an approach that has yielded several red shifted proteins (Fradkov et al., *FEBS Lett.,* 479:127–130 [2000]; and Lukyanov et al., *J. Biol. Chem.,* 275:25879–25882 [2000]). However, the fundamental problem of tetramerization has yet to be overcome. The only published progress towards decreasing the oligomeric state of a red fluorescent protein involved an engineered DsRed homologue, commercially available as HcRed1 (CLONTECH), which was converted to a dimer with a single interface mutation (Gurskaya et al., *FEBS Lett.,* 507:16–20 [2001]). Although HcRed1 has the additional benefit of being 35 nm red-shifted from DsRed, it is limited by a low extinction coefficient (20,000 M−1 cm−1) and quantum yield (0.015) (CLONTECH Laboratories Inc., (2002) Living Colors User Manual Vol. II: Red Fluorescent Protein [Becton, Dickinson and Company], p. 4) making the protein problematic to use in experimental systems.

A methionine is found at position 66 of a tetrameric nonfluorescent chromoprotein from *Anemonia sulcata* which was converted to a fluorescent protein through the introduction of two mutations (Lukyanov, K. A., Fradkov, A. F., Gurskaya, N. G., Matz, M. V., Labas, Y. A., Savitsky, A. P., Markelov, M. L., Zaraisky, A. G., Zhao, X., Fang, Y. et al. (2000) *J. Biol. Chem.* 275, 25879–25882). Introduction of a methionine at position 66 apparently improves the fluorescent properties of both a green (zFP506) and a cyan (amFP486) tetrameric fluorescent protein though no details have been published (Yanushevich, Y. G., Staroverov, D. B., Savitsky, A. P., Fradkov, A. F., Gurskaya, N. G., Bulina, M. E., Lukyanov, K. A. & Lukyanov, S. A. (2002) *FEBS Lett.* 511, 11–14).

Thus, there exists a need in the art for the development of red fluorescent polypeptides that find use in scientific applications without technical limitations due to inefficient and slow chromophore maturation, and oligomerization, especially tetramerization. There exists a need for methods to produce red fluorescent proteins (RFPs) exhibiting more efficient chromophore maturation than wild-type RFPs or other RPF variants. Furthermore, there exists a need for RFPs that additionally have reduced propensity for oligomerization, such as, tetramerization. Most significantly, there exists a need for RFP variants with improved efficiency of maturation that demonstrate useful fluorescence in a monomeric state in experimental systems. The present invention satisfies these needs and provides additional advantages.

SUMMARY OF THE INVENTION

The present invention concerns variants of red fluorescent proteins (RFPs) comprising at least one amino acid alteration resulting in more efficient chromophore maturation than a corresponding wild-type or variant RFP. The present invention further concerns RFP variants that, in addition to showing more efficient maturation, have a reduced propensity to form tetramers. Thus, certain RFP variants of the invention have a propensity to form monomers and dimers, where the native form of the RFP has a propensity to form tetrameric structures.

In one aspect, the invention concerns an Anthozoan fluorescent protein (AnFP) having a reduced propensity to oligomerize, comprising at least one mutation within the wild-type AnFP amino acid sequence that reduces or eliminates the ability of the fluorescent protein to tetramerize and/or dimerize, as the case may be. The AnFP preferably is the red fluorescent protein of *Discosoma* (DsRed) of SEQ ID NO: 1, but is by no means so limited. In some embodiments, the invention concerns an Anthozoan fluorescent protein (AnFP), e.g., DsRed, comprising at least one amino acid substitution within the AB and/or AC interface of said fluorescent protein (e.g., DsRed) that reduces or eliminates the degree of oligomerization of said fluorescent protein.

In another embodiment, the variant AnFP (e.g., DsRed) having a reduced propensity to oligomerize is a monomer in which the interfaces between the oligomeric subunits are disrupted by introducing mutations, e.g., substitutions, which interfere with oligomerization (including dimerization), and, if necessary, introducing further mutations needed to restore or improve fluorescence which might have been partially or completely lost as a result of disrupting the interaction of the subunits.

The invention specifically includes dimeric and monomeric variants of other fluorescent proteins in addition to DsRed, such as fluorescent proteins from other species and fluorescent proteins that have fluorescence emission spectra in wavelengths other than red. For example, green fluorescent proteins and fluorescent proteins from *Renilla* sp. find equal use with the invention. Furthermore, fluorescent proteins that normally have the propensity to form tetramers and/or dimers find equal use with the invention.

In a particular embodiment, the fluorescent protein is DsRed, and a DsRed variant having a reduced propensity to oligomerize (in this case, tetramerize) is prepared by first replacing at least one key residue in the AC and/or AB interface of the wild-type protein, thereby creating a dimer or monomer form, followed by the introduction of further mutation(s) to restore or improve red fluorescence properties.

The invention provides variant fluorescent proteins, including but not limited to DsRed, comprising amino acid substitutions relative to the respective wild-type sequences, where the substitutions impart the advantageous properties to the polypeptide variants. These amino acid substitutions can reside at any position within the polypeptide, and are not particularly limited to any type of substitution (conservative or non-conservative). In one embodiment, the mutations restoring or improving fluorescence are amino acid substitutions within the plane of the chromophore and/or just above the plane of the chromophore and/or just below the plane of the chromophore of the fluorescent protein.

In one aspect, the invention provides a polynucleotide sequence encoding a *Discosoma* red fluorescent protein (DsRed) variant having a reduced propensity to oligomerize, comprising one or more amino acid substitutions at the AB interface, at the AC interface, or at the AB and AC interfaces of the wild-type DsRed amino acid sequence of SEQ ID NO: 1, where the substitutions result in reduced propensity of the DsRed variant to form tetramers, wherein said variant displays detectable fluorescence of at least one red wavelength. In one embodiment, this protein sequence has at least about 80% sequence identity with the amino acid sequence of SEQ ID NO: 1. In another embodiment, the fluorescent protein has detectable fluorescence that matures at a rate at least about 80% as fast as the rate of fluorescence maturation of wild-type DsRed of SEQ ID NO: 1, while in another embodiment the protein has improved fluorescence maturation relative to DsRed of SEQ ID NO: 1. In still another embodiment, the protein substantially retains the fluorescing properties of DsRed of SEQ ID NO: 1.

In some embodiments, the fluorescent protein variant has a propensity to form dimers. Some proteins contain substitutions in the AB interface and form an AC dimer.

In some embodiments, the fluorescent protein variant comprises at least nine amino acid substitutions that are at residues 2, 5, 6, 21, 41, 42, 44, 117, and 217, and additionally at least one more substitution including substitution at residue 125 of SEQ ID NO: 1. The protein can optionally further comprise at least one additional amino acid substitution that is at residue 71, 118, 163, 179, 197, 127, or 131 of SEQ ID NO: 1. In some embodiments, any one or more of said substitutions is optionally selected from R2A, K5E, N6D, T21S, H41T, N42Q, V44A, V71A, C117T, F118L, I125R, V127T, S131P, K163Q/M, S179T, S197T, and T217A/S.

The invention provides fluorescent protein variants that can be the proteins dimer1, dimer1.02, dimer1.25, dimer1.26, dimer 1.28, dimer1.34, dimer1.56, dimer1.61, or dimer1.76, as provided in FIGS. 20A–20D. In one preferred embodiment, the protein variant is dimer2 (SEQ ID NO: 6).

In some embodiments, the fluorescent dimeric protein variant has at least about 90% sequence identity with the amino acid sequence of SEQ ID NO: 1, while in other embodiments, the protein has at least about 95% sequence identity with the amino acid sequence of SEQ ID NO: 1.

In still other embodiments, the fluorescent protein variant is a monomer. In this embodiment, the amino acid substitutions are in the AB interface and the AC interface.

In some embodiments, the monomeric protein variant comprises at least 14 amino acid substitutions that are at residues 2, 5, 6, 21, 41, 42, 44, 71, 117, 127, 163, 179, 197, and 217, and additionally at least one more substitution that is at residue 125 of SEQ ID NO: 1. In other embodiments, the monomeric protein optionally further comprises at least one additional amino acid substitution at residue 83, 124, 125, 150, 153, 156, 162, 164, 174, 175, 177, 180, 192, 194, 195, 222, 223, 224, and 225 of SEQ ID NO: 1. In still other embodiments, the substitutions in the monomeric protein is optionally selected from R2A, K5E, N6D, T21S, H41T, N42Q, V44A, V71A, K83L, C117E/T, F124L, I125R, V127T, L150M, R153E, V156A, H162K, K163Q/M, L174D, V175A, F177V, S179T, I180T, Y192A, Y194K, V195T, S197A/T/I, T217A/S, H222S, L223T, F224G, L225A.

In other embodiments, the monomeric protein variant is selected from mRFP0.1, mRFP0.2, mRFP0.3, mRFP0.4a, mRFP0.4b, mP11, mP17, m1.01, m1.02, mRFP0.5a, m1.12, mRFP0.5b, m1.15, m1.19, mRFP0.6, m124, m131, m141, m163, m173, m187, m193, m200, m205 and m220, as provided in FIGS. 20A–20D. In a preferred embodiment, the monmeric variant is mRFP1 (SEQ ID NO: 8).

In some embodiments, the monomeric variant has at least about 90% sequence identity with the amino acid sequence of SEQ ID NO: 1, while in other embodiments, the protein has at least about 95% sequence identity with the amino acid sequence of SEQ ID NO: 1.

The present invention also provides tandem dimer forms of DsRed, comprising two DsRed protein variants operatively linked by a peptide linker. The peptide linker can be of variable length, where, for example, the peptide linker is about 10 to about 25 amino acids long, or about 12 to about 22 amino acids long. In some embodiments, the peptide linker is selected from GHGTGSTGSGSS (SEQ ID NO: 17), RMGSTSGSTKGQL (SEQ ID NO: 18), and RMGSTSGSGKPGSGEGSTKGQL (SEQ ID NO: 19).

In some embodiments, the tandem dimer subunit is selected from dimer1, dimer1.02, dimer1.25, dimer1.26, dimer 1.28, dimer1.34, dimer1.56, dimer1.61, dimer1.76, and dimer2, as provided in FIGS. 20A–20D. The tandem dimer can be a homodimer or a heterodimer. In one preferred embodiment, the tandem dimer comprises at least one copy of dimer2 (SEQ ID NO: 6).

The present invention also provides fusion proteins between any protein of interest operatively joined to at least one fluorescent protein variant of the invention. This fusion protein can optionally contain a peptide tag, and this tag can optionally be a polyhistidine peptide tag.

The present invention provides polynucleotides that encode each of the fluorescent protein variants described or taught herein. Furthermore, the present invention provides the fluorescent protein variants encoded by any corresponding polynucleotide described or taught herein. Such polypeptides can include dimeric variants, tandem dimer variants, or monomeric variants.

In other embodiments, the invention provides kits comprising at least one polynucleotide sequence encoding a fluorescent protein variant of the invention. Alternatively, or in addition, the kits can provide the fluorescent protein variant itself.

In other embodiments, the present invention provides vectors that encode the fluorescent protein variants described or taught herein. Such vectors can encode dimeric variants, tandem dimer variants, or monomeric variants, or fusion proteins comprising these variants. The invention also provides suitable expression vectors. In other embodiments, the invention provides host cells comprising any of these vectors.

In another embodiment, the invention provides a method for the generation of a dimeric or monomeric variant of a fluorescent protein which has propensity to tetramerize or dimerize, comprising the steps of mutagenizing at least one amino acid residue in the fluorescent protein to produce a dimeric variant, if the protein had the propensity to tetramerize, and a monomeric variant, if the protein had the propensity to dimerize; and mutagenizing at least one additional amino acid residue to yield a dimeric or monomeric variant, which retains the qualitative ability to fluoresce in the same wavelength region as the non-mutagenized fluorescent protein.

In an optional variation of this method, an additional step can be added, essentially introducing a further mutation into a dimeric variant produced from a fluorescent protein that had the propensity to form tetramers to produce a monomeric variant. In some embodiments, this additional step can come after the first mutagenizing step.

In some embodiments, this method can result in dimeric or monomeric variants has improved fluoresence intensity or fluorescence maturation relative to the non-mutagenized fluorescent protein.

The mutagenesis used in the present method can be by multiple overlap extension with semidegenerate primers, error-prone PCR, site directed mutagenesis, or by a combination of these. The results of this mutagenesis can produce protein variants that have a propensity to form dimers or monomers.

In some embodiments of this method, the fluorescent protein is an Anthozoan fluorescent protein, and optionally, the Anthozoan fluorescent protein fluoresces at a red wavelength. The Anthozoan fluorescent protein can be *Discosoma* DsRed.

In other embodiments, the fluorescent protein variants of the invention can be used in various applications. In one embodiment, the invention provides a method for the detection transcriptional activity, where the method uses a host cell comprising a vector encoding a variant DsRed fluorescent protein operably linked to at least one expression control sequence, and a means to assay said variant fluorescent protein fluorescence. In this method, assaying the fluorescence of the variant fluorescent protein produced by the host cell is indicative of transcriptional activity.

In other embodiments the invention also provides a polypeptide probe suitable for use in fluorescence resonance energy transfer (FRET), comprising at least one fluorescent protein variant of the invention.

In still another embodiment, the invention provides a method for the analysis of in vivo localization or trafficking of a polypeptide of interest, where the method uses a fluorescent fusion protein of the invention in a host cell or tissue, and where the fusion protein can be visualized in the host cell or tissue.

In a further aspect, the invention concerns further improved variants of red fluorescent proteins (RFPs) that have reduced propensity to oligomerize. In particular, the invention concerns RFP variants that not only have a propensity to form monomers and dimers, where the native form of the RFP has a propensity to form tetrameric structures, but are additionally characterized by more efficient maturation than the corresponding non-oligomerizing variants from which they derive. Such variants are typically brighter than the corresponding non-oligomerizing variants, where bightness is typically expressed as the product of the extinction coefficient (EC) and the quantum yield (QY) at the desired red wavelength.

The invention further provides a polynucleotide encoding a variant of a red fluorescent protein (RFP) having a propensity to form tetrameric structures, comprising at least one amino acid alteration resulting in more efficient maturation into the desired red species from the immature green species, and at least one further amino acid alteration resulting in a reduced propensity to tetramerize. The amino acid alteration may be substitution, insertion and/or deletion, and preferably is substitution.

Thus, in one aspect the invention concerns polynucleotide encoding a variant of a red fluorescent protein (RFP) having a propensity to form tetrameric structures, comprising at least one amino acid alteration resulting in higher fluorescence intensity at red wavelength, and at least one further amino acid alteration resulting in a reduced propensity to tetramerize.

In a particular embodiment, the polycleotide encodes a *Discosoma* red fluorescent protein (DsRed) variant.

In another embodiment, the polynucleotide encodes a DsRed variant, in which the amino acid substitution resulting in more efficient maturation is at position 66 of wild-type DsRed of SEQ ID NO: 1. A particular substitution is a Q66M substitution within SEQ ID NO: 1. In another embodiment, the polynucleotide encodes a DsRed variant, in which the amino acid substitution resulting in more efficient maturation is at position 147 of wild-type DsRed of SEQ ID NO: 1. The substitution at position 147 preferably is a T147S substitution, but other substitutions are also possible at this position and are specifically included within the scope of the present invention. In a further embodiment, the polynucleotide of the invention encodes a DsRed variant comprising a substitution at both position 66 and position 147 within SEQ ID NO: 1. In a preferred embodiment, the polynucleotide of the invention encodes a DsRed variant comprising a Q66M and a T147S substitution.

The polynucleotides of the invention encoding DsRed variants comprising at least one amino acid alteration resulting in improved efficiency of chromophore maturation into the desired red form, such as, for example, a Q66M substitution, may additionally contain codons for any of the other amino acid substitutions, alone or in any combination, discussed hereinabove and throughout the present disclosure, in connection with other embodiments. In particular, such polynucleotides (e.g. those encoding a DsRed variant with a Q66M mutation alone or in combination with a T147S substitution) may encode DsRed variants further comprising one or more substitutions at the AB interface, at the AC interface, or at the AB and AC interfaces of the wild-type DsRed amino acid sequence of SEQ ID NO: 1, where the substitutions result in reduced propensity of the DsRed variant to form tetramers.

In a particular embodiment, such polynucleotides encode DsRed variants additionally comprising one or more substitutions at an amino acid position selected from the group consisting of 42, 44, 71, 83, 124, 150, 163, 175, 177, 179, 195, 197, 217, 2, 5, 6, 125, 127, 180, 153, 162, 164, 174, 192, 194, 222, 223, 224, 225, 21, 41, 117, and 156 within the wild-type DsRed amino acid sequence of SEQ ID NO: 1. Possible substitutions at the indicated positions include, without limitation, one or more substitutions selected from the group consisting of N42Q, V44A, V71A, K83L, F124L, L150M, K163M, V175A, F177V, S179T, V195T, S197I, T217A, R2A, K5E, N6D, I125R, V127T, I180T, R153E, H162K, A164R, L174D, Y192A, Y194K, H222S, L223T, F224G, L225A, T21S, H41T, C117E, and V156A within the wild-type DsRed amino acid sequence of SEQ ID NO: 1.

Thus, polynucleotides encoding DsRed variants comprising the following substitutions: N42Q, V44A, V71A, K83L, F124L, L150M, K163M, V175A, F177V, S179T, V195T, S197I, T217A, R2A, K5E, N6D, I125R, V127T, I180T, R153E, H162K, A164R, L174D, Y192A, Y194K, H222S, L223T, F224G, L225A, T21S, H41T, C117E, and V156A within the wild-type DsRed amino acid sequence of SEQ ID NO: 1, are specifically within the scope of the invention. In a preferred embodiment, the invention concerns a polynucleotide encoding a mRFP1.1 shown in FIG. 30 (SEQ ID NO: 79).

In another aspect, the invention concerns a polynucleotide encoding a fusion protein, comprising at least one DsRed protein variant encoded by the polynucleotides discussed above, operatively joined to at least one other polypeptide of interest. In particular embodiments, such fusion proteins may comprising either the Q66M or T147S substitution, or both, as a tandem dimer.

The invention further concerns polypeptides encoded by the polynucleotides discussed above, vectors containing such polynucleotides (including expression vectors), and recombinant host cells transformed with such polynucleotides or vectors.

The invention, in a different aspect, concerns a kit comprising at least one polynucleotide or polypeptide discussed above.

In yet another aspect, the invention concerns a method for the detection transcriptional activity, comprising
  (a) providing a host cell comprising a vector, wherein said vector comprises nucleotide sequence encoding a DsRed fluorescent protein variant comprising at least one amino acid alteration resulting in higher fluorescence intensity at red wavelength, and at least one further amino acid alteration resulting in a reduced propensity to tetramerize operably linked to at least one expression control sequence, and a means to assay said variant fluorescent protein fluorescence, and
  (b) assaying fluorescence of said variant fluorescent protein produced by said host cell, where variant fluorescent protein fluorescence is indicative of transcriptional activity.

In a further aspect, the invention concerns a method for the detection of protein—protein interactions, comprising detection of energy transfer from a fluorescent or bioluminescent protein fusion to a fusion protein as discussed above.

In a still further aspect, the invention concerns a method for the analysis of in vivo localization or trafficking of a polypeptide of interest, comprising the steps of:
  (a) providing a polynucleotide encoding a fusion protein, comprising at least one DsRed protein variant encoded by the polynucleotides discussed above, operatively joined to at least one other polypeptide of interest and a host cell or tissue, and
  (b) visualizing said fusion protein that is expressed in said host cell or tissue.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A shows the tetramer of DsRed with the residues mutated in T1 indicated in blue for external residues and green for those internal to the β-barrel. FIG. 2B shows the AC dimer of DsRed with all mutations present in dimer2 represented as in FIG. 2A and the intersubunit linker present in tdimer2(12) shown as a dotted line. FIG. 2C shows the mRFP1 monomer of DsRed with all mutations present in mRFP1 represented as in FIG. 2A.

FIG. 6A shows two contacting cells transfected with Cx43-mRFP1 and connected by a single large gap junction. FIG. 6B shows one cell microinjected with lucifer yellow at the point indicated by an asterisk and the dye quickly passing (1–2 sec) to the adjacent cell. FIG. 6C shows four neighboring cells transfected with Cx43-dimer2. The bright line between the two right-most cells is the result of having two fluorescent membranes in contact and is not a gap junction. FIG. 6D shows microinjected dye slowly passing to an adjacent cell (observed approximately one third of the time). FIG. 6E shows two adjacent cells transfected with Cx43-T1 and displaying the typical perinuclear localized aggregation. FIG. 6F shows no dye passed between neighboring cells.

FIG. 8A shows the gel prior to Coomasie staining, which was imaged with excitation at 560 nm and emission at 610 nm. The tandem dimer tdimer2(12) has a small tetrameric component due a fraction of the covalent tandem pairs participating in intermolecular dimer pairs. Fluorescent proteins that are not boiled do not necessarily migrate at their expected molecular weight. FIG. 8B shows the same gel as in FIG. 8A after Coomasie staining. The band at ~20 kDa results from partial hydrolysis of the main chain acylimine linkage in protein containing a red chromophore.

In FIG. 9A, the quadrants corresponding to T1, dimer2, and mRFP1 all appear of similar brightness when excited at 540 nm and imaged with a 575 nm (long pass) emission filter. Almost no fluorescence is visible for identically treated *E. coli* transformed with DsRed. In FIG. 9B, when excited at 560 nm and imaged with a 610 (long pass) filter, mRFP1 appears brighter due to its 25 nm red shift. In FIG. 9C, the monomer mRFP1 does not contain a green fluorescent component and is thus very dim in comparison to T1 and dimer2 when excited at 470 nm, a wavelength suitable for excitation of EGFP. FIG. 9D shows a digital color photograph of the same plate taken after 5 days at room temperature reveals the orange and purple hues of T1 and mRFP 1, respectively.

FIGS. 10A–10B show a table describing the protocols and multiple libraries created during evolution of dimer1 and mRFP1, as well as other intermediate forms. The templates, method of mutagenesis, targeted positions within the DsRed polypeptide, and resulting clones are indicated.

FIGS. 11A–11D show a table providing a key to the primer pairs used in the mutagenesis protocols, as well as the target codon positions.

FIGS. 12A and 12B provide the PCR primer sequences listed in FIGS. 11A–11D.

FIG. 13 shows a table describing the results of a series of experiments testing the functionality of various DsRed chimeric molecules. The chimeric molecules comprise a DsRed sequence and the Cx43 polypeptide. The plasmids encoding the fusion polypeptides were transfected into HeLa cells, and the ability of the expressed fusion polypeptides to form functional gap junctions was assayed by the microinjection of lucifer yellow dye. Passage of the dye from one HeLa cell to an adjacent HeLa cell indicates the presence of a functional gap junction, and thus, a functional fusion polypeptide.

FIG. 14 shows various biophysical properties of wild-type DsRed, T1, dimer2, tdimer2(12), and mRFP1 polypeptides.

FIG. 15 shows a table providing excitation/emission wavelength values, relative maturation speed and red/green ratio values of red and green fluorescent protein species.

FIG. 16 shows the nucleotide sequence of the *Discosoma* sp. wild-type red fluorescent protein open reading frame (DsRed).

FIG. 17 shows the amino acid sequence of the *Discosoma* sp. wild-type red fluorescent protein (DsRed).

FIG. 18 shows the nucleotide sequence of the *Discosoma* sp. variant fast T1 red fluorescent protein.

FIG. 19 shows the amino acid sequence of the *Discosoma* sp. variant fast T1 red fluorescent protein.

FIG. 20 shows a table showing the amino acid substitutions identified during the construction of variant DsRed proteins. Also shown are the substitutions originally contained in the fast T1 DsRed variant.

FIG. 21 shows the nucleotide sequence of the *Discosoma* sp. variant red fluorescent protein dimer2 open reading frame.

FIG. 22 shows the amino acid sequence of the *Discosoma* sp. variant red fluorescent protein dimer2.

FIG. 23 shows the nucleotide sequence of the *Discosoma* sp. variant red fluorescent protein mRFP1 open reading frame.

FIG. 24 shows the amino acid sequence of the *Discosoma* sp. variant red fluorescent protein mRFP1.

FIG. 25 shows the nucleotide sequence of a modified *Discosoma* sp. wild type red fluorescent protein open reading frame with humanized codon usage.

FIG. 30 shows the amino acid sequence of mRFP1.1.

FIG. 31 shows the nucleotide sequence of mRFP1.1.

DETAILED DESCRIPTION OF THE INVENTION

Definitions

Figure 1:
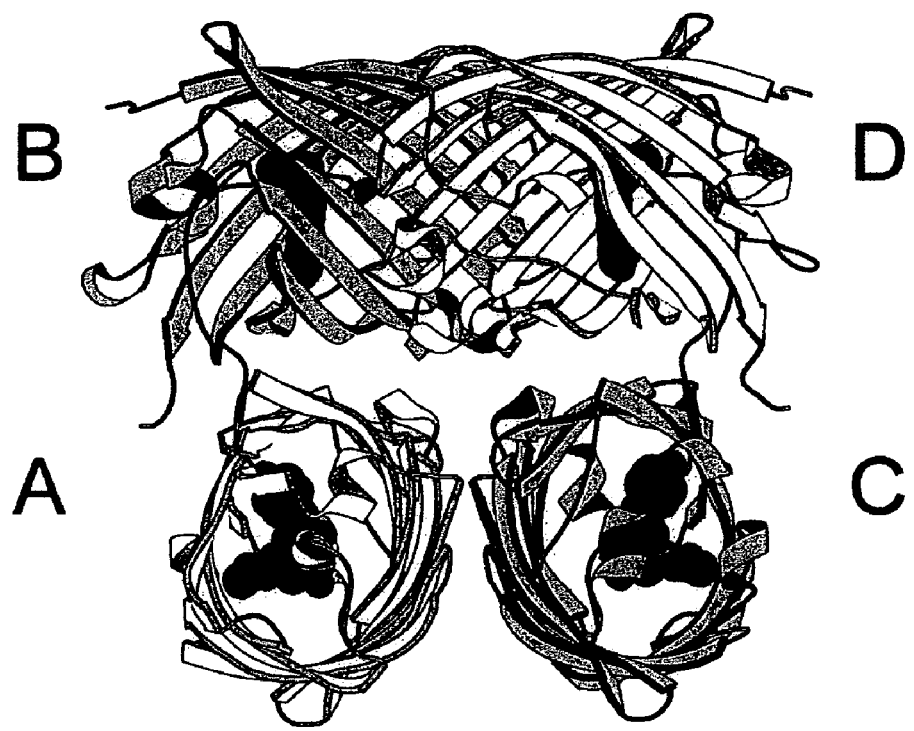
FIG. 1 illustrates the tetrameric form of DsRed (PDB identification code 1G7K). The A-C and B-D interfaces are equivalent, as are the A-B and C-D interfaces.

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice the present invention. For purposes of the present invention, the following terms are defined.

The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. It will be understood that when a nucleic acid molecule is represented by a DNA sequence, this also includes RNA molecules having the corresponding RNA sequence in which "U" (uridine) replaces "T" (thymidine).

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a fluorescent protein variant of the invention linked to a polypeptide of interest. The term "recombinant host cell" refers to a cell that contains a recombinant nucleic acid molecule. As such, a recombinant host cell can express a polypeptide from a "gene" that is not found within the native (non-recombinant) form of the cell.

Reference to a polynucleotide "encoding" a polypeptide means that, upon transcription of the polynucleotide and translation of the mRNA produced therefrom, a polypeptide is produced. The encoding polynucleotide is considered to include both the coding strand, whose nucleotide sequence is identical to an mRNA, as well as its complementary strand. It will be recognized that such an encoding polynucleotide is considered to include degenerate nucleotide sequences, which encode the same amino acid residues. Nucleotide sequences encoding a polypeptide can include polynucleotides containing introns as well as the encoding exons.

The term "expression control sequence" refers to a nucleotide sequence that regulates the transcription or translation of a polynucleotide or the localization of a polypeptide to which to which it is operatively linked. Expression control sequences are "operatively linked" when the expression control sequence controls or regulates the transcription and, as appropriate, translation of the nucleotide sequence (i.e., a transcription or translation regulatory element, respectively), or localization of an encoded polypeptide to a specific compartment of a cell. Thus, an expression control sequence can be a promoter, enhancer, transcription terminator, a start codon (ATG), a splicing signal for intron excision and maintenance of the correct reading frame, a STOP codon, a ribosome binding site, or a sequence that targets a polypeptide to a particular location, for example, a cell compartmentalization signal, which can target a polypeptide to the cytosol, nucleus, plasma membrane, endoplasmic reticulum, mitochondrial membrane or matrix, chloroplast membrane or lumen, medial trans-Golgi cisternae, or a lysosome or endosome. Cell compartmentalization domains are well known in the art and include, for example, a peptide containing amino acid residues 1 to 81 of human type II membrane-anchored protein galactosyltransferase, or amino acid residues 1 to 12 of the presequence of subunit IV of cytochrome c oxidase (see, also, Hancock et al., *EMBO J.* 10:4033–4039, 1991; Buss et al., *Mol. Cell. Biol.* 8:3960–3963, 1988; U.S. Pat. No. 5,776,689, each of which is incorporated herein by reference).

The term "operatively linked" or "operably linked" or "operatively joined" or the like, when used to describe chimeric proteins, refer to polypeptide sequences that are placed in a physical and functional relationship to each other. In a most preferred embodiment, the functions of the polypeptide components of the chimeric molecule are unchanged compared to the functional activities of the parts in isolation. For example, a fluorescent protein of the present invention can be fused to a polypeptide of interest. In this case, it is preferable that the fusion molecule retains its fluorescence, and the polypeptide of interest retains its original biological activity. In some embodiments of the present invention, the activities of either the fluorescent protein or the protein of interest can be reduced relative to their activities in isolation. Such fusions can also find use with the present invention. As used herein, the chimeric fusion molecules of the invention can be in a monomeric state, or in a multimeric state (e.g., dimeric).

In another example, the tandem dimer fluorescent protein variant of the invention comprises two "operatively linked" fluorescent protein units. The two units are linked in such a way that each maintains its fluorescence activity. The first and second units in the tandem dimer need not be identical. In another embodiment of this example, a third polypeptide of interest can be operatively linked to the tandem dimer, thereby forming a three part fusion protein.

The term "oligomer" refers to a complex formed by the specific interaction of two or more polypeptides. A "specific interaction" or "specific association" is one that is relatively stable under specified conditions, for example, physiologic conditions. Reference to a "propensity" of proteins to oligomerize indicates that the proteins can form dimers, trimers, tetramers, or the like under specified conditions. Generally, fluorescent proteins such as GFPs and DsRed have a propensity to oligomerize under physiologic conditions although, as disclosed herein, fluorescent proteins also can oligomerize, for example, under pH conditions other than physiologic conditions. The conditions under which fluorescent proteins oligomerize or have a propensity to oligomerize can be determined using well known methods as disclosed herein or otherwise known in the art.

As used herein, a molecule that has a "reduced propensity to oligomerize" is a molecule that shows a reduced propensity to form structures with multiple subunits in favor of forming structures with fewer subunits. Similarly, a molecule that has a "reduced propensity to tetramerize" or "has a reduce propensity to form tetramers" is a molecule that shows a reduced propensity to form structures with four subunits in favor ot forming structures with fewer subunits. A molecule that would normally form tetrameric structures under physiological conditions shows a reduced propensity to oligomerize (tetramerize) if the molecule is changed in such a way that it now has a preference to form monomers, dimers or trimers. A molecule that would normally form dimeric structures under physiological conditions shows a reduced propensity to oligomerize (dimerize) if the molecule is changed in such a way that it now has a preference to form monomers. Thus, "reduced propensity to oligomerize" applies equally to proteins that are normally dimers and to proteins that are normally tetrameric.

As used herein, the term "non-tetramerizing" refers to protein forms that produce trimers, dimers and monomers, but not tetramers. Similarly, "non-dimerizing" refers to protein forms that remain monomeric.

As used herein, the term "efficiency of (chromophore) maturation" with reference to a red fluorescent protein (RFP) indicates the percentage of the protein that has matured from a species with a green fluorescent protein (GFP)-like absorbance spectrum to the final RFP absorbance spectrum. Accordingly, efficiency of maturation is determined after allowing sufficient time for the maturation process to be practically (e.g.>95%) complete. Preferably, the resultant RFP, e.g. DsRed, will contain at least about 80%, more preferably at least about 85%, even more preferably at least about 90%, even more preferably at least about 95%, still more preferably at least about 98%, most preferably at least about 99% of the red fluorescent species.

As used herein, the term "brightness," with reference to a fluorescent protein, is measured as the product of the extinction coefficient (EC) at a given wavelenght and the fluorescence quantum yield (QY).

The term "probe" refers to a substance that specifically binds to another substance (a "target"). Probes include, for example, antibodies, polynucleotides, receptors and their ligands, and generally can be labeled so as to provide a means to identify or isolate a molecule to which the probe has specifically bound. The term "label" refers to a composition that is detectable with or without the instrumentation, for example, by visual inspection, spectroscopy, or a photochemical, biochemical, immunochemical or chemical reaction. Useful labels include, for example, phosphorus-32, a fluorescent dye, a fluorescent protein, an electron-dense reagent, an enzymes (such as is commonly used in an ELISA), a small molecule such as biotin, digoxigenin, or other haptens or peptide for which an antiserum or antibody, which can be a monoclonal antibody, is available. It will be recognized that a fluorescent protein variant of the invention, which is itself a detectable protein, can nevertheless be labeled so as to be detectable by a means other than its own fluorescence, for example, by incorporating a radionuclide label or a peptide tag into the protein so as to facilitate, for example, identification of the protein during its expression and isolation of the expressed protein, respectively. A label useful for purposes of the present invention generally generates a measurable signal such as a radioactive signal, fluorescent light, enzyme activity, and the like, either of which can be used, for example, to quantitate the amount of the fluorescent protein variant in a sample.

The term "nucleic acid probe" refers to a polynucleotide that binds to a specific nucleotide sequence or sub-sequence of a second (target) nucleic acid molecule. A nucleic acid probe generally is a polynucleotide that binds to the target nucleic acid molecule through complementary base pairing. It will be understood that a nucleic acid probe can specifically bind a target sequence that has less than complete complementarity with the probe sequence, and that the specificity of binding will depend, in part, upon the stringency of the hybridization conditions. A nucleic acid probes can be labeled as with a radionuclide, a chromophore, a lumiphore, a chromogen, a fluorescent protein, or a small molecule such as biotin, which itself can be bound, for example, by a streptavidin complex, thus providing a means to isolate the probe, including a target nucleic acid molecule specifically bound by the probe. By assaying for the presence or absence of the probe, one can detect the presence or absence of the target sequence or sub-sequence. The term "labeled nucleic acid probe" refers to a nucleic acid probe that is bound, either directly or through a linker molecule, and covalently or through a stable non-covalent bond such as an ionic, van der Waals or hydrogen bond, to a label such that the presence of the probe can be identified by detecting the presence of the label bound to the probe.

The term "polypeptide" or "protein" refers to a polymer of two or more amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence encoding the amino acid sequence of the protein from a recombinant DNA molecule.

The term "isolated" or "purified" refers to a material that is substantially or essentially free from components that normally accompany the material in its native state in nature.

Purity or homogeneity generally are determined using analytical chemistry techniques such as polyacrylamide gel electrophoresis, high performance liquid chromatography, and the like. A polynucleotide or a polypeptide is considered to be isolated when it is the predominant species present in a preparation. Generally, an isolated protein or nucleic acid molecule represents greater than 80% of the macromolecular species present in a preparation, often represents greater than 90% of all macromolecular species present, usually represents greater than 95%, of the macromolecular species, and, in particular, is a polypeptide or polynucleotide that purified to essential homogeneity such that it is the only species detected when examined using conventional methods for determining purity of such a molecule.

The term "naturally-occurring" is used to refer to a protein, nucleic acid molecule, cell, or other material that occurs in nature. For example, a polypeptide or polynucleotide sequence that is present in an organism, including in a virus. A naturally occurring material can be in its form as it exists in nature, and can be modified by the hand of man such that, for example, is in an isolated form.

The term "antibody" refers to a polypeptide substantially encoded by an immunoglobulin gene or immunoglobulin genes, or antigen-binding fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist as intact immunoglobulins and as well characterized antigen-binding fragments of an antibody, which can be produced by digestion with a peptidase or can using recombinant DNA methods. Such antigen-binding fragments of an antibody include, for example, Fv, Fab' and F(ab)'$_2$ fragments. The term "antibody," as used herein, includes antibody fragments either produced by the modification of whole antibodies or those synthesized de novo using recombinant DNA methodologies. The term "immunoassay" refers to an assay that utilizes an antibody to specifically bind an analyte. An immunoassay is characterized by the use of specific binding properties of a particular antibody to isolate, target, and/or quantify the analyte.

The term "identical," when used in reference to two or more polynucleotide sequences or two or more polypeptide sequences, refers to the residues in the sequences that are the same when aligned for maximum correspondence. When percentage of sequence identity is used in reference to a polypeptide, it is recognized that one or more residue positions that are not otherwise identical can differ by a conservative amino acid substitution, in which a first amino acid residue is substituted for another amino acid residue having similar chemical properties such as a similar charge or hydrophobic or hydrophilic character and, therefore, does not change the functional properties of the polypeptide. Where polypeptide sequences differ in conservative substitutions, the percent sequence identity can be adjusted upwards to correct for the conservative nature of the substitution. Such an adjustment can be made using well known methods, for example, scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated using any well known algorithm (see, for example, Meyers and Miller, *Comp. Appl. Biol. Sci.* 4:11–17, 1988; Smith and Waterman, *Adv. Appl. Math.* 2:482, 1981; Needleman and Wunsch, *J. Mol. Biol.* 48:443, 1970; Pearson and Lipman, *Proc. Natl. Acad. Sci., USA* 85:2444 (1988); Higgins and Sharp, *Gene* 73:237–244, 1988; Higgins and Sharp, *CABIOS* 5:151–153; 1989; Corpet et al., *Nucl. Acids Res.* 16:10881–10890, 1988; Huang, et al., *Comp. Appl. Biol. Sci.* 8:155–165, 1992; Pearson et al., *Meth. Mol. Biol.*, 24:307–331, 1994). Alignment also can be performed by simple visual inspection and manual alignment of sequences.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a fluorescent protein variant also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein. Furthermore, it will be recognized that individual substitutions, deletions or additions that alter, add or delete a single amino acid or a small percentage of amino acids (typically less than 5%, and generally less than 1%) in an encoded sequence can be considered conservatively modified variations, provided alteration results in the substitution of an amino acid with a chemically similar amino acid. Conservative amino acid substitutions providing functionally similar amino acids are well known in the art, including the following six groups, each of which contains amino acids that are considered conservative substitutes for each another:

1) Alanine (Ala, A), Serine (Ser, S), Threonine (Thr, T);
2) Aspartic acid (Asp, D), Glutamic acid (Glu, E);
3) Asparagine (Asn, N), Glutamine (Gln, Q);
4) Arginine (Arg, R), Lysine (Lys, K);
5) Isoleucine (Ile, I), Leucine (Leu, L), Methionine (Met, M), Valine (Val, V); and
6) Phenylalanine (Phe, F), Tyrosine (Tyr, Y), Tryptophan (Trp, W).

Two or more amino acid sequences or two or more nucleotide sequences are considered to be "substantially identical" or "substantially similar" if the amino acid sequences or the nucleotide sequences share at least 80% sequence identity with each other, or with a reference sequence over a given comparison window. Thus, substantially similar sequences include those having, for example, at least 85% sequence identity, at least 90% sequence identity, at least 95% sequence identity, or at least 99% sequence identity.

A subject nucleotide sequence is considered "substantially complementary" to a reference nucleotide sequence if the complement of the subject nucleotide sequence is substantially identical to the reference nucleotide sequence. The term "stringent conditions" refers to a temperature and ionic conditions used in a nucleic acid hybridization reaction. Stringent conditions are sequence dependent and are different under different environmental parameters. Generally, stringent conditions are selected to be about 5° C. to 20° C. lower than the thermal melting point (Tm) for the specific sequence at a defined ionic strength and pH. The Tm is the temperature, under defined ionic strength and pH, at which 50% of the target sequence hybridizes to a perfectly matched probe.

The term "allelic variants" refers to polymorphic forms of a gene at a particular genetic locus, as well as cDNAs derived from mRNA transcripts of the genes, and the polypeptides encoded by them. The term "preferred mammalian codon" refers to the subset of codons from among the set of codons encoding an amino acid that are most frequently used in proteins expressed in mammalian cells as chosen from the following list: Gly (GGC, GGG); Glu (GAG); Asp (GAC); Val (GUG, GUC); Ala (GCC, GCU); Ser (AGC, UCC); Lys (AAG); Asn (AAC); Met (AUG); Ile (AUC); Thr (ACC); Trp (UGG); Cys (UGC); Tyr (UAU, UAC); Leu (CUG); Phe (UUC); Arg (CGC, AGG, AGA); Gin (CAG); His (CAC); and Pro (CCC).

Fluorescent molecules are useful in fluorescence resonance energy transfer, FRET, which involves a donor molecule and an acceptor molecule. To optimize the efficiency and detectability of FRET between a donor and acceptor molecule, several factors need to be balanced. The emission spectrum of the donor should overlap as much as possible with the excitation spectrum of the acceptor to maximize the overlap integral. Also, the quantum yield of the donor moiety and the extinction coefficient of the acceptor should be as high as possible to maximize $R_O$, which represents the distance at which energy transfer efficiency is 50%. However, the excitation spectra of the donor and acceptor should overlap as little as possible so that a wavelength region can be found at which the donor can be excited efficiently without directly exciting the acceptor because fluorescence arising from direct excitation of the acceptor can be difficult to distinguish from fluorescence arising from FRET. Similarly, the emission spectra of the donor and acceptor should overlap as little as possible so that the two emissions can be clearly distinguished. High fluorescence quantum yield of the acceptor moiety is desirable if the emission from the acceptor is to be measured either as the sole readout or as part of an emission ratio. One factor to be considered in choosing the donor and acceptor pair is the efficiency of fluorescence resonance energy transfer between them. Preferably, the efficiency of FRET between the donor and acceptor is at least 10%, more preferably at least 50% and even more preferably at least 80%.

The term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between wild type Aequorea GFP and a spectral variant, or a mutant thereof, is useful. A measurable difference can be determined by determining the amount of any quantitative fluorescent property, e.g., the amount of fluorescence at a particular wavelength, or the integral of fluorescence over the emission spectrum. Determining ratios of excitation amplitude or emission amplitude at two different wavelengths ("excitation amplitude ratioing" and "emission amplitude ratioing", respectively) are particularly advantageous because the ratioing process provides an internal reference and cancels out variations in the absolute brightness of the excitation source, the sensitivity of the detector, and light scattering or quenching by the sample.

As used herein, the term "fluorescent protein" refers to any protein that can fluoresce when excited with an appropriate electromagnetic radiation, except that chemically tagged proteins, wherein the fluorescence is due to the chemical tag, and polypeptides that fluoresce only due to the presence of certain amino acids such as tryptophan or tyrosine, whose emission peaks at ultraviolet wavelengths (i.e., less that about 400 nm) are not considered fluorescent proteins for purposes of the present invention. In general, a fluorescent protein useful for preparing a composition of the invention or for use in a method of the invention is a protein that derives its fluorescence from autocatalytically forming a chromophore. A fluorescent protein can contain amino acid sequences that are naturally occurring or that have been engineered (i.e., variants or mutants). When used in reference to a fluorescent protein, the term "mutant" or "variant" refers to a protein that is different from a reference protein. For example, a spectral variant of Aequorea GFP can be derived from the naturally occurring GFP by engineering mutations such as amino acid substitutions into the reference GFP protein. For example ECFP is a spectral variant of GFP that contains substitutions with respect to GFP (compare SEQ ID NOS: 10 and 11).

Many cnidarians use green fluorescent proteins as energy transfer acceptors in bioluminescence. The term "green fluorescent protein" is used broadly herein to refer to a protein that fluoresces green light, for example, Aequorea GFP (SEQ ID NO: 10). GFPs have been isolated from the Pacific Northwest jellyfish, Aequorea Victoria, the sea pansy, Renilla reniformis, and Phialidium gregarium (Ward et al., Photochem. Photobiol. 35:803–808, 1982; Levine et al., Comp. Biochem. Physiol. 72B:77–85, 1982, each of which is incorporated herein by reference). Similarly, reference is made herein to "red fluorescent proteins", which fluoresce red, "cyan fluorescent proteins," which fluoresce cyan, and the like. RFPs, for example, have been isolated from the corallimorph Discosoma (Matz et al., Nature Biotechnology 17:969–973 [1999]). The term "red fluorescent protein," or "RFP" is used in the broadest sense and specifically covers the Discosoma RFP (DsRed), and red fluorescent proteins from any other species, such as coral and sea anemone, as well as variants thereof as long as they retain the ability to fluoresce red light.

The term "coral" as used herein encompasses species within the class Anthozoa, and includes specifically both corals and corallimorphs.

A variety of Aequorea GFP-related fluorescent proteins having useful excitation and emission spectra have been engineered by modifying the amino acid sequence of a naturally occurring GFP from A. victoria (see Prasher et al., Gene 111:229–233, 1992; Heim et al., Proc. Natl. Acad. Sci. USA 91:12501–12504, 1994; U.S. Pat. No. 5,625,048; International application PCT/US95/14692, now published PCT WO96/23810, each of which is incorporated herein by reference). As used herein, reference to a "related fluorescent protein" refers to a fluorescent protein that has a substantially identical amino acid sequence when compared to a reference fluorescent protein. In general, a related fluorescent protein, when compared to the reference fluorescent protein sequence, has a contiguous sequence of at least about 150 amino acids that shares at least about 85% sequence identity with the reference fluorescent protein, and particularly has a contiguous sequence of at least about 200 amino acids that shares at least about 95% sequence identity with the reference fluorescent protein. Thus, reference is made herein to an "Aequorea-related fluorescent protein" or to a "GFP-related fluorescent protein," which is exemplified by the various spectral variants and GFP mutants that have amino acid sequences that are substantially identical to A. victoria GFP (SEQ ID NO: 10), to a "Discosoma-related fluorescent protein" or a "DsRed-related fluorescent related protein," which is exemplified by the various mutants that have amino acid sequences substantially identical to that of DsRed (SEQ ID NO: 1), and the like, for example, a Renilla-related fluorescent protein or a Phialidium-related fluorescent protein.

The term "mutant" or "variant" also is used herein in reference to a fluorescent protein that contains a mutation with respect to a corresponding wild type fluorescent protein. In addition, reference is made herein to a "spectral variant" or "spectral mutant" of a fluorescent protein to indicate a mutant fluorescent protein that has a different fluorescence characteristic with respect to the corresponding wild type fluorescent protein. For example, CFP, YFP, ECFP (SEQ ID NO: 11), EYFP-V68L/Q69K (SEQ ID NO: 12), and the like are GFP spectral variants.

Aequorea GFP-related fluorescent proteins include, for example, wild type (native) Aequorea victoria GFP (Prasher et al., supra, 1992; see, also, SEQ ID NO: 10), allelic variants of SEQ ID NO: 10, for example, a variant having a Q80R substitution (Chalfie et al., Science 263:802–805, 1994, which is incorporated herein by reference); and spectral variants of GFP such as CFP, YFP, and enhanced and otherwise modified forms thereof (U.S. Pat. Nos. 6,150,176; 6,124,128; 6,077,707; 6,066,476; 5,998,204; and 5,777,079, each of which is incorporated herein by reference), including GFP-related fluorescent proteins having one or more folding mutations, and fragments of the proteins that are fluorescent, for example, an A. victoria GFP from which the two N-terminal amino acid residues have been removed. Several of these fluorescent proteins contain different aromatic amino acids within the central chromophore and fluoresce at a distinctly shorter wavelength than the wild type GFP species. For example, the engineered GFP proteins designated P4 and P4-3 contain, in addition to other mutations, the substitution Y66H; and the engineered GFP proteins designated W2 and W7 contain, in addition to other mutations, Y66W.

The term "non-tetramerizing fluorescent protein" is used broadly herein to refer to normally tetrameric fluorescent proteins that have been modified such that they have a reduced propensity to tetramerize as compared to a corresponding unmodified fluorescent protein. As such, unless specifically indicated otherwise, the term "non-tetramerizing fluorescent protein" encompasses dimeric fluorescent proteins, tandem dimer fluorescent proteins, as well as fluorescent proteins that remain monomeric.

As used herein, the term "aggregation" refers to the tendency of an expressed protein to form insoluble precipitates or visible punctae and is to be distinguished from "oligomerization". In particular, mutations that reduce aggregation, e.g., increase the solubility of the protein, do not necessarily reduce oligomerization, i.e., convert tetramers to dimers or monomers.

DESCRIPTION OF THE PREFERRED EMBODIMENTS

The cloning of a red fluorescent protein from Discosoma (DsRed) raised a great deal of interest due to its tremendous potential as a tool for the advancement of cell biology. However, a careful investigation of the properties of this protein revealed several problems that would preclude DsRed from being as widely accepted as the Aequorea GFP and its blue, cyan, and yellow variants, which have found widespread use as both genetically encoded indicators for tracking gene expression and as donor/acceptor pairs for fluorescence resonance energy transfer (FRET). Extending the spectrum of available colors to red wavelengths would provide a distinct new label for multicolor tracking of fusion proteins and together with GFP would provide a new FRET donor/acceptor pair that would be superior to the currently preferred cyan/yellow pair.

The three most pressing problems with the 28 kDa DsRed are its strong tendency to oligomerize, its slow maturation, and its inefficient maturation from a species with a GFP-like spectrum to the ultimate RFP spectrum.

A variety of techniques have been used to determine that DsRed is an obligate tetramer both in vitro and in vivo. For numerous reasons, the oligomeric state of DsRed is problematic for applications in which it is fused to a protein of interest in order to monitor trafficking or interactions of the latter. Using purified protein, it was shown that DsRed requires greater than 48 hours to reach >90% of its maximal red fluorescence (see below). During the maturation process, a green intermediate initially accumulates and is slowly converted to the final red form. However, the conversion of the green component does not proceed to completion and thus a fraction of aged DsRed remains green. The primary disadvantage of the incomplete maturation is an excitation spectrum that extends well into the green wavelengths due to energy transfer between the green and red species within the tetramer. This is a particularly serious problem due to overlap with the excitation spectra of potential FRET partners such as GFP.

The original report of the cloning of DsRed provided an in vivo application marking the fates of Xenopus blastomeres after 1 week of development (Matz et al., Nature Biotechnology 17:969–973 [1999]). As disclosed herein, DsRed has been characterized with respect to the time the red fluorescence takes to appear, the pH sensitivity of the chromophore, how strongly the chromophore absorbs light and fluoresces, how readily the protein photobleaches, and whether the protein normally exists as a monomer or an oligomer in solution. The results demonstrate that DsRed provides a useful complement to or alternative for GFP and its spectral mutants. In addition, DsRed mutants that are non-fluorescent or that are blocked or slowed in converting from green to red emission were characterized, including mutants in which the eventual fluorescence is substantially red-shifted from wild type DsRed (see, Baird et al., Proc. Natl. Acad. Sci., USA 97:11984–11989, 2000; Gross et al., Proc. Natl. Acad. Sci., USA 97:11990–11995, 2000, each of which is incorporated herein by reference).

Red Fluorescent Protein Variants with Improved Efficacy of Maturation

The present invention provides RFP variants that show more efficient chomophore maturation than a reference wild-type or variant RFP, as a result of at least one amino acid alteration within the reference (wild-type or variant) sequence.

The wild-type RFP protein typically consists of about 70% red protein with about 30% contamination by the green, immature form of the protein. Through careful mass spectrometric and biochemical investigations, it has been determined that the Cα-N bond of Q66 in DsRed is oxidized as the protein matures into its red form, which, in turn, led to a further investigation of the role of the amino acid at position 66 as it relates to chromophore maturation. By site-directed mutagenesis, it was determined that the substitution of methionine (M) for the native glutamine (Q) at amino acid position 66 yielded a protein that showed a deeper pink color than the wild-type protein, and contained less of the immature green form than wild-type DsRed. In addition, the Q66M DsRed variant was found to mature more quickly than wild-type DsRed. Additional experiments have shown that the Q66M mutation retained its advantageous properties also when introduced into non-tetramerizing, i.e. dimeric or monomeric DsRed variants, which contained additional mutations. Further details of these findings are set forth in the Examples below. Thus, an RFP variant of the invention can be derived from a naturally occurring (wild-type) RFP or from a spectral variant or mutant thereof, and contains at least one mutation that makes chromophore maturation more efficient.

While the invention is illustrated with reference to the Q66M mutation in DsRed, it will be understood that it is not so limited. Mutations of other amino acids within the wild-type DsRed sequence that play a role in chromophore structure, orientation and/or maturation can also yield DsRed variants with improved maturation efficiency. Similarly, amino acid alterations (e.g. substitutions) at corresponding (homologous) positions or regions in other RFPs can produce RFP variants showing an improvement in maturation efficiency. All of such variants, alone or in combination with other mutations (substitutions, insertions and/or deletions) within the wild-type RFP sequence, are specifically within the scope of the invention. Thus an additionall exemplary amino acid alteration that is believed to improve maturation of both the wild-type DsRed protein and DsRed variants, including Q66M DsRed is a substitution at amino acid position 147 of wild-type DsRed. A preferred substitution at this position is T147S, but other substitutions resulting in similar improvements in spectral properties and, in particular, in the efficiency and potentially speed of maturation, are also possible. Especially, substitution of amino acids with similar properties of threonine (T) are expected to yield such variants.

In a specific embodiment, the invention concerns RFP variants with improved maturation efficiency that have a reduced propensity to tetramerize, as a result of one or more further mutations within the RFP molecule. In particular, in this embodiment, the invention concerns non-tetramerizing, such as dimeric or monomeric, DsRed variants that show enhanced maturation efficiency relative to the corresponding non-tetramerizing DsRed variant. Further details about the design and preparation of such variants are provided below.

In brief, the RFP variants of the invention can be derived from RFPs that have a propensity to dimerize or tetramerize. As disclosed herein, an RFP variant of the invention can be derived from a naturally occurring RFP or from a spectral variant or mutant thereof, and contains at least one mutation that enhances maturation efficiency, and optionally at least one additional mutation that reduces or eliminates the propensity of the RFP to oligomerize.

A fluorescent protein variant of the invention can be derived from any red fluorescent protein that is known to oligomerize, including, for example, *Discosoma* RFP (SEQ ID NO: 1); or a fluorescent protein related to an RFP, such as a DsRed variant in any other species, or a mutant or variant of such fluorescent proteins.

In one embodiment, the propensity of the red fluorescent protein variant of the invention to oligomerize is reduced or eliminated. There are two basic approaches to reduce the propensity of the red fluorescent protein (RFP), such as DsRed, to form intermolecular oligomers, (1) oligomerization can be reduced or eliminated, by introducing mutations into appropriate regions of the fluorescent protein, e.g., an RFP molecule, and (2) two subunits of the fluorescent protein can operatively link, e.g., link RFP to each other by a linker, such as a peptide linker. If oligomerization is reduced or eliminated by following approach (1), it is usually necessary to introduce additional mutations into the molecule, in order to restore fluorescence, which is typically lost or greatly impaired as a result of introducing mutations at the oligomer interfaces.

Red Fluorescent Protein Variants with Reduced Propensity to Oligomerize

The present invention provides fluorescent protein variants where the degree of oligomerization of the fluorescent protein is reduced or eliminated by the introduction of amino acid substitutions to reduce or abolish the propensity of the constituent monomers to tetramerize. In one embodiment, the resulting structures have a propensity to dimerize. In other embodiments, the resulting structures have a propensity to remain monomeric.

Various dimer forms can be created. For example, an AB orientation dimer can be formed, or alternatively, an AC orientation dimer can be formed. However, with the creation of dimeric forms, fluorescence or the rate of maturation of fluorescence, can be lost. The present invention provides methods for the generation of dimeric forms that display detectable fluorescence, and furthermore, fluorescence that has advantageous rates of maturation.

In one embodiment, the dimer is an intermolecular dimer. Furthermore, the dimer can be a homodimer (comprising two molecules of the identical species) or a heterodimer (comprising two molecules of different species). In a preferred embodiment, dimers will spontaneously form in physiological conditions. As used herein, the molecules that form such types of structures are said to have a reduced tendency to oligomerize, as the monomeric units have reduced or non-existent ability to form tetrameric intermolecular oligomers.

A non-limiting, illustrative example of such a dimeric red fluorescent protein variant is described herein, and is termed "dimer2." The dimer2 nucleotide sequence is provided in SEQ ID NO: 7 and FIG. 21. The dimer2 polypeptide is provided in SEQ ID NO: 6 and FIG. 22.

In an attempt to produce a still further advantageous form of the DsRed variant dimer, a novel strategy to synthesize a "tandem" DsRed variant dimer was devised. This approach utilized covalent tethering of two engineered monomeric DsRed units to yield a dimeric form of DsRed with advantageous properties. The basic strategy was to fuse two copies of an AC dimer with a polypeptide linker such that the critical dimer interactions could be satisfied through intramolecular contacts with the tandem partner encoded within the same polypeptide. Such operably linked homodimers or heterodimers are referred to herein as "tandem dimers," and have a substantially reduced propensity to form tetrameric structures.

Illustrative examples of such tandem red fluorescent protein variant dimers include, without limitation, two monomeric units of the dimer2 species (SEQ ID NO: 6) operably covalently linked by a peptide linker, preferably about 9 to about 25, more preferably about 9 to 20 amino acid residues in length. Such linkers finding use with the invention include, but are not limited to, for example, the 9 residue linker RMGTGSGQL (SEQ ID NO: 16), the 12 residue linker GHGTGSTGSGSS (SEQ ID NO: 17), the 13 residue linker RMGSTSGSTKGQL (SEQ ID NO: 18), or the 22 residue linker RMGSTSGSGKPGSGEGSTKGQL (SEQ ID NO: 19). As noted above, the subunits of such tandem dimers preferably contain mutations relative to the wild-type DsRed sequence of SEQ ID NO: 1, in order to preserve/restore fluorescent properties. An illustrative example of the tandem red fluorescent protein dimers herein is a dimer composed of two monomers, wherein at least one of the monomers is a variant DsRed, which has an amino acid sequence of SEQ ID NO: 6, operatively linked by a peptide linker, preferably about 9 to about 25, more preferably about 10 to about 20 amino acid residues in length, including any of the 9, 12, 13, and 22 residue linkers above. Yet another illustrative example of a tandem red fluorescent protein dimer herein is a tandem dimer composed of two identical or different DsRed variant monomeric subunits at least one of which contains the following substitutions within the DsRed polypeptide of SEQ ID NO: 1: N42Q, V44A, V71A, F118L, K163Q, S179T, S197T, T217S (mutations internal to the β-barrel); R2A, K5E and N6D (aggregation reducing mutations); I125R and V127T (AB interface mutations); and T21S, H41T, C117T and S131P (miscellaneous surface mutations). Just as in the other illustrative dimers, the two monomeric subunits may be fused by a peptide linker, preferably about 9 to about 25, more preferably about 10 to about 25 amino acid residues in length, such as any of the 9, 12, 13, and 22 residue linkers above. Shorter linkers are generally preferable to longer linkers, as long as they do not significantly slow affinity maturation or otherwise interfere with the fluorescent and spectral properties of the dimer. As noted above, the two monomeric subunits within a dimer may be identical or different. Thus, for example, one subunit may be the wild-type DsRed monomer of SEQ ID NO: 1 operatively linked to a variant DsRed polypeptide, such as any of the DsRed variants listed above or otherwise disclosed herein. The monomers should be linked such that the critical dimer interactions are satisfied through intramolecular contacts with the tandem partner. The peptide linkers are preferably protease resistant. The peptide linkers specifically disclosed herein are only illustrative. One skilled in the art will understand that other peptide linkers, preferably protease resistant linkers, are also suitable for the purpose of the present invention. See, e.g., Whitlow et al., *Protein Eng* 6:989–995 (1993).

In one embodiment, disclosed in more detail in the examples below, a novel approach was used to overcome the intermolecular oligomerization propensity of wild-type DsRed by linking the C-terminus of the A subunit to the N-terminus of the B subunit through a flexible linker to produce tandem dimers. Based on the crystal structure of DsRed tetramer, a 10 to 20 residue linkers, such as an 18 residue linker (Whitlow et al., *Prot. Eng.* 6:989–995, 1993, supra, which is incorporated herein by reference) was predicted to be long enough to extend from the C-terminus of the A subunit to the N-terminus of the C subunit (about 30 Å), but not to the N-terminus of the B subunit (greater than 70 Å). As such, 'oligomerization' in the tandem dimers is intramolecular, i.e., the tandem dimer of DsRed (tDsRed), for example, is encoded by a single polypeptide chain.

Furthermore, a combination of tDsRed with the I125R mutant (tDsRed-I125R) resulted in another dimeric red fluorescent protein. It should be recognized that this strategy can be generally applied to any protein system in which the distance between the N-terminus of one protein and the C-terminus of a dimer partner is known, such that a linker having the appropriate length can be used to operatively link the monomers. In particular, this strategy can be useful for other modifying other fluorescent proteins that have interesting spectral properties, but form obligate dimers that are difficult to disrupt using the targeted mutagenesis method disclosed herein.

Mutagenesis Strategy to Produce Dimeric and Monomeric Red Fluorescent Proteins

The present invention provides variant fluorescent proteins that have a reduced propensity to form tetrameric oligomers (i.e., the propensity to form tetramers is reduced or eliminated) due to the presence of one or more mutations in the fluorescent protein. As disclosed herein, mutations were introduced into DsRed, and DsRed mutants having reduced oligomerization activity were identified, including, for example, a DsRed-I125R mutant of DsRed of SEQ ID NO: 20. The strategy for producing the DsRed mutants involved introducing mutations in DsRed that were predicted to interfere with the dimer interfaces (A-B or A-C, see FIGS. 1 and 2) and thus prevent formation of the tetramer. This strategy resulted in the production of DsRed mutants that had a reduced propensity to form tetramers by disrupting the A-B interface, for example, using the single replacement of isoleucine 125 with an arginine (I125R).

The basic strategy for decreasing the oligomeric state of DsRed was to replace key dimer interface residues with charged amino acids, preferably arginine. It is contemplated that dimer formation would require the targeted residue to interact with the identical residue of the dimer partner through symmetry. The resulting high energetic cost of placing two positive charges in close proximity should disrupt the interaction. Initial attempts to break apart the DsRed AC interface (see FIG. 2A) with the single mutations T147R, H162R, and F224R, consistently gave non-fluorescent proteins. The AB interface however, proved somewhat less resilient and could be broken with the single mutation I125R to give a poorly red fluorescent dimer that suffered from an increased green component and required more than 10 days to fully mature.

Illustrative examples of mutations (amino acid substitutions) which can further improve the fluorescent properties of I125R include mutations in at least one of amino acid positions 163, 179 an 217 within SEQ ID NO: 1. In a preferred embodiment, the I125R variant comprises at least one of the K163Q/M, S179T and T217S substitutions. Further illustrative variants may contain additional mutations at position N42 and/or C44 within SEQ ID NO: 1. Yet another group of illustrative DsRed dimers comprise additional mutations at at least one of residues I161 and S197 within SEQ ID NO: 1. Specific examples of DsRed variants obtained by this mutagenesis approach include DsRed-I125R, S179T, T217A, and DsRed-I125R, K163Q, T217A.

Figure 2A:
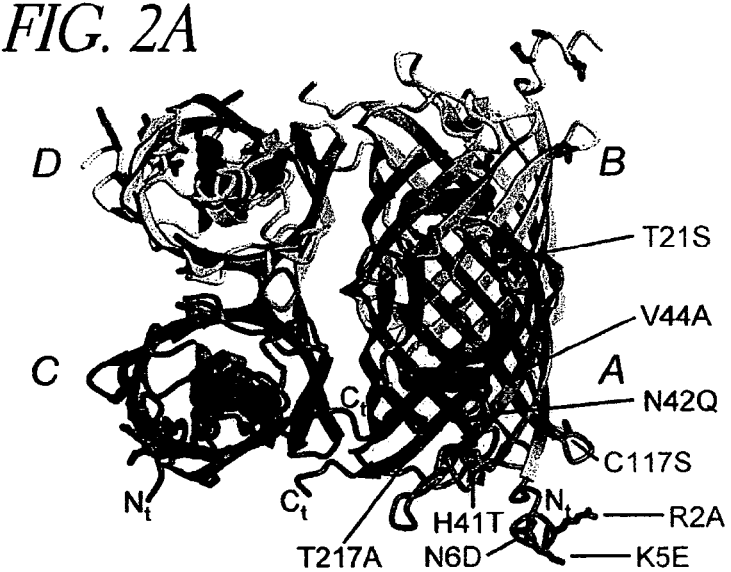
FIGS. 2A–2C show graphical representations of the tetramer, dimer and monomer forms of DsRed, respectively, based on the x-ray crystal structure of DsRed. Residues 1–5 were not observed in the crystal structure but have been arbitrarily appended for the sake of completeness. The DsRed chromophore is represented in red and the four chains of the tetramer are labeled following the convention of Yarbrough et al. (Yarbrough et al., *Proc. Natl. Acad. Sci. USA* 98:462–467 [2001]).

It is noted that there exists an inconsistency in the naming convention of the DsRed subunits in the prior art. As shown in FIG. 1, one convention assigns the A-B-C-D subunits as shown. However, a different convention is also recognized, which is shown in FIG. 2. When viewing the model of FIG. 1, the AC interface of that figure is equivalent to the AB interface shown in FIG. 2A. With the exception of FIG. 1, reference to subunit interfaces in the present application is according to the convention used in FIG. 2.

A similar directed mutagenesis strategy starting from T1-I125R (see FIG. 10A, library D1) was undertaken and eventually identified dimer1. Dimer1 was somewhat better than wt DsRed both in terms of brightness and rate of maturation but had a substantial green peak equivalent to that of T1. Dimer1 was also somewhat blue-shifted with an excitation maximum at 551 nm and an emission maximum at 579 nm. Error prone PCR on dimer1 (FIG. 10A, library D2) resulted in the discovery of dimer1.02 containing the mutation V71A in the hydrophobic core of the protein and effectively no green component in the excitation spectra. A second round of random mutagenesis (FIG. 10A, library D3) identified the mutations K70R which further decreased the green excitation, S197A which red-shifted the dimer back to DsRed wavelengths and T217S which greatly improved the rate of maturation. Unfortunately, K70R and S197A matured relatively slowly and T217S had a green excitation peak equivalent to DsRed. Using dimer1.02 as the template, two more rounds of directed mutagenesis were performed; the first focusing on the three positions identified above (FIG. 11A, library D3) and the second on C117, F118, F124, and V127 (FIG. 10A, library D4).

Figure 2B:
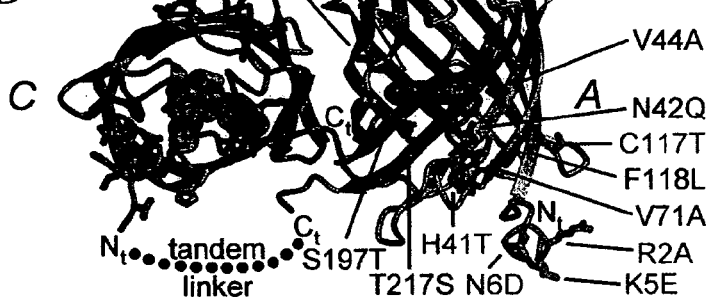
Figure 2C:
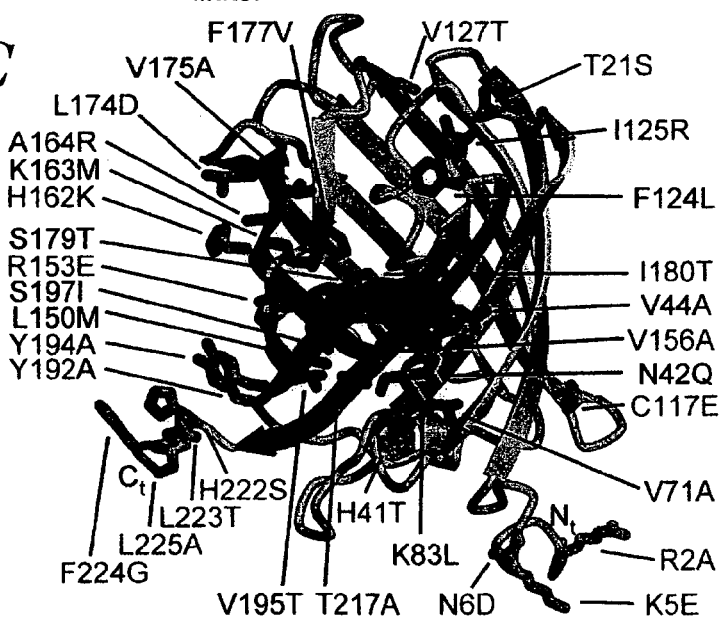

Continuing with the directed evolution strategy for a total of 4 generations, an optimal dimeric variant was produced, which was designated dimer2 (illustrated in FIG. 2B). This variant contains 17 mutations, of which eight are internal to the P-barrel (N42Q, V44A, V71A, F118L, K163Q, S179T, S197T and T217S), three are the aggregation reducing mutations found in T1 (R2A, K5E and N6D and see Bevis and Glick, *Nat. Biotechnol*, 20:83–87 [2002]; and Yanushevich et al., *FEBS Lett.*, 511:11–14 [2002]), two are AB interface mutations (I125R and V127T), and 4 are miscellaneous surface mutations (T21S, H41T, C117T and S131 P). The dimer2 nucleotide sequence is provided in SEQ ID NO: 7 and FIG. 21. The dimer2 polypeptide is provided in SEQ ID NO: 6 and FIG. 22.

The ultimate product of the mutagenesis approach described herein is a monomeric red fluorescent protein, designated mRFP1, which contains the following mutations within the wild-type DsRed sequence of SEQ ID NO: 1: N42Q, V44A, V71A, K83L, F124L, L150M, K163M, V175A, F177V, S179T, V195T, S197I, T217A, R2A, K5E, N6D, I125R, V127T, I180T, R153E, H162K, A164R, L174D, Y192A, Y194K, H222S, L223T, F224G, L225A, T21S, H41T, C117E, and V156A. Of these, the first 13 mutations are internal to the β-barrel. Of the remaining 20 external mutations, 3 are aggregation reducing mutations (R2A, K5E, and N6D), 3 are AB interface mutations (I125R, V127T, and I180T), 10 are AC interface mutations (R153E, H162K, A164R, L174D, Y192A, Y194K, H222S, L223T, F224G, and L225A), and 4 are additional beneficial mutations (T21S, H41T, C117E, and V156A). The mRFP1 nucleotide sequence is provided in SEQ ID NO: 9 and FIG. 23. The mRFP1 polypeptide is provided in SEQ ID NO: 8 and FIG. 24.

Although mRFP1 is believed to be optimized in many aspects, a person skilled in the art will appreciate that other mutations within these and other regions of the wild-type DsRed amino acid sequence (SEQ ID NO: 1) may also yield monomeric DsRed variants retaining the qualitative red fluorescing properties of the wild-type DsRed protein. Accordingly, mRFP1 serves merely as an illustration, and to invention is by no means intended to be limited to this particular monomer.

Specifically, the monomeric DsRed variants herein, e.g. mRFP1, can be further modified to alter the spectral and/or fluorescent properties of DsRed. For example, based upon experience with GFP, it is known that in the excited state, electron density tends to shift from the phenolate towards the carbonyl end of the chromophore. Therefore, placement of increasing positive charge near the carbonyl end of the chromophore tends to decrease the energy of the excited state and cause a red-shift in the absorbance and emission wavelength maximum of the protein. Decreasing a positive charge near the carbonyl end of the chromophore tends to have the opposite effect, causing a blue-shift in the protein's wavelengths. Similarly, mutations have been introduced into DsRed to produce mutants having altered fluorescence characteristics.

Amino acids with charged (ionized D, E, K, and R), dipolar (H, N, Q, S, T, and uncharged D, E and K), and polarizable side groups (e.g., C, F, H, M, W and Y) are useful for altering the ability of fluorescent proteins to oligomerize, especially when they substitute an amino acid with an uncharged, nonpolar or non-polarizable side chain.

Similarly, monomers of other oligomerizing fluorescent proteins can also be prepared following a similar mutagenesis strategy, and are intended to be within the scope of the present invention.

Variant Anthozoan Fluorescent Proteins

It is contemplated that the mutagenesis methods provided by the present invention can be used to generate advantageous fluorescent protein variants that have reduced ability to oligomerize (i.e., tetramerize), and also find uses analogous to the uses of the *Discosoma* DsRed variant proteins. It is known in the art that the DsRed protein is a member of a family of highly related homologous proteins sharing high degrees of amino acid identity and protein structure (see, e.g., Labas et al., *Proc. Natl. Acad. Sci. USA* 99:4256–4261 [2002]; and Yanushevich et al., *FEBS Letters* 511:11–14 [2002]). These alternative fluorescent proteins are additionally advantageous since they have the ability to fluoresce at different wavelengths than does *Discosoma* DsRed. If dimeric or monomeric forms of these proteins can be produced, they will have great experimental potential as fluorescent markers.

Anthozoan species from which related fluorescent proteins have been identified includes, but is not limited to, *Anemonia* sp., *Clavularia* sp., *Condylactis* sp., *Heteractis* sp., *Renilla* sp., *Ptilosarcus* sp., *Zoonthus* sp., *Scolymia* sp., *Montastraea* sp., *Ricordea* sp., *Goniopara* sp., and others.

Fusion Proteins Comprising the Tandem Dimers and Monomers

Fluorescent proteins fused to target proteins can be prepared, for example using recombinant DNA methods, and used as markers to identify the location and amount of the target protein produced. Accordingly, the present invention provides fusion proteins comprising a fluorescent protein variant moiety and a polypeptide of interest. The polypeptide of interest can be of any length, for example, about 15 amino acid residues, about 50 residues, about 150 residues, or up to about 1000 amino acid residues or more, provided that the fluorescent protein component of the fusion protein can fluoresce or can be induced to fluoresce when exposed to electromagnetic radiation of the appropriate wavelength. The polypeptide of interest can be, for example, a peptide tag such as a polyhistidine sequence, a c-myc epitope, a FLAG epitope, and the like; can be an enzyme, which can be used to effect a function in a cell expressing a fusion protein comprising the enzyme or to identify a cell containing the fusion protein; can be a protein to be examined for an ability to interact with one or more other proteins in a cell, or any other protein as disclosed herein or otherwise desired.

As disclosed herein, the *Discosoma* (coral) red fluorescent protein, DsRed, can be used as a complement to or alternative for a GFP or spectral variant thereof. In particular, the invention encompasses fusion proteins of any of the tandem dimeric and monomeric DsRed fluorescent proteins discussed above, and variants thereof, which has altered spectral and/or fluorescent characteristics.

A fusion protein, which includes a fluorescent protein variant operatively linked to one or more polypeptides of interest also is provided. The polypeptides of the fusion protein can be linked through peptide bonds, or the fluorescent protein variant can be linked to the polypeptide of interest through a linker molecule. In one embodiment, the fusion protein is expressed from a recombinant nucleic acid molecule containing a polynucleotide encoding a fluorescent protein variant operatively linked to one or more polynucleotides encoding one or more polypeptides of interest.

A polypeptide of interest can be any polypeptide, including, for example, a peptide tag such as a polyhistidine peptide, or a cellular polypeptide such as an enzyme, a G-protein, a growth factor receptor, or a transcription factor; and can be one of two or more proteins that can associate to form a complex. In one embodiment, the fusion protein is a tandem fluorescent protein variant construct, which includes a donor fluorescent protein variant, an acceptor fluorescent protein variant, and a peptide linker moiety coupling said donor and said acceptor, wherein cyclized amino acids of the donor emit light characteristic of said donor, and wherein the donor and the acceptor exhibit fluorescence resonance energy transfer when the donor is excited, and the linker moiety does not substantially emit light to excite the donor. As such, a fusion protein of the invention can include two or more operatively linked fluorescent protein variants, which can be linked directly or indirectly, and can further comprise one or more polypeptides of interest.

Preparation of DsRed Dimers and Monomers

The present invention also provides polynucleotides encoding fluorescent protein variants, where the protein can be a dimeric fluorescent protein, a tandem dimeric fluorescent protein, a monomeric protein, or a fusion protein comprising a fluorescent protein operatively linked to one or more polypeptides of interest. In the case of the tandem dimer the entire dimer may be encoded by one polynucleotide molecule. If the linker is a non-peptide linker, the two subunits will be encoded by separate polynucleotide molecules, produced separately, and subsequently linked by methods known in the art.

The invention further concerns vectors containing such polynucleotides, and host cell containing a polynucleotide or vector. Also provided is a recombinant nucleic acid molecule, which includes at least one polynucleotide encoding a fluorescent protein variant operatively linked to one or more other polynucleotides. The one or more other polynucleotides can be, for example, a transcription regulatory element such as a promoter or polyadenylation signal sequence, or a translation regulatory element such as a ribosome binding site. Such a recombinant nucleic acid molecule can be contained in a vector, which can be an expression vector, and the nucleic acid molecule or the vector can be contained in a host cell.

The vector generally contains elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, Goeddel, ed. (Academic Press, Inc., 1990); Jolly, *Canc. Gene Ther.* 1:51–64, 1994; Flotte, *J. Bioenerg. Biomemb.* 25:37–42, 1993; Kirshenbaum et al., *J. Clin. Invest.* 92:381–387, 1993; each of which is incorporated herein by reference).

A vector for containing a polynucleotide encoding a fluorescent protein variant can be a cloning vector or an expression vector, and can be a plasmid vector, viral vector, and the like. Generally, the vector contains a selectable marker independent of that encoded by a polynucleotide of the invention, and further can contain transcription or translation regulatory elements, including a promoter sequence, which can provide tissue specific expression of a polynucleotide operatively linked thereto, which can, but need not, be the polynucleotide encoding the fluorescent protein variant, for example, a tandem dimer fluorescent protein, thus providing a means to select a particular cell type from among a mixed population of cells containing the introduced vector and recombinant nucleic acid molecule contained therein.

Where the vector is a viral vector, it can be selected based on its ability to infect one or few specific cell types with relatively high efficiency. For example, the viral vector also can be derived from a virus that infects particular cells of an organism of interest, for example, vertebrate host cells such as mammalian host cells. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman, *BioTechniques* 7:980–990, 1992; Anderson et al., *Nature* 392:25–30 Suppl., 1998; Verma and Somia, *Nature* 389:239–242, 1997; Wilson, *New Engl. J. Med.* 334:1185–1187 (1996), each of which is incorporated herein by reference).

Recombinant production of a fluorescent protein variant, which can be a component of a fusion protein, involves expressing a polypeptide encoded by a polynucleotide. A polynucleotide encoding the fluorescent protein variant is a useful starting material. Polynucleotides encoding fluorescent protein are disclosed herein or otherwise known in the art, and can be obtained using routine methods, then can be modified such that the encoded fluorescent protein lacks a propensity to oligomerize. For example, a polynucleotide encoding a GFP can be isolated by PCR of cDNA from *A. victoria* using primers based on the DNA sequence of *Aequorea* GFP (SEQ ID NO: 21). A polynucleotide encoding the red fluorescent protein from *Discosoma* (DsRed) can be similarly isolated by PCR of CDNA of the *Discosoma* coral, or obtained from the commercially available DsRed2 or HcRed1 (CLONTECH). PCR methods are well known and routine in the art (see, for example, U.S. Pat. No. 4,683,195; Mullis et al., *Cold Spring Harbor Symp. Quant. Biol.* 51:263, 1987; Erlich, ed., "PCR Technology" (Stockton Press, N.Y., 1989)). A variant form of the fluorescent protein then can be made by site-specific mutagenesis of the polynucleotide encoding the fluorescent protein. Similarly, a tandem dimer fluorescent protein can be expressed from a polynucleotide prepared by PCR or obtained otherwise, using primers that can encode, for example, a peptide linker, which operatively links a first monomer and at least a second monomer of a fluorescent protein.

The construction of expression vectors and the expression of a polynucleotide in transfected cells involves the use of molecular cloning techniques also well known in the art (see Sambrook et al., In "Molecular Cloning: A Laboratory Manual" (Cold Spring Harbor Laboratory Press 1989); "Current Protocols in Molecular Biology" (eds., Ausubel et al.; Greene Publishing Associates, Inc., and John Wiley & Sons, Inc. 1990 and supplements). Expression vectors contain expression control sequences operatively linked to a polynucleotide sequence of interest, for example, that encodes a fluorescent protein variant, as indicated above. The expression vector can be adapted for function in prokaryotes or eukaryotes by inclusion of appropriate promoters, replication sequences, markers, and the like. An expression vector can be transfected into a recombinant host cell for expression of a fluorescent protein variant, and host cells can be selected, for example, for high levels of expression in order to obtain a large amount of isolated protein. A host cell can be maintained in cell culture, or can be a cell in vivo in an organism. A fluorescent protein variant can be produced by expression from a polynucleotide encoding the protein in a host cell such as *E. coli. Aequorea* GFP-related fluorescent proteins, for example, are best expressed by cells cultured between about 15° C. and 30° C., although higher temperatures such as 37° C. can be used. After synthesis, the fluorescent proteins are stable at higher temperatures and can be used in assays at such temperatures.

An expressed fluorescent protein variant, which can be a tandem dimer fluorescent protein or a non-oligomerizing monomer, can be operatively linked to a first polypeptide of interest, further can be linked to a second polypeptide of interest, for example, a peptide tag, which can be used to facilitate isolation of the fluorescent protein variant, including any other polypeptides linked thereto. For example, a polyhistidine tag containing, for example, six histidine residues, can be incorporated at the N-terminus or C-terminus of the fluorescent protein variant, which then can be isolated in a single step using nickel-chelate chromatography. Additional peptide tags, including a c-myc peptide, a FLAG epitope, or any ligand (or cognate receptor), including any peptide epitope (or antibody, or antigen binding fragment thereof, that specifically binds the epitope are well known in the art and similarly can be used. (see, for example, Hopp et al., *Biotechnology* 6:1204 (1988); U.S. Pat. No. 5,011,912, each of which is incorporated herein by reference).

Kits of the Invention

The present invention also provides kits to facilitate and/or standardize use of compositions provided by the present invention, as well as facilitate the methods of the present invention. Materials and reagents to carry out these various methods can be provided in kits to facilitate execution of the methods. As used herein, the term "kit" is used in reference to a combination of articles that facilitate a process, assay, analysis or manipulation.

Kits can contain chemical reagents (e.g., polypeptides or polynucleotides) as well as other components. In addition, kits of the present invention can also include, for example but not limited to, apparatus and reagents for sample collection and/or purification, apparatus and reagents for product collection and/or purification, reagents for bacterial cell transformation, reagents for eukaryotic cell transfection, previously transformed or transfected host cells, sample tubes, holders, trays, racks, dishes, plates, instructions to the kit user, solutions, buffers or other chemical reagents, suitable samples to be used for standardization, normalization, and/or control samples. Kits of the present invention can also be packaged for convenient storage and safe shipping, for example, in a box having a lid.

In some embodiments, for example, kits of the present invention can provide a fluorescent protein of the invention, a polynucleotide vector (e.g., a plasmid) encoding a fluorescent protein of the invention, bacterial cell strains suitable for propagating the vector, and reagents for purification of expressed fusion proteins. Alternatively, a kit of the present invention can provide the reagents necessary to conduct mutagenesis of an Anthozoan fluorescent protein in order to generate a protein variant having a redued propensity to oligomerize.

A kit can contain one or more compositions of the invention, for example, one or a plurality of fluorescent protein variants, which can be a portion of a fusion protein, or one or a plurality of polynucleotides that encode the polypeptides. The fluorescent protein variant can be a mutated fluorescent protein having a reduced propensity to oligomerize, such as a non-oligomerizing monomer, or can be a tandem dimer fluorescent protein and, where the kit comprises a plurality of fluorescent protein variants, the plurality can be a plurality of the mutated fluorescent protein variants, or of the tandem dimer fluorescent proteins, or a combination thereof.

A kit of the invention also can contain one or a plurality of recombinant nucleic acid molecules, which encode, in part, fluorescent protein variants, which can be the same or different, and can further include, for example, an operatively linked second polynucleotide containing or encoding a restriction endonuclease recognition site or a recombinase recognition site, or any polypeptide of interest. In addition, the kit can contain instructions for using the components of the kit, particularly the compositions of the invention that are contained in the kit.

Such kits can be particularly useful where they provide a plurality of different fluorescent protein variants because the artisan can conveniently select one or more proteins having the fluorescent properties desired for a particular application. Similarly, a kit containing a plurality of polynucleotides encoding different fluorescent protein variants provides numerous advantages. For example, the polynucleotides can be engineered to contain convenient restriction endonuclease or recombinase recognition sites, thus facilitating operative linkage of the polynucleotide to a regulatory element or to a polynucleotide encoding a polypeptide of interest or, if desired, for operatively linking two or more the polynucleotides encoding the fluorescent protein variants to each other.

Uses of Fluorescent Protein Variants

A fluorescent protein variant of the invention is useful in any method that employs a fluorescent protein. Thus, the fluorescent protein variants, including the monomeric, dimeric, and tandem dimer fluorescent proteins, are useful as fluorescent markers in the many ways fluorescent markers already are used, including, for example, coupling fluorescent protein variants to antibodies, polynucleotides or other receptors for use in detection assays such as immunoassays or hybridization assays, or to track the movement of proteins in cells. For intracellular tracking studies, a first (or other) polynucleotide encoding the fluorescent protein variant is fused to a second (or other) polynucleotide encoding a protein of interest and the construct, if desired, can be inserted into an expression vector. Upon expression inside the cell, the protein of interest can be localized based on fluorescence, without concern that localization of the protein is an artifact caused by oligomerization of the fluorescent protein component of the fusion protein. In one embodiment of this method, two proteins of interest independently are fused with two fluorescent protein variants that have different fluorescent characteristics.

The fluorescent protein variants of this invention are useful in systems to detect induction of transcription. For example, a nucleotide sequence encoding a non-oligomerizing monomeric, dimeric or tandem dimeric fluorescent protein can be fused to a promoter or other expression control sequence of interest, which can be contained in an expression vector, the construct can be transfected into a cell, and induction of the promoter (or other regulatory element) can be measured by detecting the presence or amount of fluorescence, thereby allowing a means to observe the responsiveness of a signaling pathway from receptor to promoter.

A fluorescent protein variant of the invention also is useful in applications involving FRET, which can detect events as a function of the movement of fluorescent donors and acceptors towards or away from each other. One or both of the donor/acceptor pair can be a fluorescent protein variant. Such a donor/acceptor pair provides a wide separation between the excitation and emission peaks of the donor, and provides good overlap between the donor emission spectrum and the acceptor excitation spectrum. Variant red fluorescent proteins or red-shifted mutants as disclosed herein are specifically disclosed as the acceptor in such a pair.

FRET can be used to detect cleavage of a substrate having the donor and acceptor coupled to the substrate on opposite sides of the cleavage site. Upon cleavage of the substrate, the donor/acceptor pair physically separate, eliminating FRET. Such an assay can be performed, for example, by contacting the substrate with a sample, and determining a qualitative or quantitative change in FRET (see, for example, U.S. Pat. No. 5,741,657, which is incorporated herein by reference). A fluorescent protein variant donor/acceptor pair also can be part of a fusion protein coupled by a peptide having a proteolytic cleavage site (see, for example, U.S. Pat. No. 5,981,200, which is incorporated herein by reference). FRET also can be used to detect changes in potential across a membrane. For example, a donor and acceptor can be placed on opposite sides of a membrane such that one translates across the membrane in response to a voltage change, thereby producing a measurable FRET (see, for example, U.S. Pat. No. 5,661,035, which is incorporated herein by reference).

In other embodiments, a fluorescent protein of the invention is useful for making fluorescent sensors for protein kinase and phosphatase activities or indicators for small ions and molecules such as $Ca^{2+}$, $Zn^{2+}$, cyclic 3',5'-adenosine monophosphate, and cyclic 3',5'-guanosine monophosphate.

Fluorescence in a sample generally is measured using a fluorimeter, wherein excitation radiation from an excitation source having a first wavelength, passes through excitation optics, which cause the excitation radiation to excite the sample. In response, a fluorescent protein variant in the sample emits radiation having a wavelength that is different from the excitation wavelength. Collection optics then collect the emission from the sample. The device can include a temperature controller to maintain the sample at a specific temperature while it is being scanned, and can have a multi-axis translation stage, which moves a microtiter plate holding a plurality of samples in order to position different wells to be exposed. The multi-axis translation stage, temperature controller, auto-focusing feature, and electronics associated with imaging and data collection can be managed by an appropriately programmed digital computer, which also can transform the data collected during the assay into another format for presentation. This process can be miniaturized and automated to enable screening many thousands of compounds in a high throughput format. These and other methods of performing assays on fluorescent materials are well known in the art (see, for example, Lakowicz, "Principles of Fluorescence Spectroscopy" (Plenum Press 1983); Herman, "Resonance energy transfer microscopy" In "Fluorescence Microscopy of Living Cells in Culture" Part B, *Meth. Cell Biol.* 30:219–243 (ed. Taylor and Wang; Academic Press 1989); Turro, "Modern Molecular Photochemistry" (Benjamin/Cummings Publ. Co., Inc. 1978), pp. 296–361, each of which is incorporated herein by reference).

Accordingly, the present invention provides a method for identifying the presence of a molecule in a sample. Such a method can be performed, for example, by linking a fluorescent protein variant of the invention to the molecule, and detecting fluorescence due to the fluorescent protein variant in a sample suspected of containing the molecule. The molecule to be detected can be a polypeptide, a polynucleotide, or any other molecule, including, for example, an antibody, an enzyme, or a receptor, and the fluorescent protein variant can be a tandem dimer fluorescent protein.

The sample to be examined can be any sample, including a biological sample, an environmental sample, or any other sample for which it is desired to determine whether a particular molecule is present therein. Preferably, the sample includes a cell or an extract thereof. The cell can be obtained from a vertebrate, including a mammal such as a human, or from an invertebrate, and can be a cell from a plant or an animal. The cell can be obtained from a culture of such cells, for example, a cell line, or can be isolated from an organism. As such, the cell can be contained in a tissue sample, which can be obtained from an organism by any means commonly used to obtain a tissue sample, for example, by biopsy of a human. Where the method is performed using an intact living cell or a freshly isolated tissue or organ sample, the presence of a molecule of interest in living cells can be identified, thus providing a means to determine, for example, the intracellular compartmentalization of the molecule. The use of the fluorescent protein variants of the invention for such a purpose provides a substantial advantage in that the likelihood of aberrant identification or localization due to oligomerization the fluorescent protein is greatly minimized.

A fluorescent protein variant can be linked to the molecule directly or indirectly, using any linkage that is stable under the conditions to which the protein-molecule complex is to be exposed. Thus, the fluorescent protein and molecule can be linked via a chemical reaction between reactive groups present on the protein and molecule, or the linkage can be mediated by linker moiety, which contains reactive groups specific for the fluorescent protein and the molecule. It will be recognized that the appropriate conditions for linking the fluorescent protein variant and the molecule are selected depending, for example, on the chemical nature of the molecule and the type of linkage desired. Where the molecule of interest is a polypeptide, a convenient means for linking a fluorescent protein variant and the molecule is by expressing them as a fusion protein from a recombinant nucleic acid molecule, which comprises a polynucleotide encoding, for example, a tandem dimer fluorescent protein operatively linked to a polynucleotide encoding the polypeptide molecule.

A method of identifying an agent or condition that regulates the activity of an expression control sequence also is provided. Such a method can be performed, for example, by exposing a recombinant nucleic acid molecule, which includes a polynucleotide encoding a fluorescent protein variant operatively linked to an expression control sequence, to an agent or condition suspected of being able to regulate expression of a polynucleotide from the expression control sequence, and detecting fluorescence of the fluorescent protein variant due to such exposure. Such a method is useful, for example, for identifying chemical or biological agents, including cellular proteins, that can regulate expression from the expression control sequence, including cellular factors involved in the tissue specific expression from the regulatory element. As such, the expression control sequence can be a transcription regulatory element such as a promoter, enhancer, silencer, intron splicing recognition site, polyadenylation site, or the like; or a translation regulatory element such as a ribosome binding site.

The fluorescent protein variants of the invention also are useful in a method of identifying a specific interaction of a first molecule and a second molecule. Such a method can be performed, for example, by contacting the first molecule, which is linked to a donor first fluorescent protein variant, and the second molecule, which is linked to an acceptor second fluorescent protein variant, under conditions that allow a specific interaction of the first molecule and second molecule; exciting the donor; and detecting fluorescence or luminescence resonance energy transfer from the donor to the acceptor, thereby identifying a specific interaction of the first molecule and the second molecule. The conditions for such an interaction can be any conditions under which is expected or suspected that the molecules can specifically interact. In particular, where the molecules to be examined are cellular molecules, the conditions generally are physiological conditions. As such, the method can be performed in vitro using conditions of buffer, pH, ionic strength, and the like, that mimic physiological conditions, or the method can be performed in a cell or using a cell extract.

Luminescence resonance energy transfer entails energy transfer from a chemiluminescent, bioluminescent, lanthanide, or transition metal donor to the red fluorescent protein moiety. The longer wavelengths of excitation of red fluorescent proteins permit energy transfer from a greater variety of donors and over greater distances than possible with green fluorescent protein variants. Also, the longer wavelengths of emission is more efficiently detected by solid-state photodetectors and is particularly valuable for in vivo applications where red light penetrates tissue far better than shorter wavelengths. Chemiluminescent donors include but are not limited to luminol derivatives and peroxyoxalate systems. Bioluminescent donors include but are not limted to aequorin, obelin, firefly luciferase, *Renilla* luciferase, bacterial luciferase, and variants thereof. Lanthanide donors include but are not limited to terbium chelates containing ultraviolet-absorbing sensitizer chromophores linked to multiple liganding groups to shield the metal ion from solvent water. Transition metal donors include but are not limited to ruthenium and osmium chelates of oligopyridine ligands. Chemiluminescent and bioluminescent donors need no excitation light but are energized by addition of substrates, whereas the metal-based systems need excitation light but offer longer excited state lifetimes, facilitating time-gated detection to discriminate against unwanted background fluorescence and scattering.

The first and second molecules can be cellular proteins that are being investigated to determine whether the proteins specifically interact, or to confirm such an interaction. Such first and second cellular proteins can be the same, where they are being examined, for example, for an ability to oligomerize, or they can be different where the proteins are being examined as specific binding partners involved, for example, in an intracellular pathway. The first and second molecules also can be a polynucleotide and a polypeptide, for example, a polynucleotide known or to be examined for transcription regulatory element activity and a polypeptide known or being tested for transcription factor activity. For example, the first molecule can comprise a plurality of nucleotide sequences, which can be random or can be variants of a known sequence, that are to be tested for transcription regulatory element activity, and the second molecule can be a transcription factor, such a method being useful for identifying novel transcription regulatory elements having desirable activities.

The present invention also provides a method for determining whether a sample contains an enzyme. Such a method can be performed, for example, by contacting a sample with a tandem fluorescent protein variant of the invention; exciting the donor, and determining a fluorescence property in the sample, wherein the presence of an enzyme in the sample results in a change in the degree of fluorescence resonance energy transfer. Similarly, the present invention relates to a method for determining the activity of an enzyme in a cell. Such a method can be performed, for example, providing a cell that expresses a tandem fluorescent protein variant construct, wherein the peptide linker moiety comprises a cleavage recognition amino acid sequence specific for the enzyme coupling the donor and the acceptor; exciting said donor, and determining the degree of fluorescence resonance energy transfer in the cell, wherein the presence of enzyme activity in the cell results in a change in the degree of fluorescence resonance energy transfer.

Also provided is a method for determining the pH of a sample. Such a method can be performed, for example, by contacting the sample with a first fluorescent protein variant, which can be a tandem dimer fluorescent protein, wherein the emission intensity of the first fluorescent protein variant changes as pH varies between pH 5 and pH 10; exciting the indicator; and determining the intensity of light emitted by the first fluorescent protein variant at a first wavelength, wherein the emission intensity of the first fluorescent protein variant indicates the pH of the sample. The first fluorescent protein variant useful in this method, or in any method of the invention, can comprise two DsRed monomers as set forth in SEQ ID NO: 8. It will be recognized that such fluorescent protein variants similarly are useful, either alone or in combination, for the variously disclosed methods of the invention.

The sample used in a method for determining the pH of a sample can be any sample, including, for example, a biological tissue sample, or a cell or a fraction thereof. In addition, the method can further include contacting the sample with a second fluorescent protein variant, wherein the emission intensity of the second fluorescent protein variant changes as pH varies from 5 to 10, and wherein the second fluorescent protein variant emits at a second wavelength that is distinct from the first wavelength; exciting the second fluorescent protein variant; determining the intensity of light emitted by the second fluorescent protein variant at the second wavelength; and comparing the fluorescence at the second wavelength to the fluorescence at the first wavelength. The first (or second) fluorescent protein variant can include a targeting sequence, for example, a cell compartmentalization domain such a domain that targets the fluorescent protein variant in a cell to the cytosol, the endoplasmic reticulum, the mitochondrial matrix, the chloroplast lumen, the medial trans-Golgi cisternae, a lumen of a lysosome, or a lumen of an endosome. For example, the cell compartmentalization domain can include amino acid residues 1 to 81 of human type II membrane-anchored protein galactosyltransferase, or amino acid residues 1 to 12 of the presequence of subunit IV of cytochrome c oxidase.

The following Examples are provided to further illustrate certain embodiments and aspects of the present invention. It is not intended that these Examples should limit the scope of any aspect of the invention. Although specific reaction conditions and reagents are described, it is clear that one familiar with the art would recognize alternative or equivalent conditions that also find use with the invention, where the alternative or equivalent conditions do not depart from the scope of the invention.

EXAMPLE 1

Construction of Dimeric and Monomeric Red Flourescent Proteins

Materials and Methods

DsRed Mutagenesis and Screening

The DsRed gene was amplified from vector pDsRed-N1 (CLONTECH, Palo Alto, Calif.) or the T1 variant (provided by B. S. Glick, University of Chicago) and subcloned into PRSET$_B$ (Invitrogen™; see Baird et al., *Proc. Natl. Acad. Sci. USA* 97:11984–11989 [2000]) (4). The PRSET$_B$ vector produces 6×His tagged fusion proteins, where an N-terminal polyhistidine tag having the following sequence is coupled to the suitably subcloned sequence.

MRGSHHHHHHGMASMTGGQQMGRDLYD-DDDKDP (SEQ ID NO: 22)

This resulting construct was used as the template for introduction of the I125R mutant using the QuikChange™ Site Directed Mutagenesis Kit (Stratagene®), according to the manufacturer's instructions. The complete DsRed wild-type cDNA and polypeptide sequences are provided in GenBank Accession Number AF168419. This nucleotide sequence is also provided in FIG. 16 and SEQ ID NO: 2. A variation of this nucleotide sequence is also known (Clontech), where various nucleotide positions been amended to accommodate mammalian codon usage utilization preferences. This nucleotide sequence is provided in FIG. 25 and SEQ ID NO: 23. The corresponding polypeptide encoded by both of these nucleotide sequences is provided in FIG. 17 and SEQ ID NO: 1.

Similarly, the DsRed T1 variant cDNA nucleotide sequence is provided in FIG. 18 and SEQ ID NO: 5. The corresponding polypeptide is provided in FIG. 19 and SEQ ID NO: 4.

As used herein, the numbering of DsRed amino acids conforms to the wild-type sequence of GFP, in which residues 66–68 of wild-type DsRed (Gln-Tyr-Gly) are homologous to the chromophore-forming residues 65–67 of GFP (Ser-Tyr-Gly). The amino-terminal polyhistidine tag is numbered −33 to −1.

Error-prone PCR Mutagenesis—Error prone PCR was performed essentially as described in Griesbeck et al. (*J. Biol. Chem.*, 276:29188–29194 [2001]). Breifly, the cDNA encoding DsRed in the vector PRSET$_B$ (Invitrogen™) was subjected to error-prone PCR using Taq DNA polymerase. The 5' primer included a BamHI site and ended at the starting Met of the DsRed, and the 3' primer included an EcoRI site and ended at the stop codon, theoretically allowing mutagenesis of every base of DsRed open reading frame, except for the initiator methionine. The PCR reactions (38 cycles with annealing at 55° C.) were run in four 100 μL batches, each containing 10 μL of 10×PCR buffer with Mg$^{2+}$ (Roche Molecular Biochemicals), 150 μM Mn$^{2+}$, 250 μM of three nucleotides, 50 μM of the remaining nucleotide, and 5 ng of template DNA.

Mutagenized PCR products were combined, purified by agarose gel electrophoresis, digested with BamHI and EcoRI, and isolated by QIAGEN® QIAquick™ DNA purification spin column following the manufacturer's instructions. The resulting fragments were ligated into PRSET$_B$, and the crude ligation mixture was transformed into *E. coli* BL21(DE3) Gold (Stratagene®) by electroporation.

Overlap Extension PCR Mutagenesis—Semi-random mutations at multiple distant locations were introduced by overlap extension PCR with multiple fragments essentially as described in Ho et al., *Gene* 77:51–59 (1989). Briefly, two to four pairs of sense and antisense oligonucleotide primers (Invitrogem™ or GenBase), with semi-degenerate codons at positions of interest, were used for PCR amplification of the DsRed template with Pfu DNA polymerase (Stratagene®) in individual reactions. The resulting overlapping fragments were gel purified using QIAGEN® gel extraction kit and recombined by overlap extension PCR with Pfu or Taq DNA polymerase (Roche).

Full length genes were digested with BamHI/EcoRI (New England BioLabs®) and ligated into PRSET$_B$ with T4 ligase (New England BioLabs®). Chemically competent *E. coli* JM109(DE3) were transformed and grown on LB/agar at 37° C.

Bacterial Fluorescence Screening—Bacteria plated on LB/agar plates were screened essentially as described in Baird et al., *Proc. Natl. Acad. Sci. USA* 96:11241–11246 (1999). Briefly, the bacterial plates were illuminated with a 150-W Xe lamp using 470 nm (40 nm bandwidth), 540 nm (30 nm bandwidth), or 560 nm (40 nm bandwidth) excitation filters and 530 nm (40 nm bandwidth), 575 nm (long pass), or 610 nm (long pass) emission filters. Fluorescence was imaged by a cooled charge-coupled device camera (Sensys Photometrics, Tucson, Ariz.) and were processed using Metamorph software (Universal Imaging, West Chester, Pa.).

Fluorescent colonies of interest were cultured overnight in 2 ml of LB supplemented with ampicillin. Bacteria were pelleted by centrifugation and imaged again to ensure that the protein was expressed well in culture. For fast maturing proteins a fraction of the cell pellet was extracted with B-per II (Pierce) and complete spectra obtained. DNA was purified from the remaining pellet by QIAGEN® QIAprep® plasmid isolation spin column according to the manufacturer's instructions and submitted for DNA sequencing. To determine the oligomeric state of DsRed mutants, a single colony of *E. coli* was restreaked on LB/agar and allowed to mature at room temperature. After 2 days to 2 weeks the bacteria were scraped from the plate, extracted with B-per II, analyzed (not boiled) by SDS-PAGE (BioRad), and the gel imaged with a digital camera.

Bacterial Transformations and DsRed Protein Purification

Ligation mixtures were transformed into *Escherichia coli* BL21(DE3) Gold (Stratagene) by electroporation in 10% glycerol with a ligation mixture (0.1 cm cuvette, 12.5 kV/cm, 200 Ω, 25 μF).

Protein was expressed and purified essentially as described in Baird et al., *Proc. Natl. Acad. Sci. USA* 96:11241–11246 (1999). Briefly, when cultured for protein expression, transformed bacteria were grown to an $OD_{600}$ of 0.6 in LB containing 100 mg/liter ampicillin, at which time they were induced with 1 mM isopropyl β-D-thiogalactoside. Bacteria were allowed to express recombinant protein for 6 hr at room temperature and then overnight at 4° C. The bacteria then were pelleted by centrifugation, resuspended in 50 mM Tris.HCl/300 mM NaCl, and lysed by a French press. The bacterial lysates were centrifuged at 30,000×g for 30 min, and the proteins were purified from the supernatants using Ni-NTA resin (QIAGEN®).

Spectroscopy of purified protein was typically performed in 100 mM KCl, 10 mM MOPS, pH 7.25, in a fluorescence spectrometer (Fluorolog-2, Spex Industries). All DNA sequencing was performed by the Molecular Pathology Shared Resource, University of California, San Diego, Cancer Center.

Construction of DsRed Tandem Dimers and Constructs for Mammalian Cell Expression including Chimeric Constructs To construct tandem dimers of DsRed protein, dimer2 in $PRSET_B$ was amplified in two separate PCR reactions. In the first reaction, the 5' BamHI and a 3' SphI site were introduced while in the second reaction a 5' SacI and a 3' EcoRI site were introduced. The construct was assembled in a 4-part ligation containing the digested dimer2 genes, a synthetic linker with phosphorylated sticky ends, and digested $PRSET_B$. Four different linkers were used, which encoded polypeptides of various lengths. These were:

| Linker | Polypeptide Sequence | SEQ ID NO |
|---|---|---|
| 9 a.a. residue linker | RMGTGSGQL | 16 |
| 12 a.a. residue linker | GHGTGSTGSGSS | 17 |
| 13 a.a. residue linker | RMGSTSGSTKGQL | 18 |
| 22 a.a. residue linker | RMGSTSGSGKPGSGEGSTKGQL | 19 |

For expression in mammalian cells, DsRed variants were amplified from $PRSET_B$ with a 5' primer that encoded a KpnI restriction site and a Kozak sequence. The PCR product was digested, ligated into pcDNA3, and used to transform *E. coli* DH5α.

A gene encoding a chimeric fusion polypeptide comprising DsRed and connexin43 (Cx43) was constructed. To produce these fusions, Cx43 was first amplified with a 3' primer encoding a seven-residue linker ending in a BamHI site. The construct was assembled in a 3-part ligation containing KpnI/BamHI digested Cx43, BamHI/EcoRI digested enhanced GFP, and digested pcDNA3. For all other fusion proteins (Cx43-T1, -dimer 2, -tdimer2(12) and -mRFP1) the gene for the fluorescent protein was ligated into the BamHI/EcoRI digested Cx43-GFP vector.

DsRed Protein Variant Production and Characterization

DsRed variants were expressed essentially as described in Baird et al., *Proc. Natl. Acad. Sci. USA* 96:11241–11246 (1999). All proteins were purified by Ni-NTA chromatography (QIAGEN®) according to the manufacturer's instructions and dialyzed into 10 mM Tris, pH 7.5 or phosphate buffered saline supplemented with 1 mM EDTA. All biochemical characterization experiments were performed essentially as described in Baird et al., *Proc. Natl. Acad. Sci. USA* 97:11984–11989 (2000).

The maturation time courses were determined on a Safire 96 well plate reader with monochromators (TECAN, Austria). All photobleaching measurements were performed in microdroplets under paraffin oil with a Zeiss Axiovert 35 fluorescence microscope equipped with a 40× objective and a 540 nm (25 nm bandpass) excitation filter that delivered 4.5 $W/cm^2$ of light.

Analytical Ultracentrifugation—Purified, recombinant DsRed was dialyzed extensively against PBS, pH 7.4 or 10 mM Tris, 1 mM EDTA, pH 7.5. Sedimentation equilibrium experiments were performed on a Beckman Optima XL-I analytical ultracentrifuge at 20° C. measuring absorbance at 558 nm as a function of radius. Samples of DsRed were normalized to 3.57 $\mu M$ (0.25 absorbance units), and from this, 125 $\mu L$ aliquots were loaded into six channel cells. The data were analyzed globally at 10K, 14K, and 20K rpm by nonlinear least-squares analysis using the ORIGIN software package supplied by Beckman. The goodness of fit was evaluated on the basis of the magnitude and randomness of the residuals, expressed as the difference between the experimental data and the theoretical curve and also by checking each of the fit parameters for physical reasonability.

Absorption/Fluorescence Spectra and Extinction Coefficients—Fluorescence spectra were taken with a Fluorolog spectrofluorimeter (Spex Industries, Edison, N.J.). Absorbance spectra of proteins were taken with a Cary UV-Vis spectrophotometer. For quantum yield determination, the fluorescence of a solution of DsRed or DsRed variant in PBS was compared with equally absorbing solutions of rhodamine B and rhodamine 101 in ethanol. Corrections were included in the quantum yield calculation for the refractive index difference between ethanol and water. For extinction coefficient determination, native protein absorbance was measured with the spectrophotometer, and protein concentration was measured by the BCA method (Pierce).

Mammalian Cell Imaging and Microinjection

HeLa cells were transfected with DsRed variants or Cx43-DsRed fusions in pcDNA3 through the use of Fugene 6 transfection reagent (Roche). Transfected cells were grown for 12 hours to 2 days in DMEM at 37° C. before imaging using a Zeiss Axiovert 35 fluorescence microscope with cells in glucose-supplemented HBSS at room temperature. Individual cells expressing Cx43 fused to a DsRed variant, or contacting non-transfected cells for control experiments, were microinjected with a 2.5% solution of lucifer yellow (Molecular Probes, Eugene, Oreg.). Images were acquired and processed with the Metafluor software package (Universal Imaging, West Chester, Pa.).

Results

Stepwise Evolution of DsRed Molecules

The present invention provides methods for the stepwise evolution of tetrameric DsRed to a dimer and then either to a genetic fusion of two copies of the protein, i.e., a tandem dimer, or to a true monomer designated mRFP1. Each subunit interface was disrupted by insertion of arginines, which initially crippled the resulting protein, but red fluorescence could be rescued by random and directed mutagenesis totaling 17 substitutions in the dimer and 33 substitutions in mRFP1. Fusions of the gap junction protein connexin43 to mRFP1 formed fully functional junctions, whereas analogous fusions to the tetramer and dimer failed. Although mRFP1 has somewhat lower extinction coefficient, quantum yield, and photostability than DsRed, mRFP1 matures >10× faster, so that it shows similar brightness in living cells. In addition, the excitation and emission peaks of mRFP1, 584 and 607 nm, are 25 nm red shifted from DsRed, which should confer greater tissue penetration and spectral separation from autofluorescence and other fluorescent proteins.

The consensus view is that a monomeric form of DsRed will be essential if it is to ever reach its full potential as a genetically encoded red fluorescent tag (Remington, *Nat. Biotechnol.,* 20:28–29 [2002]). The present invention provides a directed evolution and preliminary characterization of the first monomeric red fluorescent protein. The present invention provides an independent alternative to GFP in the construction of fluorescently tagged fusion proteins.

Directed and Random Evolution of a Dimer of DsRed

The basic strategy for decreasing the oligomeric state of DsRed was to replace key hydrophobic residues at the dimer interface by charged residues such as arginine. The high energetic cost of burying a charged residue within a nonpolar hydrophobic interface or of placing two positive charges in close proximity should disrupt the interaction. Initial attempts to break apart the DsRed AC interface (see FIG. 2A) with the single mutations T147R, H162R, and F224R, consistently gave non-fluorescent proteins. The AB interface however, proved somewhat less resilient and could be broken with the single mutation I125R to give a poorly red fluorescent dimer that suffered from an increased green component and required more than 10 days to fully mature.

Figure 7:
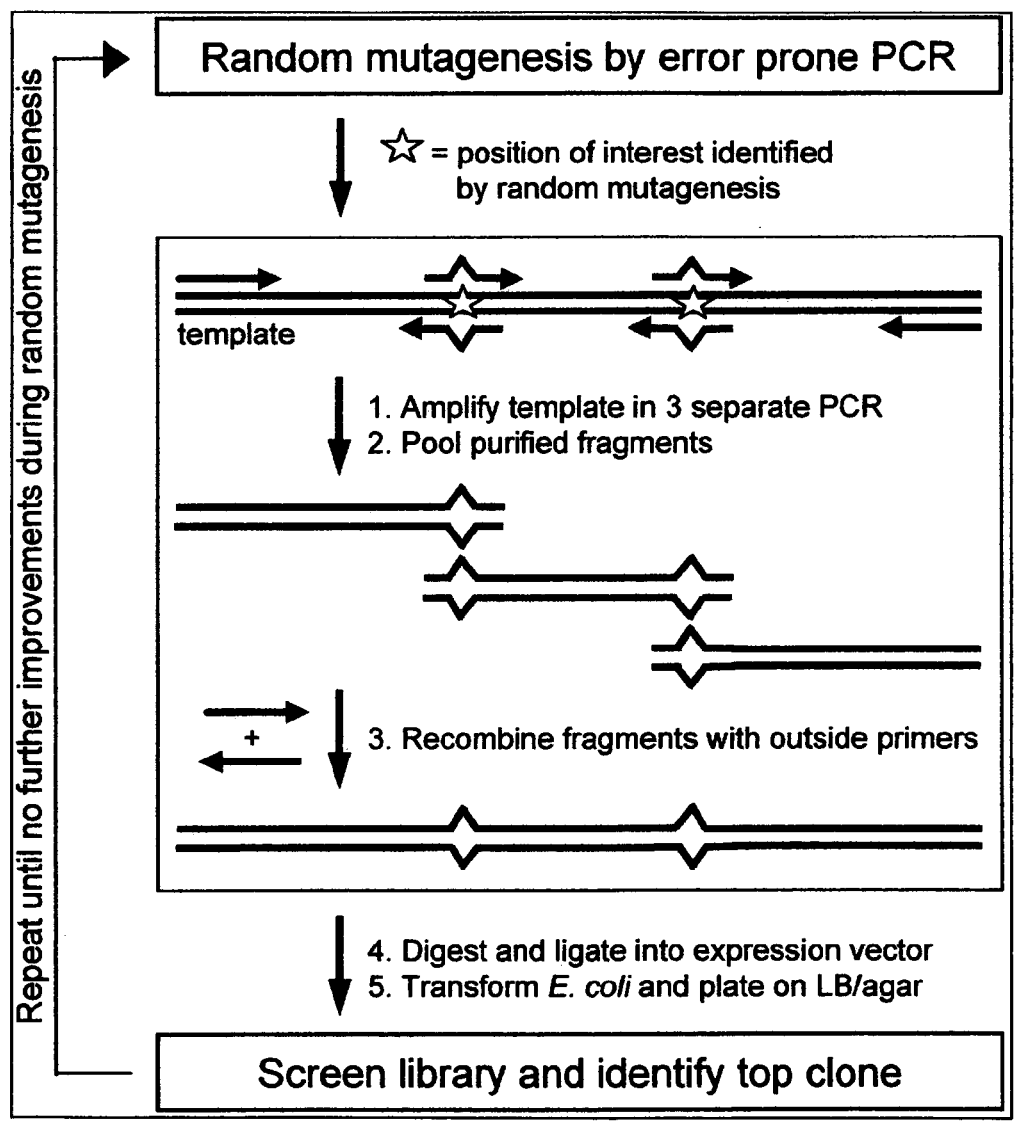
FIG. 7 shows a schematic representation of the directed evolution strategy of the present invention. Randomization at two positions is shown but the technique has been used with up to five fragments.
Figure 8B:
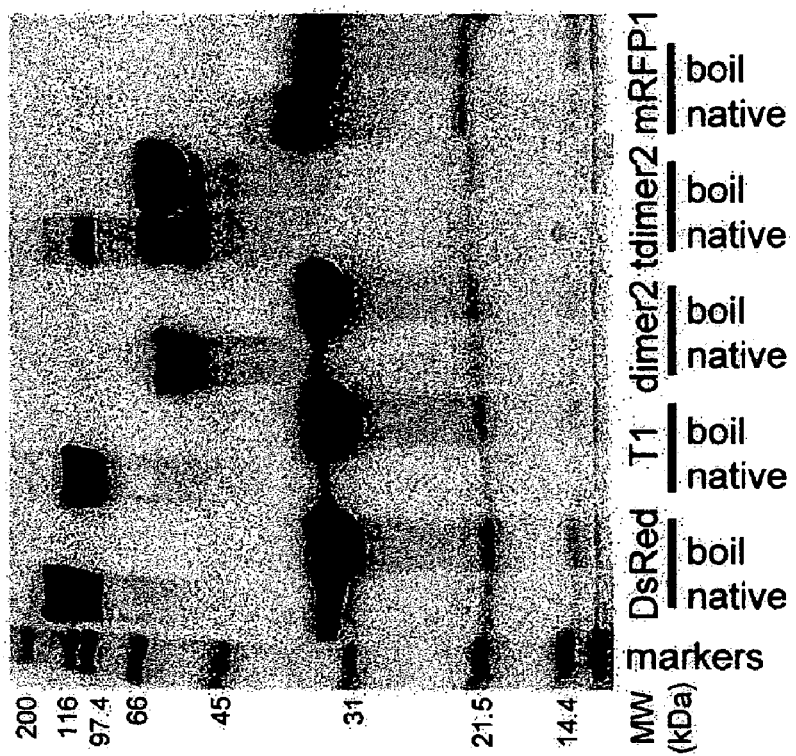
FIGS. 8A and 8B show SDS-PAGE analysis of DsRed, T1, dimer2, tdimer2(12), and mRFP1 polypeptides. The oligomeric state of each protein is demonstrated by running each protein (20 μg) both not boiled and boiled on a 12% SDS-PAGE Tris-HCl precast gel (BioRad).
Figure 8A:
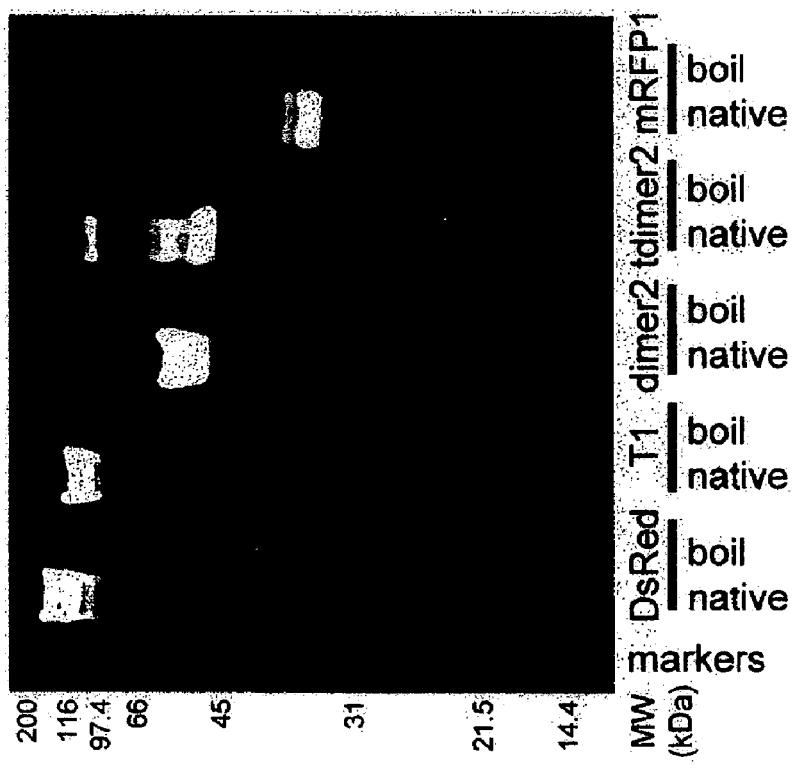

To reconstitute the red fluorescence of DsRed-I125R, the protein was subjected to iterative cycles of evolution. This accelerated evolution strategy useed either random mutagenesis or semi-directed mutagenesis to create a library of mutated molecules, which can be screened for desirable characteristics. The directed evolution strategy of the present invention is shown in FIG. 7. Each cycle of the mutagenesis began with random mutagenesis to identify those positions that effected either the maturation or brightness of the red fluorescent protein. Once several residues were identified, expanded libraries were constructed in which several of these key positions were simultaneously mutated to a number of substitutions (see FIGS. 10–12). These directed libraries combine the benefits of shuffling of improved mutant genes with an efficient method of overcoming the limited number of substitutions accessible during random mutagenesis by error prone PCR. Most methods of in vitro recombination rely on random gene fragmentation. In contrast, the methods of the present invention use PCR to generate designed fragments that can be reassembled to give the full length shuffled gene.

Libraries of mutant red fluorescent proteins were screened in colonies of *E. coli* and were evaluated on both the magnitude of their red fluorescence under direct excitation at 540 nm and the ratio of emission intensities at 540 nm over 470 nm excitation. While the former constraint selected for very bright or fast maturing mutants, the latter constraint selected for mutants with decreased 470 nm excitation or red-shifted excitation spectra. Multiple cycles of random mutagenesis were used to find sequence locations that affected the maturation and brightness of the protein, and then expanded libraries of mutations at those positions were created and recombined to find optimal permutations.

Initial random mutagenesis of DsRed-I125R identified several beneficial mutations including K163Q or M, S179T and T217S. These three positions were included in our first directed library in which a total of seven residues were simultaneously mutated to a number of reasonable substitutions. The additional positions targeted in the first directed library included N42 and V44, residues that are critical for the fast phenotype of T1 (Bevis and Glick, *Nat. Biotechnol.,* 20:83–87 [2002]). Also included were I161 and S197, positions at which specific mutations contributed to the modest improvements of DsRed2 (CLONTECH) and the very similar 'E57' (Terskikh et al., *J. Biol. Chem.,* 277: 7633–7636 [2002]). From this library, several clones were identified such as DsRed-I125R, S179T, T217A and DsRed-I125R, K163Q, T217A, but improvements were not dramatic.

As an alternative strategy, the DsRed variant fast tetramer T1 (Bevis and Glick, *Nat. Biotechnol.,* 20:83–87 [2002]) was also studied. Introduction of the I125R mutation into this protein (T1 DsRed-I125R polypeptide sequence provided in SEQ ID NO: 24) resulted in a dimer that matured in only a few days, which was comparable to the best DsRed dimers produced at that time. By further targeting those positions that had helped rescue DsRed-I125R, dramatic improvements in our first generation library were observed.

A similar directed mutagenesis strategy starting from T1-I125R (see FIG. 10A, library D1) was undertaken and eventually identified dimer1. Dimer1 was somewhat better than wt DsRed both in terms of brightness and rate of maturation but had a substantial green peak equivalent to that of T1. Dimer1 was also somewhat blue-shifted with an excitation maximum at 551 nm and an emission maximum at 579 nm. Error prone PCR on dimer1 (FIG. 10A, library D2) resulted in the discovery of dimer1.02 containing the mutation V71A in the hydrophobic core of the protein and effectively no green component in the excitation spectra. A second round of random mutagenesis (FIG. 10A, library D3) identified the mutations K70R which further decreased the green excitation, S197A which red-shifted the dimer back to DsRed wavelengths and T217S which greatly improved the rate of maturation. Unfortunately, K70R and S197A matured relatively slowly and T217S had a green excitation peak equivalent to DsRed. Using dimer1.02 as the template, two more rounds of directed mutagenesis were performed; the first focusing on the three positions identified above (FIG. 11A, library D3) and the second on C117, F118, F124, and V127 (FIG. 10A, library D4).

Continuing with the directed evolution strategy for a total of 4 generations, an optimal dimeric variant was produced, which was designated dimer2 (illustrated in FIG. 2B). This variant contains 17 mutations, of which eight are internal to the β-barrel (N42Q, V44A, V71A, F118L, K163Q, S179T, S197T and T217S), three are the aggregation reducing mutations found in T1 (R2A, K5E and N6D and see Bevis and Glick, *Nat. Biotechnol.,* 20:83–87 [2002]; and Yanushevich et al., *FEBS Lett.,* 511:11–14 [2002]), two are AB interface mutations (I125R and V127T), and 4 are miscellaneous surface mutations (T21S, H41T, C117T and S131P). The dimer2 nucleotide sequence is provided in SEQ ID NO: 7 and FIG. 21. The dimer2 polypeptide is provided in SEQ ID NO: 6 and FIG. 22.

Construction of a Tandem Dimer of DsRed

In an attempt to produce a still further advantageous form of DsRed, an alternative novel strategy to synthesize a more stable DsRed dimer was devised. This approach utilized covalent tethering of two engineered monomeric DsRed units to yield a dimeric form of DsRed with advantageous properties. The basic strategy was to fuse two copies of an AC dimer with a polypeptide linker such that the critical dimer interactions could be satisfied through intramolecular contacts with the tandem partner encoded within the same polypeptide.

Based on the crystal structure of the DsRed tetramer (Yarbrough et al., *Proc. Natl. Acad. Sci. USA* 98:462–467 [2001]; and Wall et al., *Nature Struct. Biol.*, 7:1133–1138 [2000]), it was contemplated that a 10 to 20 residue linker could extend from the C-terminus of the A subunit to the N-terminus of the C subunit (~30 Å, see FIG. 1B), but not to the N-terminus of the B subunit (>70 Å). Using the optimized dimer2, a series of four tandem constructs were produced using linkers of varying lengths (9, 12, 13, or 22 amino acids) comprising a sequence similar to a known protease resistant linker (Whitlow et al. *Protein Eng*, 6:989–995 [1993]).

Of the four constructions, only the tandem construct with the 9 residue linker was notable for a somewhat slower maturation. The other three constructs were practically indistinguishable in this respect, and thus, find equal use with the present invention. The tandem dimer construct with the 12 residue linker, designated tdimer2(12), was used in all subsequent experiments. As expected, dimer2 and tdimer2 (12) have identical excitation and emission maximum and quantum yields (see FIG. 14). However, the extinction coefficient of tdimer2(12) is twice that of dimer2 due to the presence of two equally absorbing chromophores per polypeptide chain.

Evolution of a Monomeric DsRed

In an attempt to create improved dimers of DsRed would better tolerate disruption of the remaining interface, libraries were constructed where AC interface breaking mutations were incorporated into the tdimer(12). An initial dimer library was reassembled using a 3' primer that encoded the mutations H222G and F224G (FIG. 10A, library D5). These two residues form the bulk of the dimer contacts in the C-terminal tail of DsRed that hooks around the C-terminal tail of the dimer partner. From this library the best two unique clones, HF2Ga and HF2Gb, were very similar in sequence to dimer1 with the primary differences being the mutations F124L present in both clones, K163H in HF2 Gb and the H222G and F224G replacements. Both HF2Ga and HF2Gb migrated as fluorescent dimers when loaded unboiled onto a 12% SDS-PAGE gel so they must maintain a stable dimer interface.

Simultaneously, a more direct approach to breaking up the AC interface through introduction of dimer-breaking mutations was undertaken. Dimer1 was the template for the first such library (FIG. 10A, library M1) in which nine different positions were targeted, including two key AC interface residues, H162 and A164, which were substituted for lysine or arginine, respectively. The brightest colonies from this library were difficult to distinguish from the background red fluorescence of the *E. coli* colonies even after prolonged imaging with a digital camera. Suspect colonies were restreaked on LB/agar, allowed to mature at room temperature for two weeks and a crude protein preparation analyzed by SDS-PAGE. Imaging of the gel revealed a single faint band consistent with the expected mass of the monomer. Thus, this species was termed mRFP0.1 (for monomeric Red Fluorescent Protein). Sequencing of this clone revealed that mRFP0.1 was equivalent to dimer1 with mutations E144A, A145R, H162K, K163M, A164R, H222G and H224G.

Random mutagenesis on mRFP0.1 (FIG. 10A, library M2) resulted in the creation of the much brighter mRFP0.2, which gave an unambiguous red fluorescent and monomeric band by SDS-PAGE, and which contained the single additional mutation Y192C. Both mRFP0.1 and mRFP0.2 displayed at least 3-fold greater green fluorescence than red fluorescence, but as expected for the monomer, there was no FRET between the green and red components.

With the suspicion that mutations that were beneficial to the dimer could also benefit the monomer, a template mixture including mRFP0.2, dimer1.56, HF2Ga and HG2Gb was subjected to a combination of PCR-based template shuffling and directed mutagenesis (FIG. 10A, library M3). The top clone identified in this library, mRFP0.3 was relatively bright and had a greatly diminished green fluorescent component. In addition, mRFP0.3 was approximately 10 nm red shifted from DsRed and was primarily derived from dimer1.56.

The goal of the next directed library (FIG. 10B, library M4) was to investigate the effect of mutations at K83, which have previously been shown to cause a red shift in DsRed (Wall et al., *Nature Struct. Biol.*, 7:1133–1138 [2000]). The top two clones, designated mRFP0.4a and mRFP0.4b, contained the K83I or L mutation respectively, were 25 nm red shifted relative to DsRed and were very similar in terms of maturation rate and brightness. Unlike all the previous generations of the monomer, colonies of *E. coli* transformed with mRFP0.4a were red fluorescent within 12 h after transformation when excited with 540 nm light and viewed through a red filter.

A template mixture of mRFP0.4a and mRFP0.4b was subjected to random mutagenesis (FIG. 10B, library M5) and the resulting library was thoroughly screened. The 5 fastest maturing clones from this library were derived from mRFP0.4a and contained individual mutations L174P, V175A (two clones), F177C and F177S. The F177S clone or mRFP0.5a, appeared to mature slightly faster and had the smallest green peak in the absorbance spectra. One colony isolated from this library was exceptionally bright when grown on LB/agar but expressed very poorly when grown in liquid culture. This clone, designated mRFP0.5b, was derived from mRFP0.4b and contained two new mutations; L150M inside the barrel and V156A outside.

The next library (FIG. 10B, library M6) was intended to optimize the region around residues V175 and F177 in both mRFP0.5a and the increasingly divergent mRFP0.5b. The top clone in this library, designated mRFP0.6, was derived from mRFP0.5b, though of three other top clones, one was derived from mRFP0.5b, one from mRFP0.5a, and one appeared to have resulted from multiple crossovers between the two templates. The final library (FIG. 10B, library M7) targeted residues in the vicinity of L150 because this was the one remaining critical mutation that was derived from random mutagenesis and had not been reoptimized. Top clones had combinations of mutations at all targeted positions though the clone with the single mutation R153E was found to express slightly better in culture. This clone was further modified through deletion of the unnecessary V1a insertion and replacement of the cysteine at position 222 with a serine.

This final clone, designated mRFP1, contained a total of 33 mutations (see FIG. 1C) relative to wild-type DsRed. Of these mutations, 13 are internal to the β-barrel (N42Q, V44A, V71A, K83L, F124L, L150M, K163M, V175A, F177V, S179T, V195T, S197I and T217A). Of the 20 remaining external mutations, three are the aggregation reducing mutations from T1 (R2A, K5E and N6D), three are AB interface mutations (I125R, V127T and I180T), ten are AC interface mutations (R153E, H162K, A164R, L174D, Y192A, Y194K, H222S, L223T, F224G and L225A), and four additional mutations (T21S, H41T, C117E and V156A). The mRFP1 nucleotide and polypeptide sequences are provided in SEQ ID NOS: 9 and 8, respectively.

Initial evidence for the monomeric structure of mRFP1 and its precursors was based on SDS-PAGE results (see FIG.

Figure 3A:
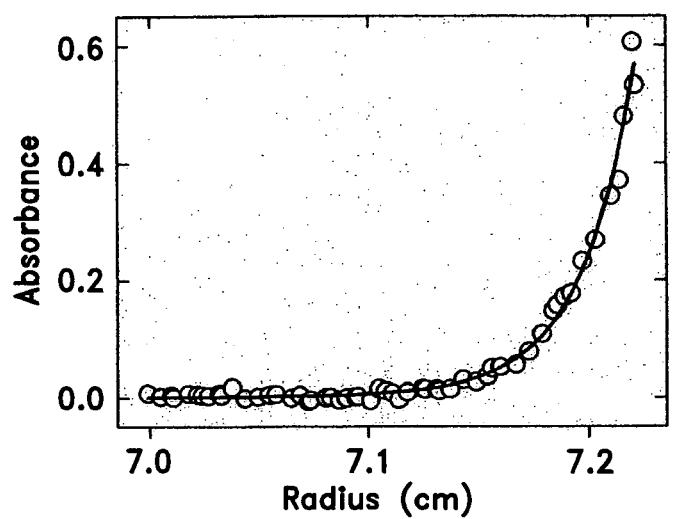
FIGS. 3A–3C show the results of an analytical ultracentrifugation analysis of DsRed, dimer2, and mRFP0.5a polypeptides, respectively. The equilibrium radial absorbance profiles at 20,000 rpm were modeled with a theoretical curve that allowed only the molecular weight to vary. The DsRed absorbance profile (FIG. 3A) was best fit with an apparent molecular weight of 120 kDa, consistent with a tetramer. The dimer2 absorbance profile (FIG. 3B) was best fit with an apparent molecular weight of 60 kDa, consistent with a dimer. The mRFP0.5a absorbance profile (FIG. 3C) was best fit with an apparent molecular weight of 32 kDa, consistent with a monomer containing an N-terminal polyhistidine affinity tag.
Figure 3B:
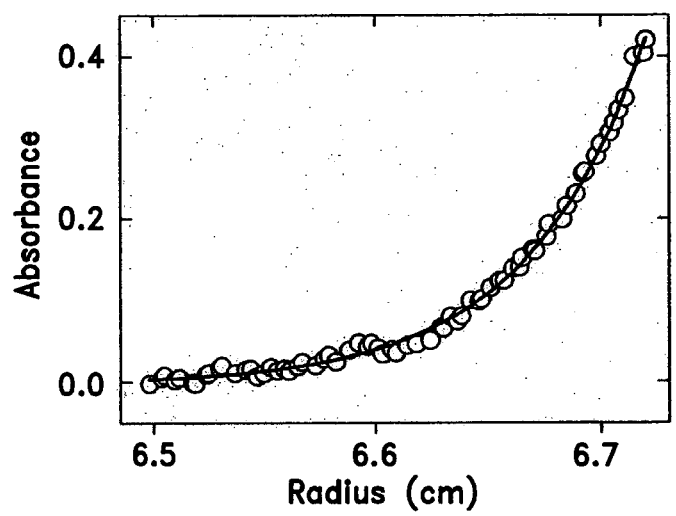
Figure 3C:
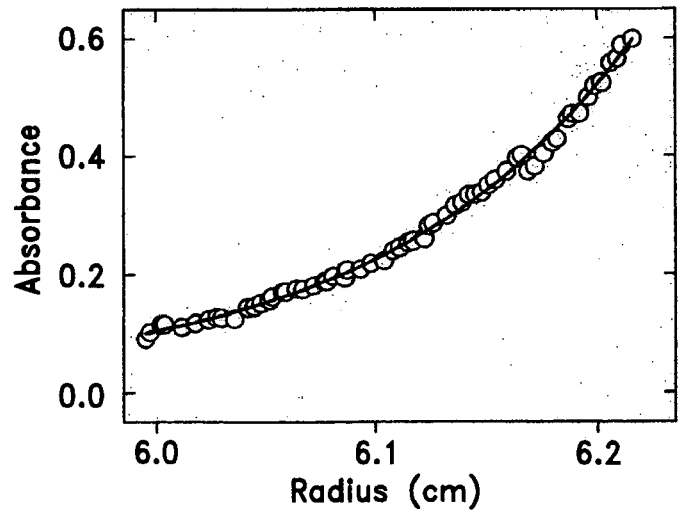

8) and the lack of FRET between the green and red fluorescent components in early generations. Thus analytical equilibrium ultracentrifugation was performed on DsRed, dimer2, and mRFP0.5a (an evolutionary precursor to mRFP1). The mRFP0.5a polypeptide sequence is illustrated in FIGS. 20A–20D. The analytical equilibrium analysis confirmed the expected tetramer, dimer, and monomer configurations of the tested species (see FIGS. 3A–3C).

Figure 4A:
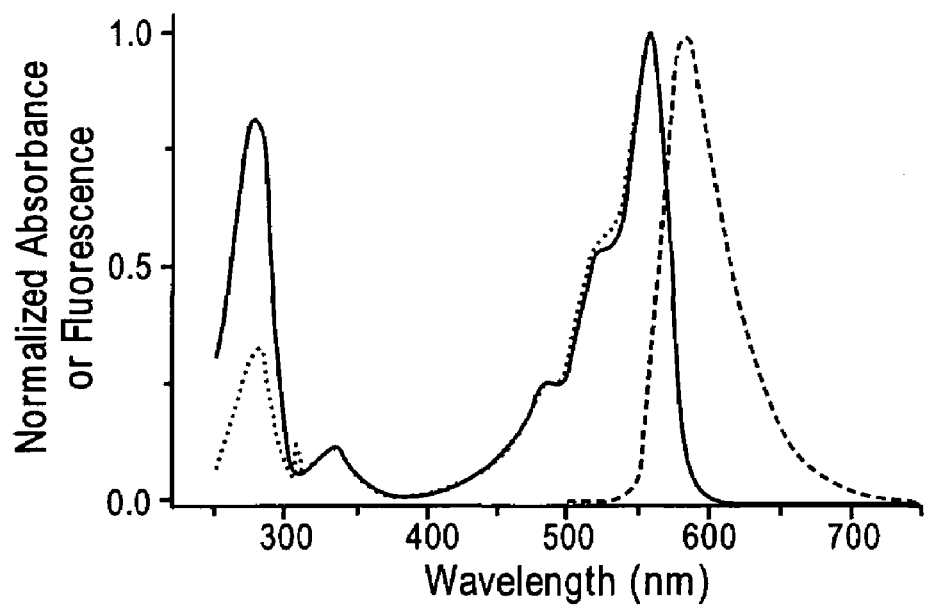
FIGS. 4A–4D show fluorescence and absorption spectra of DsRed, T1, dimer2 and tdimer2(12) and mRFP1, respectively. The absorbance spectrum is shown with a solid line, the excitation with a dotted line and the emission with a dashed line.
Figure 4B:
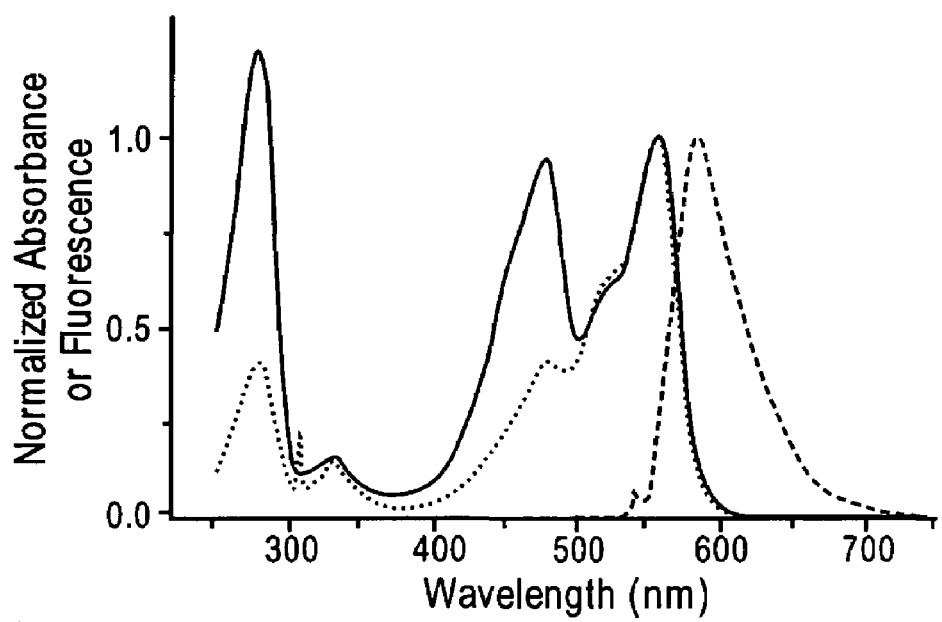
Figure 4C:
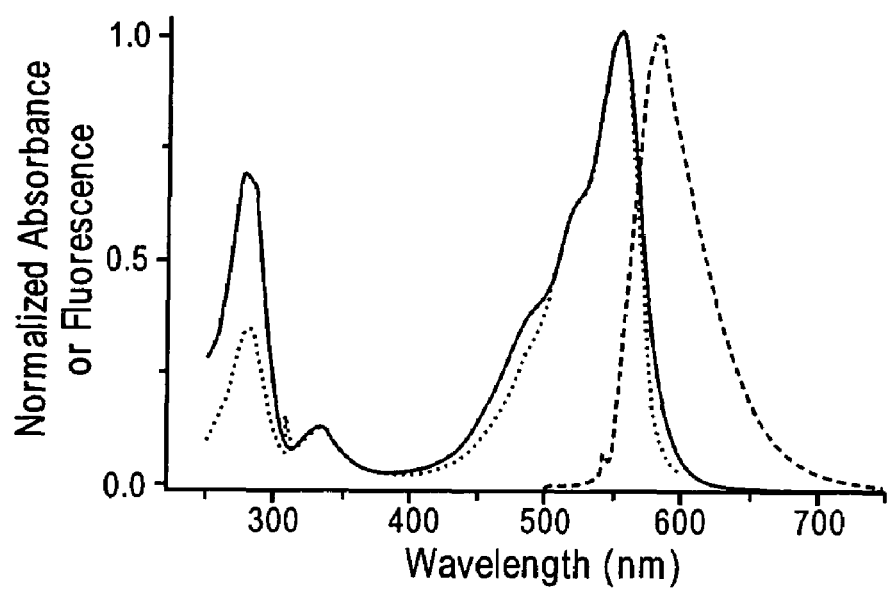
Figure 4D:
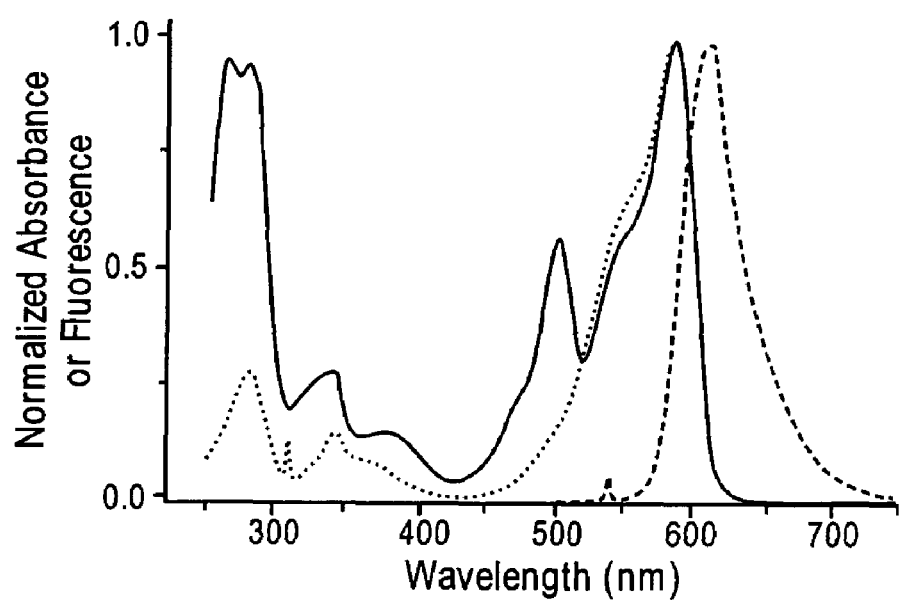

In a fluorescence and absorption spectra analysis, DsRed, T1 and dimer2 all have a fluorescent component that contributes at 475–486 nm to the excitation spectra due to FRET between oligomeric partners (see FIGS. 4A–4C). In this analysis, the T1 peak is quite pronounced (FIG. 4B), but in dimer2 (FIG. 4C), any excitation shoulder near 480 nm is almost obscured by the 5 nm blue-shifted excitation peak. The 25 nm red-shifted monomeric mRFP1 (FIG. 4D) also has a peak at 503 nm in the absorption spectra, but in contrast to the other variants, this species is non-fluorescent mutant and therefore does not show up in the excitation spectrum collected at any emission wavelength. When the 503 nm absorbing species is directly excited, negligible fluorescence emission is observed at any wavelength.

Figure 5:
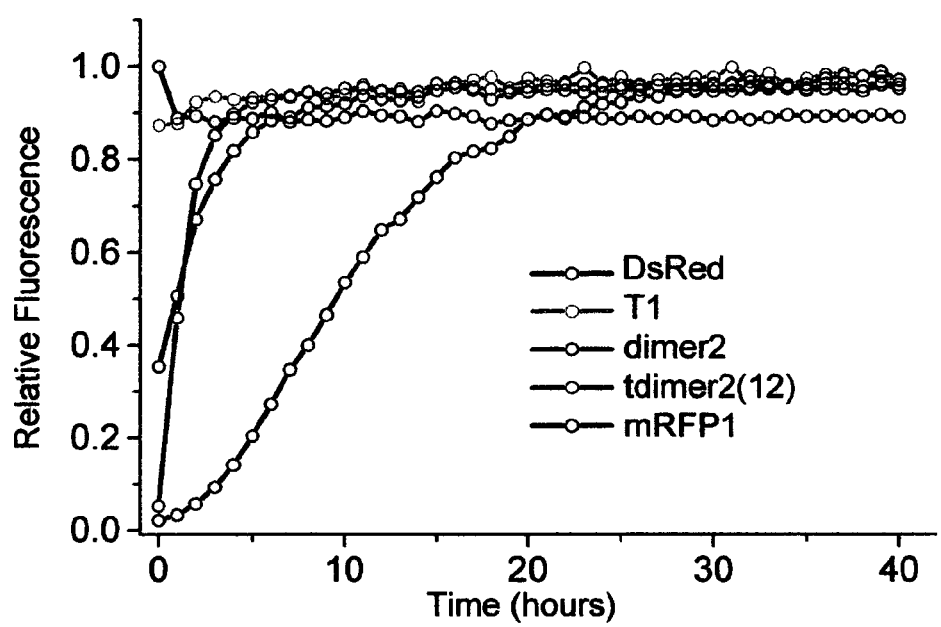
FIG. 5 shows a maturation time course of red fluorescence for DsRed, T1, dimer2, tdimer2(12) and mRFP1. The profiles are color coded, as indicated in the key. Log phase cultures of *E. coli* expressing the construct of interest were rapidly purified at 4° C. Maturation at 37° C. was monitored beginning at 2 hours post-harvest. The initial decrease in mRFP1 fluorescence is attributed to a slight quenching on warming from 4 to 37° C.
Figure 9:
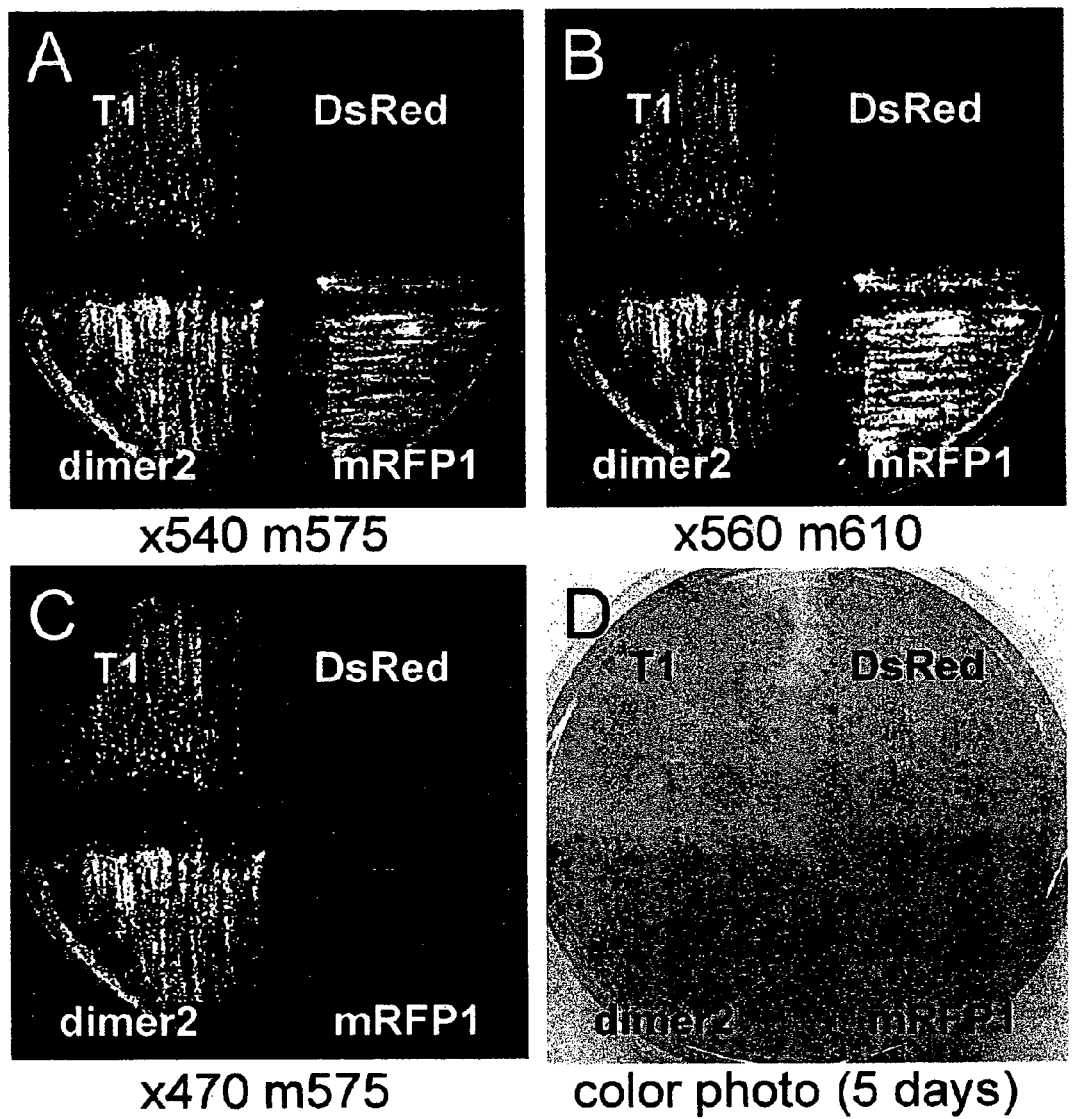
FIGS. 9A–9D show fluorescent images of red fluorescent proteins expressed in *E. coli*. *E. coli* strain JM109(DE3) was transformed with either DsRed, T1, dimer2 or mRFP1, plated on LB/agar supplemented with ampicillin, and incubated 12 hours at 37° C. then 8 hours at 20° C. before the plate was imaged with a digital camera.

As shown in FIG. 5, the rate of maturation of dimer2, tdimer2(12) and mRFP1 is greatly accelerated over that of DsRed, though only mRFP1 matures at least as quickly as T1. Based on data collected at 37° C., the $t_{0.5}$ for maturation of mRFP1 and T1 are less than 1 hour. $E.$ $coli$ colonies expressing either dimer2 or mRFP1 display similar or brighter levels of fluorescence to those expressing T1 after overnight incubation at 37° C. (see FIG. 9).

Expression of dimer2, tdimer2(12) and mRFP 1 in Mammalian Cells

The fluorescence of the dimer2, tdimer2(12) and mRFP1 proteins in the context of mammalian cells was tested. Mammalian expression vectors encoding dimer2, tdimer2 (12) and mRFP1 were expressed in transiently transfected HeLa cells. Within 12 hours the cells displayed strong red fluorescence evenly distributed throughout the nucleus and cytoplasm (data not shown).

Figure 6:
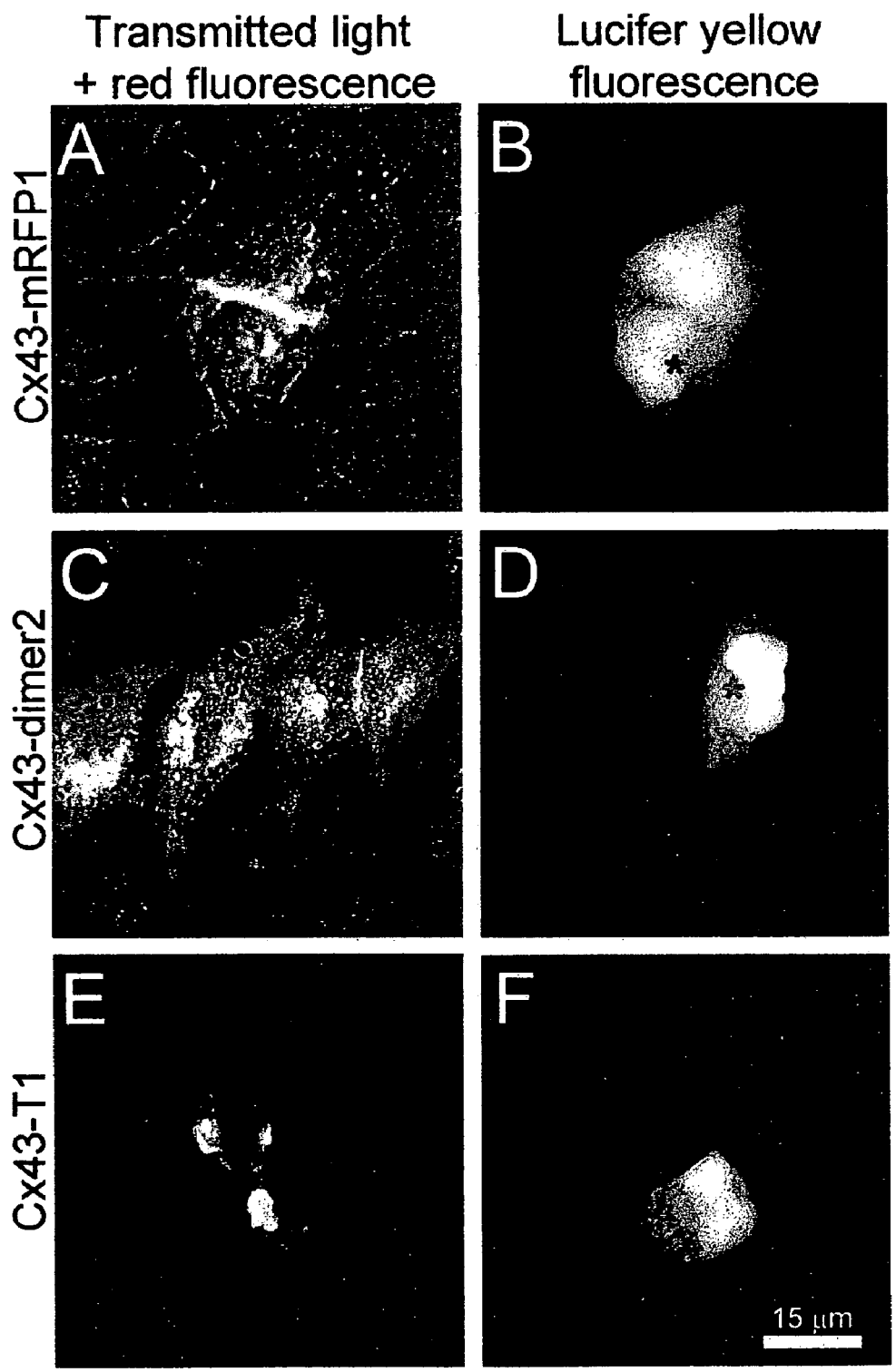
FIGS. 6A–6F show light and fluorescence microscopic images of HeLa cells expressing Cx43 fused with T1, dimer2 or mRFP1. Images 6A, 6C and 6E were acquired with excitation at 568 nm (55 nm bandwidth) and emission at 653 nm (95 nm bandwidth) with additional transmitted light. Luciferase (Lucifer) yellow fluorescence (images 6B, 6D and 6F) was acquired with excitation at 425 nm (45 nm bandpass) and emission at 535 nm (55 nm bandpass).

In view of this result, it was tested whether an RFP-fusion polypeptide could be created, where the RFP moiety retains its fluorescence, and where the fused polypeptide partner retains a native biological activity. This experiment was conducted using the gap junction protein connexin43 (Cx43), which could demonstrate the advantage of a monomeric red fluorescent protein if the fused Cx43 polypeptide retained its biological activity. A series of constructs consisting of Cx43 fused to either GFP, T1, dimer2, tdimer2(12) or mRFP1 were expressed in HeLa cells, which do not express endogenous connexins. Following transfection, the red fluorescence of the cells was observed with a fluorescence microscope. The results of this experiment are shown in FIGS. 6A, 6C and 6E. As previously reported (Lauf et al., $FEBS$ $Lett.$ 498:11–15 [2001]), the Cx43-GFP fusion protein was properly trafficked to the membrane and was assembled into functional gap junctions (data not shown), whereas the Cx43-DsRed tetramer (i.e., the T1 tetramer) consistently formed perinuclear localized red fluorescent aggregates (FIG. 6E). Both Cx43 -tdimer2(12) (not shown) and Cx43-dimer2 (FIG. 6C) were properly trafficked to the membrane though neither construct formed visible gap junctions. In contrast, the Cx43-mRFP1 construct behaved identically to Cx43-GFP and many red gap junctions were observed (FIG. 6A).

In another experiment, the transfected cells were microinjected with lucifer yellow to assess the functionality of the gap junctions (see FIGS. 6B, 6D and 6F; and FIG. 13). The Cx43-mRFP1 gap junctions rapidly and reliably passed dye (FIG. 6B), while neither Cx43-T1 transfected cells (FIG. 6E) nor non-transfected cells (not shown) passed dye. Both Cx43-dimer2 and Cx43-tdimer2(12) constructs slowly passed dye to a contacting transfected neighbor about one third of the time (FIG. 6D).

DISCUSSION

The monomeric mRFP1 simultaneously overcomes the three critical problems associated with the wild-type tetrameric form of DsRed. Specifically mRFP1 is a monomer, it matures rapidly, and it has minimal emission when excited at wavelengths optimal for GFP. These features make mRFP1 a suitable red fluorescent protein for the construction of fusion proteins and multi-color labeling in combination with GFP. As demonstrated with the gap junction forming protein Cx43, mRFP1 fusion proteins are functional and trafficked in a manner identical to their GFP analogues.

Although the extinction coefficient and fluorescence quantum yield result in reduced brightness of fully mature mRFP1 compared to DsRed, this is not an obstacle to use of mRFP1 in imaging experiments, as the reduced brightness is more than compensated for by the greater than 10-fold decrease in maturation time for mRFP1. Variant RFP polypeptides of the present invention, for example tdimer2 (12), also find use as FRET based sensors. This species is sufficiently bright, and displays FRET with all variants of Aequorea GFP (unpublished observations).

The present invention provides methods for the generation of still further advantageous RFP species. These methods use multistep evolutionary strategies involving one or multiple rounds of evolution with few mutational steps per cycle. These methods also find use in the converting of other oligomeric fluorescent proteins into advantageous monomeric or dimeric forms.

EXAMPLE 2

Preparation and Characterization of Fluorescent Protein Variants

This example demonstrates that mutations can be introduced into GFP spectral variants that reduce or eliminate the ability of the proteins to oligomerize.

ECFP (SEQ ID NO: 14) and EYFP-V68L/Q69K (SEQ ID NO: 12) at the dimer interface were subcloned into the bacterial expression vector $PRSET_B$ (Invitrogen Corp., La Jolla Calif.), creating an N-terminal $His_6$ tag on the of ECFP (SEQ ID NO: 14) and EYFP-V68L/Q69K (SEQ ID NO: 12), which allowed purification of the bacterially expressed proteins on a nickel-agarose (Qiagen) affinity column. All dimer-related mutations in the cDNAs were created by site-directed mutagenesis using the QuickChange mutagenesis kit (Stratagene), then expressed and purified in the same manner. All cDNAs were sequenced to ensure that only the desired mutations existed.

EYFP-V68L/Q69K (SEQ ID NO: 12) was mutagenized using the QuickChange kit (Stratagene). The overlapping mutagenic primers were designated "top" for the 5' primer and "bottom" for the 3' primer and are designated according to the particular mutation introduced (see TABLE 1). All primers had a melting temperature greater than 70° C. The mutations were made as close to the center of the primers as possible and all primers were purified by polyacrylamide gel electrophoresis. The primers are shown in a 5' to 3' orientation, with mutagenized codons underlined (TABLE 1).

TABLE 1

| Primer | Sequence | SEQ ID NO: |
|---|---|---|
| A206K top | CAG TCC AAG CTG AGC AAA GAC CCC AAC GAG AAG CGC GAT CAC | 25 |
| A206K bottom | GTG ATC GCG CTT CTC GTT GGG GTC TTT GCT CAG CTT GGA CTG | 26 |
| L221K top | CAC ATG GTC CTG AAG GAG TTC GTG ACC GCC GCC GGG | 27 |
| L221K bottom | CCC GGC GGC GGT CAC GAA CTC CTT CAG GAC CAT GTG | 28 |
| F223R top | CAC ATG GTC CTG CTG CGC GTG ACC GCC GCC GGG | 29 |
| F223R bottom | CCC GGC GGC GGT CAC GCG CTC CAG CAG GAC CAT GTG | 30 |
| L221K/F223 R top | CAC ATC GTC CTG AAG GAG CGC GTG ACC GCC GCC GGG | 31 |
| L221K/F223 R bottom | CCC GGC GGC GGT CAC GCG CTC CTT CAG GAC CAT GTG | 32 |

For protein expression, plasmids containing cDNAs for the various EYFP-V68L/Q69K (SEQ ID NO: 12) mutants were transformed into E. coli strain JM109 and grown to an $OD_{600}$ of 0.6 in LB containing 100 μg/ml ampicillin at which time they were induced with 1 mM isopropyl β-D-thiogalactoside. The bacteria were allowed to express the protein at room temperature for 6 to 12 hr, then overnight at 4° C., then were pelleted by centrifugation, resuspended in phosphate buffered saline (pH 7.4), and lysed in a French press. Bacterial lysates were cleared by centrifugation at 30,000×g for 30 min. The proteins in the cleared lysates were affinity-purified on Ni-NTA-agarose (Qiagen).

All GFPs used in these experiments were 238 amino acids in length. Subcloning the cDNAs encoding the GFPs into $PRSET_B$ resulted in the fusion of an additional 33 amino acids to the N-terminus of the GFPs. The sequence of this tag is MRGSHHHHHHGMASMTGGQQMGRDLYD-DDDKDP (SEQ ID NO: 22). Thus, the total length of the EYFP-V68L/Q69K (SEQ ID NO: 12) mutants expressed from this cDNA was 271 amino acids. The $His_6$ tag was removed using EKMax (Invitrogen) to determine if the associative properties measured for the GFPs were affected by the presence of the N-terminal $His_6$-tag. A dilution series of the enzyme and $His_6$-tagged GFP was made to determine the conditions necessary for complete removal of the $His_6$-tag. The purity of all expressed and purified proteins was analyzed by SDS-PAGE. In all cases, the expressed proteins were very pure, with no significant detectable contaminating proteins, and all were of the proper molecular weight. In addition, removal of the $His_6$ tag was very efficient, as determined by the presence of a single band migrating at the lower molecular weight than the $His_6$-EYFP- V68L/Q69K.

Spectrophotometric analysis of the purified proteins determined that there was no significant change in either the extinction coefficient as measured by chromophore denaturation (Ward et al., In "Green Fluorescent Protein. Properties, Applications and Protocols," eds. Chalfie and Kain, Wiley-Liss [1998]) or quantum yield (the standard used for EYFP-V68L/Q69K and the mutants derived therefrom was fluorescein) of these proteins with respect to EYFP-V68L/Q69K (SEQ ID NO: 12; "wtEYFP"; Table 2). Fluorescence spectra were taken with a Fluorolog spectrofluorimeter. Absorbance spectra of proteins were taken with a Cary UV-Vis spectrophotometer. Extinction coefficients were determined by the denatured chromophore method (Ward et al., In "Green Fluorescent Protein: Properties, Applications and Protocols," eds. Chalfie and Kain, Wiley-Liss [1998]).

TABLE 2

| Protein | Quantum Yield | Extinction Coefficient |
|---|---|---|
| WtEYFP | 0.71* | 62,000* |
| $His_6$ wtEYFP | 0.67 | 67,410 |
| $His_6$ wtEYFP L221K | 0.67 | 64,286 |
| $His_6$ wtEYFP F223R | 0.53 | 65,393 |
| $His_6$ wtEYFP A206K | 0.62 | 79,183 |

*published data (Cubitt et al., 1997)

To determine the degree of homoaffinity of the dimers, wtEYFP and the dimer mutants derived therefrom were subjected to sedimentation equilibrium analytical ultracentrifugation. Purified, recombinant proteins were dialyzed extensively against phosphate buffered saline (pH 7.4), and 125 μl samples of protein at concentrations ranging from 50 μM to 700 μM were loaded into 6-channel centrifugation cells with EPON centerpieces. Samples were blanked against the corresponding dialysis buffer. Sedimentation equilibrium experiments were performed on a Beckman Optima XL-I analytical ultracentrifuge at 20° C. measuring radial absorbance at 514 nm. Each sample was examined at three or more of the following speeds: 8,000 rpm, 10,000 rpm, 14,000 rpm, and 20,000 rpm. Periodic absorbance measurements at each speed ensured that the samples had reached equilibrium at each speed.

The data were analyzed globally at all rotor speeds by nonlinear least-squares analysis using the software package (Origin) supplied by Beckman. The goodness of fit was evaluated on the basis of the magnitude and randomness of the residuals, expressed as the difference between the experimental data and the theoretical curve and also by checking each of the tit parameters for physical reasonability. The molecular weight and partial specific volume of each protein were determined using Sedenterp v 1.01, and the data were factored into the equation for the determination of homoaffinity (TABLE 3). In addition, dissociation constants ($K_d$) derived from the data generated by analytical ultracentrifugation are shown for some proteins (TABLE 4).

TABLE 3

| Mutant | Molecular Weight | Partial Specific Volume |
|---|---|---|
| wtEYFP | 26796.23 | 0.7332 |
| $His_6$ wtEYFP | 30534.26 | 0.7273 |
| $His_6$ EYFP A206K | 30593.37 | 0.7277 |

TABLE 3-continued

| Mutant | Molecular Weight | Partial Specific Volume |
|---|---|---|
| EYFP L221K | 30551.29 | 0.7270 |
| His$_6$ EYFP L221K | 30549.27 | 0.7271 |
| His$_6$ EYFP F223R | 30543.27 | 0.7270 |
| His$_6$ EYFP L221K/F223R | 30560.30 | 0.7267 |

TABLE 4

| Protein | K$_d$ (mM) |
|---|---|
| His$_6$ wtEYFP | 0.11 |
| His$_6$ wtEYFP L221K | 9.7 |
| His$_6$ wtEYFP F223R | 4.8 |
| His$_6$ wtEYFP A206K | 74 |
| His$_6$ wtEYFP L221K/F223R | 2.4 |

For experiments in living cells, ECFP (SEQ ID NO: 14; "wtECFP") and EYFP-V68L/Q69K (SEQ ID NO: 12; "wtEYFP") targeted to the plasma membrane (PM) were subcloned into the mammalian expression vector, pcDNA3 (Invitrogen Corp.) and mutagenized and sequenced as described above. Targeting of the GFP variants to the PM was accomplished by making either N-terminal or C-terminal fusions of the GFP variant to short peptides containing a consensus sequence for acylation and/or prenylation (post-translational lipid modifications). The cDNAs of the PM targeted GFP variants were transfected and expressed in either HeLa cells or MDCK cells, and the expression pattern and degree of association were determined using fluorescent microscopy. FRET efficiency was measured to determine the degree of interaction of the PM-ECFP and PM-EYFP-V68L/Q69K. Analysis of the interactions by the FRET donor-dequench method (Miyawaki and Tsien, supra, 2000) demonstrated that the wtECFP and wtEYFP interacted in a manner that was dependent upon the association of the wtECFP and wtEYFP, and that this interaction was effectively eliminated by changing the amino acids in the hydrophobic interface to any one or a combination of the mutations A206K, L221K and F223R.

These results demonstrate that the solution oligomeric state of Aequorea GFP and its spectral variants, and dimer mutants derived therefrom, were accurately determined by analytical ultracentrifugation. The ECFP (SEQ ID NO: 14) and EYFP-V68L/Q69K (SEQ ID NO: 12) GFP spectral variants formed homodimers with a fairly high affinity of about 113 µM. By using site directed mutagenesis, the amino acid composition was altered so as to effectively eliminate dimerization and the cell biological problems associated with it. Thus, the modified fluorescent proteins provide a means to use FRET to measure the associative properties of host proteins fused to the modified CFP or YFP. The ambiguity and potential for false positive FRET results associated with ECFP (SEQ ID NO: 14) and EYFP-V68L/Q69K (SEQ ID NO: 12) dimerization have been effectively eliminated, as has the possibility of misidentification of the subcellular distribution or localization of a host protein due to dimerization of GFPs.

The Renilla GFP and the Discosoma red fluorescent protein are obligate oligomers in solution. Because it was generally believed that Aequorea GFP could also dimerize in solution, and because GFP crystallizes as a dimer, the present investigation was designed to characterize the oligomeric state of GFP. The crystallographic interface between the two monomers included many hydrophilic contacts as well as several hydrophobic contacts (Yang et al., supra, 1996). It was not immediately clear, however, to what degree each type of interaction contributed to the formation of the dimer in solution.

As disclosed herein, the extent of GFP self-association was examined using sedimentation equilibrium, analytical ultracentrifugation, which is very useful for determining the oligomeric behavior of molecules both similar (self associating homomeric complexes) and dissimilar (heteromeric complexes; see Laue and Stafford, Ann. Rev. Biophys. Biomol. Struct. 28:75–100, 1999). In contrast to X-ray crystallography, the experimental conditions used in the analytical ultracentrifugation experiments closely approximated cellular physiological conditions. Monomer contact sites identified by X-ray crystallography within a multimeric complex are not necessarily the same as those in solution. Also in contrast to analytical ultracentrifugation, X-ray crystallography alone cannot provide definitive information about the affinity of the complex. The results of this investigation demonstrate that replacement of the hydrophobic residues A206, L221 and F223 with residues containing positively charged side chains (A206K, L221K and F223R) eliminated dimerization as determined by analytical ultracentrifugation in vitro and by analysis of the concentration dependence of FRET in intact cells.

EXAMPLE 3

Characterization Of The Coral Red Fluorescent Protein, DsRed, And Mutants Thereof This example describes the initial biochemical and biological characterization of DsRed and DsRed mutants.

The coding sequence for DsRed was amplified from pDsRed-N1 (Clontech Laboratories) with PCR primers that added an N terminal BamHI recognition site upstream of the initiator Met codon and a C terminal Eco RI site downstream of the STOP codon. After restriction digestion, the PCR product was cloned between the Bam HI and Eco RI sites of PRSET$_B$ (Invitrogen), and the resulting vector was amplified in DH5α bacteria. The resulting plasmid was used as a template for error-prone PCR (Heim and Tsien, Curr. Biol. 6:178–182, 1996, which is incorporated herein by reference) using primers that were immediately upstream and downstream of the DsRed coding sequence, theoretically allowing mutation of every coding base, including the initiator Met. The mutagenized PCR fragment was digested with Eco RI and Bam HI and recloned into PRSET$_B$. Alternatively, the Quick-Change mutagenesis kit (Stratagene) was used to make directed mutations on the pRSET$_B$-DsRed plasmid.

In both random and directed mutagenesis studies, the mutagenized plasmid library was electroporated into JM109 bacteria, plated on LB plates containing ampicillin, and screened on a digital imaging device (Baird et al., Proc. Natl. Acad. Sci., USA 96:11242–11246, 1999, which is incorporated herein by reference). This device illuminated plates with light from a 150 Watt xenon arc lamp, filtered through bandpass excitation filters and directed onto the plates with two fiber optic bundles. Fluorescence emission from the plates was imaged through interference filters with a cooled CCD camera. Images taken at different wavelengths could be digitally ratioed using MetaMorph software (Universal Imaging) to allow identification of spectrally shifted mutants. Once selected, the mutant colonies were picked by hand into LB/Amp medium, after which the culture was used for protein preparation or for plasmid preparations. The DsRed mutant sequences were analyzed with dye-terminator dideoxy sequencing.

DsRed and its mutants were purified using the N-terminal polyhistidine tag (SEQ ID NO: 22; see Example 1) provided by the PRSET$_B$ expression vector (see Baird et al., supra, 1999). The proteins were microconcentrated and buffer exchanged into 10 mM Tris (pH 8.5) using a Microcon-30 (Amicon) for spectroscopic characterization. Alternatively, the protein was dialyzed against 10 mM Tris (pH 7.5) for oligomerization studies because microconcentration resulted in the production of large protein aggregates. To test for light sensitivity of protein maturation, the entire synthesis was repeated in the dark, with culture flasks wrapped in foil, and all purification was performed in a room that was dimly lit with red lights. There was no difference in protein yield or color when the protein was prepared in light or dark.

Numbering of amino acids conforms to the wild type sequence of drFP583 (DsRed; Matz et al., *Nature Biotechnology* 17:969–973 [1999]), in which residues 66–68, Gln-Tyr-Gly, are homologous to the chromophore-forming residues (65–67, Ser-Tyr-Gly) of GFP. The extra amino acid introduced by Clontech after the initiator Met was numbered "1a" and the residues of the N-terminal polyhistidine tag were numbered $^-33$ to $^-1$.

Fluorescence spectra were taken with a Fluorolog spectrofluorimeter. Absorbance spectra of proteins were taken with a Cary UV-Vis spectrophotometer. For quantum yield determination, the fluorescence of a solution of DsRed or DsRed K83M in phosphate buffered saline was compared to equally absorbing solutions of Rhodamine B and Rhodamine 101 in ethanol. Corrections were included in the quantum yield calculation for the refractive index difference between ethanol and water. For extinction coefficient determination, native protein absorbance was measured with the spectrophotometer, and protein concentration was measured by the BCA method (Pierce).

The pH sensitivity of DsRed was determined in a 96 well format by adding 100 $\mu$L of dilute DsRed in a weakly buffered solution to 100 $\mu$L of strongly buffered pH solutions in triplicate (total 200 $\mu$L per well) for pH 3 to pH 12. The fluorescence of each well was measured using a 525–555 nm bandpass excitation filter and a 575 nm long pass emission filter. After the 96 well fluorimeter measurements were taken, 100 $\mu$L of each pH buffered DsRed solution was analyzed on the spectrofluorimeter to observe pH-dependent spectral shape changes. For time-trials of DsRed maturation, a dilute solution of freshly synthesized and purified DsRed was made in 10 mM Tris (pH 8.5), and this solution was stored at room temperature in a stoppered cuvette (not airtight) and subjected to periodic spectral analysis. For mutant maturation data, fluorescence emission spectra (excitation at 475 nm or 558 nm) were taken directly after synthesis and purification, and then after more than 2 months storage at 4° C. or at room temperature.

Quantum yields for photodestruction were measured separately on a microscope stage or in a spectrofluorimeter. Microdroplets of aqueous DsRed solution were created under oil on a microscope slide and bleached with 1.2 W/cm$^2$ of light through a 525–555 nm bandpass filter. Fluorescence over time was monitored using the same filter and a 563–617 nm emission filter. For comparison, EGFP (containing mutations F64L, S65T; SEQ ID NO: 13) and EYFP-V68L/Q69K (also containing mutations S65G, S72A, T203Y; SEQ ID NO: 12) microdroplets were similarly bleached with 1.9 W/cm$^2$ at 460–490 nm while monitoring at 515–555 and 523–548 nm, respectively.

For the spectrofluorimeter bleaching experiment, a solution of DsRed was prepared in a rectangular microcuvette and overlaid with oil so that the entire 50 $\mu$L of protein solution resided in the 0.25 cm×0.2 cm×1 cm illumination volume. The protein solution was illuminated with 0.02 W/cm$^2$ light from the monochromator centered at 558 nm (5 nm bandwidth). Fluorescence over time was measured at 558 nm excitation (1.25 nm bandwidth) and 583 nm emission. Quantum yields ($\Phi$) for photobleaching were deduced from the equation $\Phi=(\gamma^{-1}t_{90\%})^{-1}$, where $\epsilon$ is the extinction coefficient in cm$^2$ mol$^{-1}$, I is the intensity of incident light in einsteins cm$^{-2}$s$^{-1}$ and $t_{90\%}$ is the time in seconds for the fluorophore to be 90% bleached (Adams et al., *J. Am. Chem. Soc.* 110:3312–3320, 1988, which is incorporated herein by reference).

Polyhistidine-tagged DsRed, DsRed K83M and wild type Aequorea GFP (SEQ ID NO: 2) were run on a 15% polyacrylamide gel without denaturation. To prevent denaturation, protein solutions (in 110 mM Tris HCl, pH 7.5) were mixed 1:1 with 2×SDS-PAGE sample buffer (containing 200 mM dithiothreitol) and loaded directly onto the gel without boiling. A broad range pre-stained molecular weight marker set (BioRad) was used as a size standard. The gel was then imaged on an Epson 1200 Perfection flatbed scanner.

Purified recombinant DsRed was dialyzed extensively against phosphate buffered saline (pH 7.4) or 10 mM Tris, 1 mM EDTA (pH 7.5). Sedimentation equilibrium experiments were performed on a Beckman Optima XL-I analytical ultracentriftige at 20° C. measuring absorbance at 558 nm as a function of radius. 125 $\mu$L samples of DsRed at 3.57 $\mu$M (0.25 absorbance units) were loaded into 6 channel cells. The data were analyzed globally at 10,000, 14,000, and 20,000 rpm by nonlinear least-squares analysis using the Origin software package (Beckman). The goodness of fit was evaluated on the basis of the magnitude and randomness of the residuals, expressed as the difference between the experimental data and the theoretical curve and also by checking each of the fit parameters for physical reasonability.

FRET between immature green and mature red DsRed was examined in mammalian cells. DsRed in the vector pcDNA3 was transfected into HeLa cells using Lipofectin, and 24 hr later the cells were imaged on a fluorescence microscope. The fluorescences of the immature green species (excitation 465–495 nm, 505 nm dichroic, emission 523–548 nm) and of mature red protein (excitation 529–552 nm, 570 nm dichroic, emission 563–618 nm) were measured with a cooled CCD camera. These measurements were repeated after selective photobleaching of the red component by illumination with light from the xenon lamp, filtered only by the 570 nm dichroic, for cumulative durations of 3, 6, 12, 24, and 49 min. By the final time, about 95% of the initial red emission had disappeared, whereas the green emission was substantially enhanced.

Yeast two hybrid assays were also performed. The DsRed coding region was cloned in-frame downstream of the Gal4 activation domains (the "bait"; amino acid residues 768–881) and DNA binding domains (the "prey"; amino acid residues 1–147) in the pGAD GH and pGBT9 vectors, respectively (Clontech). These DsRed two hybrid plasmids were transformed into the HF7C strain of *S. cerevisiae*, which cannot synthesize histidine in the absence of interaction between the proteins fused to the Gal4 fragments. Yeast containing both DsRed-bait and DsRed-prey plasmids were streaked on medium lacking histidine and assayed for growth by visually inspecting the plates. Alternatively, the yeast were grown on filters placed on plates lacking tryptophan and leucine to select for the bait and prey plasmids. After overnight growth, the filters were removed from the plates, frozen in liquid nitrogen, thawed, and incubated in X-gal overnight at 30° C. and two days at 4° C. to test for β-galactosidase activity (assayed by blue color development). In both the β-galactosidase and histidine growth assays, negative controls consisted of yeast containing bait and prey plasmids, but only the bait or the prey was fused to DsRed.

Surprisingly, DsRed took days at room temperature to reach full red fluorescence. At room temperature, a sample of purified protein initially showed a major component of green fluorescence (excitation and emission maxima at 475 and 499 nm, respectively), which peaked in intensity at about 7 hr and decreased to nearly zero over two days. Meanwhile, the red fluorescence reached half its maximal fluorescence after approximately 27 hr and required more than 48 hr to reach greater than 90% of maximal fluorescence (see Baird et al., supra, 2000).

Fully matured DsRed had an extinction coefficient of 75,000 $M^{-1}cm^{-1}$ at its 558 nm absorbance maximum and a fluorescence quantum yield of 0.7, which is much higher than the values of 22,500 $M^{-1}cm^{-1}$ and 0.23 previously reported (Matz et al., *Nature Biotechnology* 17:969–973 [1999]). These properties make mature DsRed quite similar to rhodamine dyes in wavelength and brightness. Unlike most GFP variants, DsRed displayed negligible (<10%) pH-dependence of absorbance or fluorescence from pH 5 to 12. (see Baird et al., supra, 2000). However, acidification to pH 4–4.5 depressed both the absorbance and excitation at 558 nm relative to the shorter wavelength shoulder at 526 nm, whereas the emission spectrum was unchanged in shape. DsRed was also relatively resistant to photobleaching. When exposed to a beam of 1.2 $W/cm^2$ of approximately 540 nm light in a microscope stage, microdroplets of DsRed under oil took 1 hr to bleach 90%, whereas 20 $mW/cm^2$ of 558 nm light in a spectrofluorimeter microcuvette required 83 hr to bleach 90%. The microscope and fluorimeter measurements, respectively, gave photobleach quantum efficiencies of $1.06 \times 10^{-6}$ and $4.8 \times 10^{-7}$ (mean of $7.7 \times 10^{-7}$). Analogous microscope measurements of EGFP (S65T; SEQ ID NO: 13) and EYFP-V68L/Q69K (SEQ ID NO: 12; including Q69K) gave $3 \times 10^{-6}$ and $5 \times 10^{-5}$, respectively.

In an effort to examine the nature of the red chromophore and to identify DsRed variants useful as biological indicators, DsRed was mutagenized randomly and at specific sites predicted by sequence alignment with GFP to be near the chromophore. Many mutants that matured more slowly or not at all were identified, but none were identified that matured faster than DsRed. Screening of random mutants identified mutants that appeared green or yellow, which was found to be due to substitutions K83E, K83R, S197T, and Y120H. The green fluorescence was due to a mutant species with excitation and emission maxima at 475 and 500 nm, respectively, whereas the yellow was due to a mixture of this green species with DsRed-like material, rather than to a single species at intermediate wavelengths.

The DsRed K83R mutant had the lowest percentage conversion to red, and proved very useful as a stable version of the immature green-fluorescing form of DsRed (see Baird et al., supra, 2000). Further directed mutagenesis of K83 yielded more green and yellow mutants that were impaired in chromophore maturation. In many of the K83 mutants that matured slowly and incompletely, the red peak was at longer wavelengths than DsRed. K83M was particularly interesting because its final red-fluorescing species showed a 602 nm emission maximum, with relatively little residual green fluorescence and a respectable quantum yield, 0.44. However, its maturation was slower than that of the wild type DsRed. Y120H had a red shift similar to that of K83M and appeared to produce brighter bacterial colonies, but also maintained much more residual green fluorescence.

Spectroscopic data of the DsRed mutants are shown in FIG. 15. In this FIG., "maturation" of protein refers to the rate of appearance of the red fluorescence over the two days after protein synthesis. Because some maturation occurs during the synthesis and purification (which take 1–2 days), numerical quantification is not accurate. A simple +/−rating system was used, wherein (−−) means very little change, (−) means a 2–5 fold increase in red fluorescence, (+) means 5–20 fold increase, and (++) indicates the wild type increase (approximately 40 fold). The red/green ratio was determined two months after protein synthesis by dividing the peak emission fluorescence obtained at 558 nm excitation by the 499 nm fluorescence obtained at 475 nm excitation from the same sample. This does not represent a molar ratio of the two species because the ratio does not correct for differences in extinction coefficient or quantum yields between the two species, or the possibility of FRET between the two species if they are in a macromolecular complex.

To determine whether Lys70 or Arg95 can form imines with the terminal carbonyl of a GFP-like chromophore (see Tsien, *Nature Biotechnol.*, 17:956–957, 1999), DsRed mutants K70M, K70R, and R95K were produced. K70M remained entirely green with no red component, whereas K70R matured slowly to a slightly red-shifted red species. The spectral similarity of K70R to wild type DsRed argues against covalent incorporation of either amino acid into the chromophore. No fluorescence at any visible wavelength was detected from R95K, which might be expected because Arg95 is homologous to Arg96 of GFP, which is conserved in all fluorescent proteins characterized to date (Matz et al., *Nature Biotechnology* 17:969–973 [1999]). The failure of R95K to form a green chromophore prevented testing whether Arg95 was also required for reddening.

In view of the propensity of Aequorea GFP to form dimers at high concentrations in solution and in some crystal forms, and the likelihood that *Renilla* GFP forms an obligate dimer (Ward et al., In *"Green Fluorescent Protein: Properties, Applications and Protocols,"* eds. Chalfie and Kain, Wiley-Liss [1998]), the ability of DsRed to oligomerize was examined. Initial examination of the expressed proteins by SDS-PAGE suggested that aggregates formed, in that poly-histidine-tagged proteins DsRed and DsRed K83R migrated as red and yellow-green bands, respectively, at an apparent molecular weight of greater than 110 kDa when mixed with 200 mM DTT and not heated before loading onto the gel (see Baird et al., supra, 2000). In comparison, Aequorea GFP, when treated similarly, ran as a fluorescent green band near its predicted monomer molecular weight of 30 kDa. The high molecular weight DsRed band was not observed when the sample was briefly boiled before electrophoresis (see Gross et al., supra, 2000). Under these conditions, a band near the predicted monomer molecular weight of 30 kDa predominated and was colorless without Coomassie staining.

To determine the oligomerization status more rigorously, the DsRed protein was subjected to analytical equilibrium centrifugation (Laue and Stafford, supra, 1999). Global curve fitting of the absorbance data determined from the radial scans of equilibrated DsRed indicated that DsRed exists as an obligate tetramer in solution (Baird et al., supra, 2000), in both low salt and physiological salt concentrations. When the data was modeled with a single-species tetramer, the fitted molecular weight was 119,083 Da, which is in excellent agreement with the theoretical molecular weight of 119,068 Da for the tetramer of polyHis-tagged DsRed. Attempts to fit the curves with alternative stoichiometries from monomer to pentamer failed to converge or gave unreasonable values for the floating variables and large, non-random residuals. The residuals for the tetramer fit were much smaller and more randomly distributed, but were somewhat further improved by extending the model to allow the obligate tetramer to dimerize into an octamer, with a fitted dissociation constant of 39 $\mu M$. Thus the 558-nm-absorbing species appears to be tetrameric over the range of monomer concentrations from 14 $\mu M$ to 11 $\mu M$ in vitro. The hint of octamer formation at the highest concentrations is only suggestive because the highest concentrations of tetramer achieved in the ultracentrifugation cell remained more than an order of magnitude below the fitted dissociation constant.

To confirm whether DsRed also oligomerizes in live cells, FRET analysis was performed in mammalian cells and in two hybrid assays in yeast cells. HeLa cells were transfected with wild type DsRed and imaged 24 hr later, when they contained a mixture of the immature green intermediate and the final red form. The green fluorescence was monitored intermittently before and during selective photobleaching of the red species over 49 min of intense orange illumination. If the two proteins were non-associated, bleaching the red species would be expected to have no effect on the green fluorescence. In fact, however, the green fluorescence increased by 2.7 to 5.8 fold in different cells, corresponding to FRET efficiencies of 63% to 83%. These values equal or surpass the highest FRET efficiencies ever observed between GFP mutants, 68% for cyan and yellow fluorescent proteins linked by a zinc ion-saturated zinc finger domain (Miyawaki and Tsien, supra, 2000).

Additional evidence of in vivo oligomerization was provided by the directed yeast two hybrid screen. When DsRed fusions to the Gal4 DNA binding domain and activation domain were expressed in HF7C yeast, the yeast demonstrated a his$^+$ phenotype and were able to grow without supplemental histidine, indicating a two hybrid interaction had occurred. Neither fusion construct alone (DsRed-DNA binding domain or DsRed-activation domain) produced the his$^+$ phenotype, indicating that a DsRed-DsRed interaction, and not a non-specific DsRed-Gal4 interaction, was responsible for the positive result. In addition, the his$^+$ yeast turned blue when lysed and incubated with X-gal, suggesting that the DsRed-DsRed interaction also drove transcription of the θ-galactosidase gene. Thus, two separate transcriptional measurements of the yeast two hybrid assay confirmed that DsRed associates in vivo.

This investigation of DsRed revealed a that DsRed as desirable properties, as well as some nonoptimal properties, with respect to its being useful to complement or as an alternative to GFPs. The most important favorable property identified was that DsRed has a much higher extinction coefficient and fluorescence quantum yield (0.7) than was previously reported, such that the fluorescence brightness of the mature well-folded protein is comparable to rhodamine dyes and to the best GFPs.

DsRed also is quite resistant to photobleaching by intensities typical of spectrofluorimeters (mW/cm$^2$) or microscopes with arc lamp illumination and interference filters (W/cm$^2$), showing a photobleaching quantum yield on the order of 7×10$^{-7}$ in both regimes. This value is significantly better than those for two of the most popular green and yellow GFP mutants, EGFP (3×10$^{-6}$) and EYFP-V68L/Q69K (5×10$^{-5}$). The mean number of photons that a single molecule can emit before photobleaching is the ratio of the fluorescence and photobleaching quantum yields, or 1×10$^6$, 2×10$^5$, and 1.5×10$^4$ for DsRed, EGFP, and EYFP-V68L/Q69K, respectively. A caveat is that the apparent photobleaching quantum yield might well increase at higher light intensities and shorter times if the molecule can be driven into dark states such as triplets or tautomers from which it can recover its fluorescence. GFPs usually show a range of such dark states (Dickson et al., *Nature* 388: 355–358, 1997; Schwille et al., *Proc. Natl. Acad. Sci., USA* 97:151–156, 2000), and there is no reason to expect that DsRed will be any simpler. The photobleaching measurements described herein were made over minutes to hours, and include ample time for such recovery. In contrast, fluorescence correlation spectroscopy and flow cytometry monitor single passages of molecules through a focused laser beam within microseconds to milliseconds, such that temporary dark states that last longer than the transit time count as photobleaching, raising the apparent quantum yield for bleaching. Techniques such as laser scanning confocal microscopy, in which identified molecules are repetitively scanned, will show intermediate degrees of photobleaching depending on the time scale of illumination and recovery.

Another desirable feature of DsRed is its negligible sensitivity to pH changes over the wide range (pH 4.5 to 12). The currently available brighter GFP mutants are more readily quenched than DsRed by acidic pH. Such pH sensitivity can be exploited under controlled conditions to sense pH changes, especially inside organelles or other specific compartments (see Llopis et al., *Proc. Natl. Acad. Sci., USA* 95:6803–6808, 1998), although this feature can cause artifacts in some applications.

DsRed mutants such as K83M demonstrate that DsRed can be pushed to longer wavelengths (564 and 602 nm excitation and emission maxima), while retaining adequate quantum efficiency (0.44). The 6 nm and 19 nm bathochromic shifts correspond to 191 cm$^{-1}$ and 541 cm$^{-1}$ in energy, which are of respectable magnitude for a single amino acid change that does not modify the chromophore. A homolog of DsRed recently cloned from a sea anemone has an absorbance maximum at 572 nm and extremely weak emission at 595 nm with quantum yield <0.001; one mutant had an emission peak at 610 m but was very dim and slow to mature (Lukyanov et al., *J. Biol. Chem.* 275:25879–25882, 2000, which is incorporated herein by reference).

Less desirable features of DsRed include its slow and incomplete maturation, and its capacity to oligomerize. A maturation time on the order of days precludes a use of DsRed as a reporter for short term gene expression studies and for applications directed to tracking fusion proteins in organisms that have short generation times or fast development. Since maturation of GFPs was considerably accelerated by mutagenesis (Heim et al., *Nature* 373:663–664, 1995, which is incorporated herein by reference), DsRed similarly can be mutagenized and variants having faster maturation times can be isolated.

Because the Lys83 mutants all permitted at least some maturation, it is unlikely that the primary amine plays a direct catalytic role for this residue, a suggestion supported by the observation that the most chemically conservative replacement, Lys to Arg, impeded red development to the greatest extent. Ser197 provided a similar result, in that the most conservative possible substitution, Ser to Thr, also significantly slowed maturation. Mutations at the Lys83 and Ser197 sites appeared several times independently in separate random mutagenesis experiments and, interestingly, Lys83 and Ser197 are replaced by Leu and Thr, respectively, in the highly homologous cyan fluorescent protein dsFP483 from the same *Discosoma* species. Either of the latter two mutations could explain why dsFP483 never turns red. Residues other than Lys83 and Ser197 also affected maturation to the red.

The multimeric nature of DsRed was demonstrated by four separate lines of evidence, including slow migration on SDS-PAGE unless pre-boiled, analytical ultracentrifugation, strong FRET from the immature green to the final red form in mammalian cells, and directed two hybrid assays in yeast using HIS3 and LacZ reporter genes. Analytical ultracentrifugation provided the clearest evidence for an obligate stoichiometry of four over the entire range of monomer concentrations assayed ($10^{-8}$ to $10^{-5}$ M), with a hint that octamer formation can occur at yet higher concentrations. In addition, the tests in live cells confirmed that aggregation occurs under typical conditions of use, including the reducing environment of the cytosol and the presence of native proteins.

While oligomerization of DsRed does not preclude its use as a reporter of gene expression, it can result in artifactual results in applications where DsRed is fused to a host protein, for example, to report on the trafficking or interactions of the host protein in a cell. For a host protein of mass M without its own aggregation tendencies, fusion with DsRed can result in the formation of a complex of at least 4(M+26 kDa). Furthermore, since many proteins in signal transduction are activated by oligomerization, fusion to DsRed and consequent association can result in constitutive signaling. For host proteins that are oligomeric, fusion to DsRed can cause clashes of stoichiometry, steric conflicts of quaternary structures, or crosslinking into massive aggregates. In fact, red cameleons, i.e., fusions of cyan fluorescent protein, calmodulin, and calmodulin-binding peptide, and DsRed, are far more prone to form visible punctae in mammalian cells than the corresponding yellow cameleons with yellow fluorescent protein in place of DsRed (Miyawaki et al., *Proc. Natl. Acad. Sci., USA* 96:2135–2140, 1999).

The results disclosed above indicate that variants of DsRed, like those of the GFPs, can be produced such that the propensity of the fluorescent protein to oligomerize is reduced or eliminated. DsRed variants can be constructed and examined, for example, using a yeast two hybrid or other similar assay to identify and isolate non-aggregating mutants. In addition, the X-ray crystallographic structure of DsRed can be examined to confirm that optimal amino acid residues are modified to produce a form of DsRed having a reduced propensity to oligomerize.

EXAMPLE 4

DsRed Variants Having Reduced Propensity to Oligomerize

This example demonstrates that mutations corresponding to those introduced into GFP variants to reduce or eliminate oligomerization also can be made in DsRed to reduce the propensity of DsRed to form tetramers.

In view of the results described in Example 1 and guided by the DsRed crystal structure, amino acid residues were identified as potentially being involved in DsRed oligomerization. One of these amino acids, isoleucine-125 (I125), was selected because, in the oligomer, the I125 residues of the subunits were close to each other in a pairwise fashion; i.e., the side chain of I125 of the A subunit was about 4 Angstroms from the side chain of I125 of the C subunit, and the I125 residues in the B and D subunits were similarly positioned. In addition, the area in which the I125 side chains reside exhibited hydrophobicity, analogous to that identified in *Aequorea* GFP variants, which was demonstrated to be involved in the inter-subunit interaction. Based on these observations, DsRed mutants containing substitutions of positively charged amino acids, Lys (K) and Arg (R), for I125 were generated.

DsRed I125K and I125R were prepared with the QuickChange Mutagenesis Kit using the DsRed cDNA (SEQ ID NO: 23; Clontech) subcloned into the expression vector pRSETB (Invitrogen) as the template for mutagenesis. The primers for mutagenesis, with the mutated codons underlined, were as follows:

TABLE 5

| Primer | Sequence | SEQ ID NO |
|---|---|---|
| I125K | 5'-TAC AAG GTG AAG TTC | |

The mutant proteins were prepared following standard methodology and analyzed with polyacrylamide gel electrophoresis as described (Baird et al., supra, 2000). For further analysis, DsRed I125R was dialyzed extensively in PBS, then diluted in PBS until the absorbance of the solution at 558 nm was 0.1. This solution was centrifuged in a Beckman XL-1 analytical ultracentrifuge in PBS at 10,000 rpm, 12,000 rpm, 14,000 rpm, and 20,000 rpm. Absorbance at 558 nm versus radius was determined and compared to a wild type tetrameric DsRed control (Baird et al., supra, 2000).

The DsRed I125K yielded a protein that became red fluorescent and was a mixture of dimer and tetramer as analyzed by non-denaturing polyacrylamide gel electrophoresis of the native protein. The same analysis of Ds Red I125R revealed that the protein was entirely dimeric. The dimeric status of DsRed I125R was confirmed by analytical ultracentrifugation; no residual tetramer was detected. These results demonstrate that the interaction between the A:C subunits and the B:D subunits can be disrupted, thereby reducing the propensity of the DsRed variant to oligomerize. No attempt was made to disrupt the A:B and C:D interfaces. These results demonstrate that the method of reducing or eliminating oligomerization of the GFP variants as described in Example 1 is generally applicable to other fluorescent proteins that have a propensity to oligomerize.

EXAMPLE 5

Preparation and Characterization of Tandem DsRed Dimers

This example demonstrates that a tandem DsRed protein can be formed by linking two DsRed monomers, and that such tandem DsRed proteins maintain emission and excitation spectra characteristic of DsRed, but do not oligomerize.

To construct tDsRed, a 3' primer, 5'-CCGGATC-CCCTTTGGTGCTGCCCTCTCCGCTGC-CAGGCTTGCCGCTGCCGCTGG TGCTGCCAAGGAA-CAGATGGTGGCGTCCCTCG-3' (SEQ ID NO: 37), was designed that overlapped the last 25 bp of DsRed (derived from the Clontech vector pDsRed-N1) and encoded for the linker sequence GSTSGSGKPGSGEGSTKG (SEQ ID NO: 38), followed by a Bam HI restriction site in frame with the Bam HI site of pRSET$_B$ (Invitrogen). It was later determined that the above primer sequence contains three mismatches in the overlap region and contained several codons that were not optimal for mammalian expression. Accordingly, a new 3' primer, 5'-CCGGATCCCCCTTGGTGCTGCCCTC-CCCGCTGCCGGGCTTCCCGCTCCCGCTGG TGCT-GCCCAGGAACAGGTGGTGGCGGCCCTCG-3' (SEQ ID NO: 39), also was used. The 5' primer, 5'-GTACGA CGATGACGATAAGGATCC-3' (SEQ ID NO: 40) also contained a Bam HI restriction site in frame with the Bam HI site of PRSET$_B$.

PCR amplification of DsRed and of DsRed-I125R with the new linker was accomplished with Taq DNA polymerase (Roche) and an annealing protocol that included 2 cycles at 40° C., 5 cycles at 43° C., 5 cycles at 45° C., and 15 cycles at 52° C. The resulting PCR product was purified by agarose gel-electrophoresis and digested with Bam HI (New England Biolabs). Bam HI and calf intestinal phosphatase (New England Biolabs) treated vector was prepared from PRSET$_B$ with DsRed or DsRed-I125R inserted in frame with the His-6 tag and between the 5' Bam HI and 3' Eco RI restriction sites.

Following ligation of the digested PCR products and vector with T4 DNA ligase (NEB), the mixture was used to transform competent *E. coli* DH5α by heat shock. Transformed colonies were grown on LB agar plates supplemented with the antibiotic ampicillin. Colonies were picked at random, and plasmid DNA was isolated through standard miniprep procedures (Qiagen). DNA sequencing was used to confirm the correct orientation of the inserted sequence.

In order to express protein, the isolated and sequenced vectors were used to transform competent *E. coli* JM109 (DE3). Single colonies grown on LB agar/ampicillin were used to inoculate 1 liter cultures of LB/ampicillin, then were grown with shaking at 225 rpm and 37° C. until the broth reached an OD$_{600}$ of 0.5–1.0. IPTG was added to a final concentration of 100 mg/l and the culture was grown for either 5 hr at 37° C. (tDsRed) or 24 hr at room temperature (RT; tDsRed-I125R). Cells were harvested by centrifugation (10 min, 5000 rpm), the pellet was resuspended in 50 mM Tris pH 7.5, and the cells were lysed by a single pass through a French press. Protein was purified by Ni-NTA (Qiagen) chromatography as described by the manufacturer and was stored in the elution buffer or was dialyzed into 50 mM Tris, pH 7.5.

With respect to the excitation and emission spectra as well as the maturation time of tDsRed and tDsRed-I125R, the proteins behaved identically to their untethered counterparts. As expected, tDsRed developed visible fluorescence within approximately 12 hr at room temperature, while tDsRed-I125R required several days before significant red color developed. The maturation of tDsRed-I125R continued for up to approximately 10 days. The excitation and emission maxima were unchanged at 558 nm and 583 nm, respectively.

The differences in the tandem dimer became apparent when the proteins were analyzed by SDS-polyacrylamide electrophoresis. Due to the high stability of the tetramer, DsRed that was not subjected to boiling migrated with an apparent molecular mass of about 110 kDa. In addition, the band on the gel, which corresponded to a DsRed tetramer, retained its red fluorescence, indicating that the rigid barrel structure of each monomer was intact. When the sample was boiled before loading, DsRed was non-fluorescent and presumably denatured, and ran as a monomer of approximately 32 kDa.

SDS-PAGE analysis confirmed the tandem structure of the expressed red fluorescent proteins, tDsRed and tDsRed-I125R. The unboiled tDsRed migrated at the same apparent molecular mass (about 110 kDa) as unboiled normal DsRed. The difference in their molecular structures only was apparent when the samples were boiled (denatured) before they were loaded onto the gel. Boiled tDsRed migrated with an apparent molecular mass of about 65 kDa, which is approximately the mass of two DsRed monomers, whereas boiled DsRed migrated at the monomer molecular mass of 32 kDa.

A similar comparison was made for DsRed-I125R and tDsRed-I125R. When they were not boiled prior to SDS-PAGE, tDsRed-I125R and DsRed-I125R both migrated as dimers with an apparent molecular mass of about 50 kDa. DsRed-I125R that was not boiled also had a large component that appeared to be denatured, though the fluorescent band for the dimer (50 kDa) was clearly visible. tDsRed-I125R also had a denatured component that migrated slower (65 kDa vs. 50 kDa) than the intact fluorescent species. However, when boiled, tDsRed-I125R migrated at approximately the same mass as two monomers (65 kDa), while DsRed-I125R migrated at the monomer molecular mass of 32 kDa.

These results demonstrate that linking two DsRed monomers to form an intramolecularly bound tandem dimer prevented formation of intermolecular oligomers, without affecting the emission or excitation spectra of the red fluorescent proteins.

EXAMPLE 6

Red Fluorescent Proteins with Improvement Efficiency of Maturation

Wild-type DsRed and Q66M DsRed Maturation

In an attempt to improve the speed and efficacy of maturation, Q66 of dsRed was converted by site-directed mutagenesis to every other naturally occurring amino acid. Only picking fluorescent colonies, it was determined that almost all single-mutations at this position (F, N, G, T, H, E, K, D, R, L, C) were deleterious, leading to loss of fluorescence, or inability to mture to a red fluorescent species. One substitution, however, Q66M, yielded a protein that had significantly improved properties.

Figure 26:
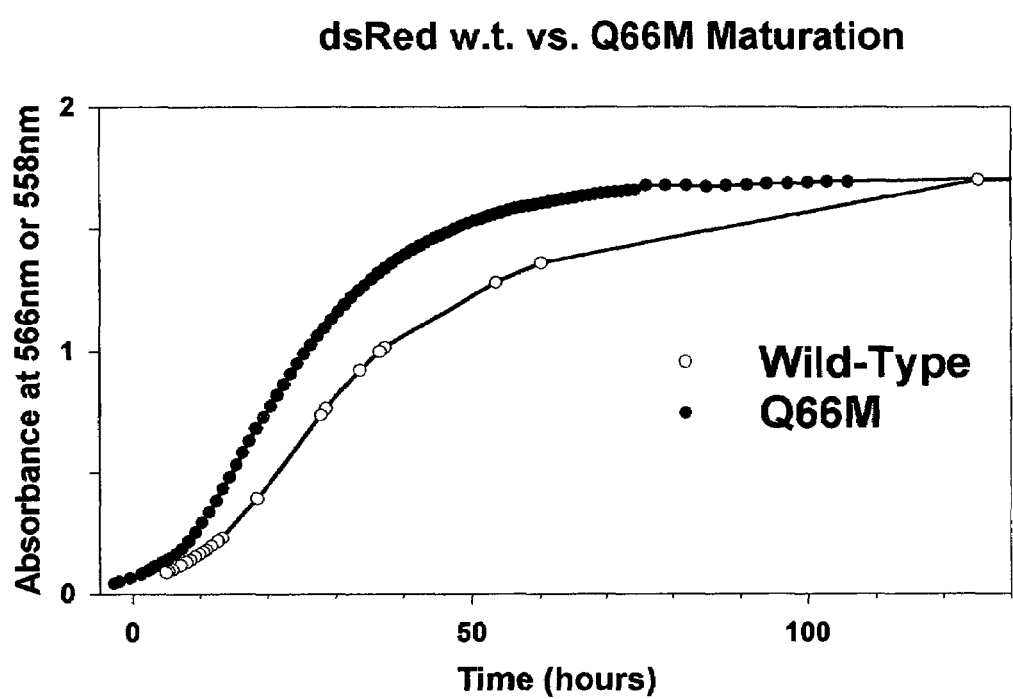
FIG. 26 illustrates the maturation of Q66M DsRed relative to the wild-type DsRed protein.

First, wild-type DsRed and Q66M DsRed were both produced in bacteria (*E. coli*) quickly purified, and allowed to mature in a cuvette sealed with parafilm. Parafilm was chosen to allow oxygen to diffuse into the protein solution, and to prevent the loss of water from the solution. The maturation was monitored by taking absorbance scans over time. FIG. 26 plots maturation as peak absorbance of the red chromophore versus time. Since the proteins were not expressed instantenously or with the exact same efficiency, the two different curves did not both start at the same value, and they reached slightly different end values. To allow comparison, both curve amplitudes were first normalized to the same final absorbance. Then, the curves were fit to a three component kinetic model, and the time base for each scan was adjusted so that the curves intersected at zero time.

Wild-type DsRed and Q66M DsRed Fluorescence

Figure 27:
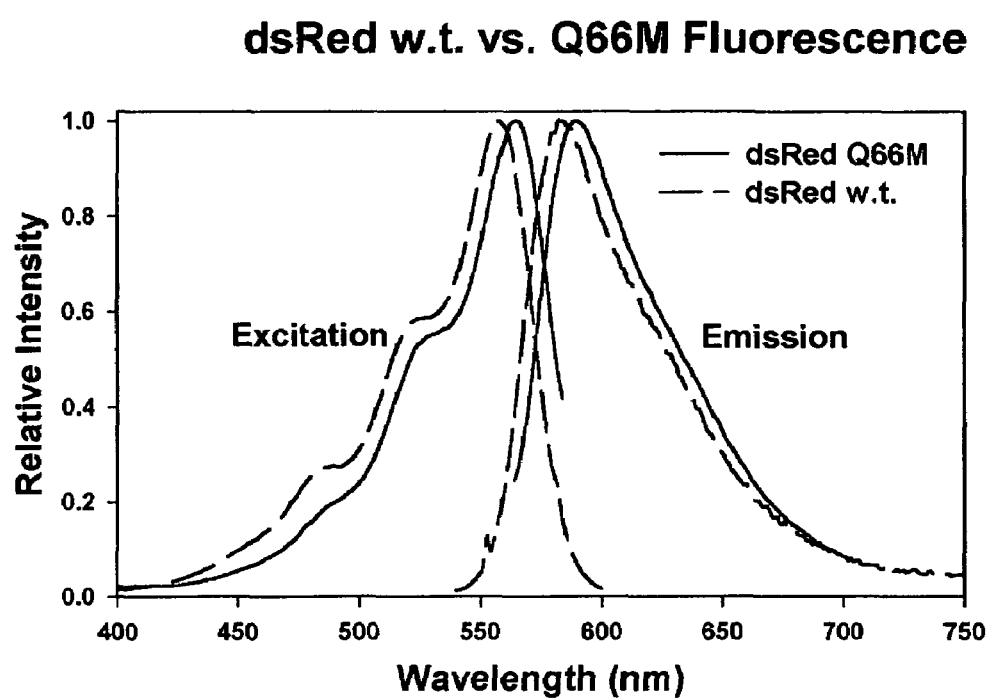
FIG. 27 shows the excitation and emission spectra of wild-type DsRed (dsRed w.t.) and Q66M DsRed (dsRED Q66M), plotting relative intensity as a function of wavelength.

Fluorescence emission and excitation spectra of wild-type DsRed and the Q66M DsRed variant were taken using 558 nm excitation or monitoring 583 nm emission for DsRed, and by using 566 nm excitation or monitoring 590 nm emission for Q66M DsRed. The results are shown in FIG. 27. Of note is the prominent red-shift of the entire Q66M DsRed fluorescence spectrum, as well as the marked depression of the excitation shoulder at 480 nm for Q66M DsRed relative to wild-type.

Q66M DsRed Completeness of Maturation

Figure 28:
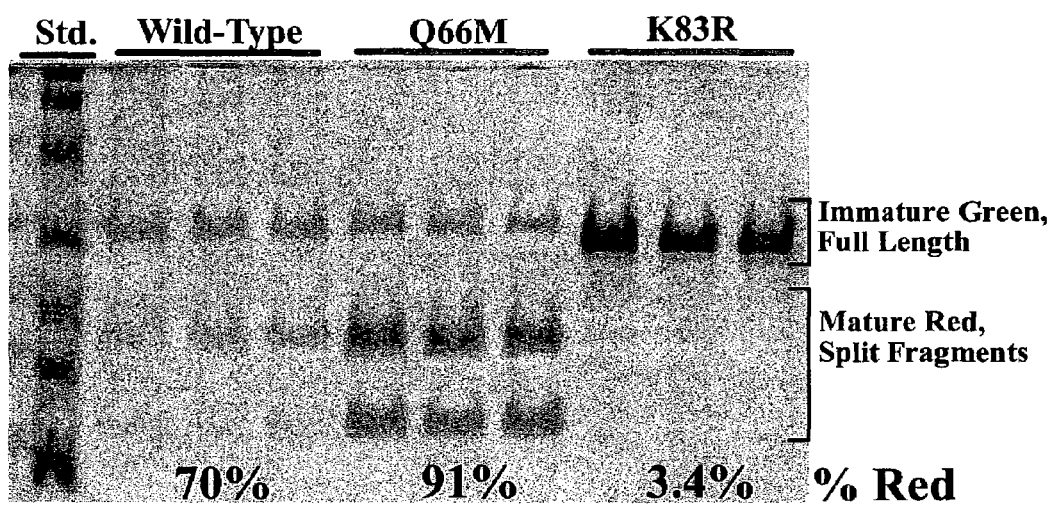
FIG. 28 shows Coomassie-stained bands on SDS-polyacrylamide gel, representative of wild-type DsRed, Q66M DsRed and K83DsRed after hydrolysis at pH 1.

Wild-type DsRed, Q66M DsRed, and another DsRed variant, K83R DsRed were subjected to brief boiling in pH 1 HCl, and then run on an SDS polyactylamide gel. Since red chromophore formation makes the protein acid labile at redicue 66, the relative amount of hydrolysis products versus full-length protein is indicative of the completeness of maturation. The gel was Coomassie stained and imaged with a flat-bed scanner, and the relative intensity of all of the bands was then quantified using the software NIH Image. After normalizaation for molecular weights (since the darkness of a Coomassie-stainer band is related to the mass of protein in the band, not the molarity), the maturation completeness was calculated by dividing the normalized intensity of the split fragments' bands by the normalized intensity of the sum of all the bands. The results are shown in FIG. 28. As expected for K83R DsRed, which contains only a trace amount of red protein, only full-length protein is visible. However, wild-type DsRed is degraded roughly 2/3 into split freagments, and Q66M DsRed is almost completely degraded into split fragments.

In conclusion, when Q66M DsRed was expressed in bacteria, the bacteria appeared to become fluorescent slightly faster than bacteria expressing wild-type DsRed. Furthermore, the Q66M DsRed protein appeared to be a deeper pink color than wild-type DsRed, which has an orange tinge. Finally, the excitation spectrum of Q66M DsRed has a significantly smaller hump at 480 nm than wild-type DsRed, suggesting that the species absorbing at 480 nm (the immature green form of the protein) was is less abundant. These data together show that Q66M DsRed has significanly improved properties over the wild-type DsRed protein.

EXAMPLE 7

Preparation of a Further Improved Variant of the Monomeric Red Fluorescent Protein, mRFP1

The engineering of the monomeric DsRed, mRFP1 (SEQ ID NO: 8), as described in the previous examples, has overcome at least three problems associated with the use of unmodified DsRed as a genetically encoded red fluorescent fusion label. Specifically, (1) mRFP1 is monomeric, (2) it matures rapidly, and (3) is not efficiently excited at wavelengths suitable for imaging of GFP. However mRFP1 is relatively dim (extinction coefficient (EC) of 44,000 $M^{-1}$ and quantum yield (QY) of 0.25) and therefore limited in certain applications. In an effort to improve the brightness of mRFP1 the strategy of directed evolution by randomizing specific residues has been continued, in the hope of finding variants with improved spectral properties.

In the first such library to improve the properties of mRFP1 the following codon substitutions were made in the mRFP1 cDNA:

N42Q to NNK=all 20 amino acids

V44A to NNK=all 20 amino acids

L46 to MTC=I or L

Q66 to NNK=all 20 amino acids

K70 to ARG=K or R

V71A to GYC=V or A

This library contains a genetic diversity of 262,144 cDNAs which encode for 64,000 different amino acid sequences. This library was transformed into E coli JM109 (DE3) and bacterial colonies were manually screened (~50,000 independent colonies) as described in the previous examples. Colonies that exhibited improved brightness or were a different color were picked and the gene was sequenced to determine the amino acid substitution. Top clones identified from this library fell into several different categories including:

Red-shifted variants:

Q66M+T147S; x588 m610, EC ~58,000 $M^{-1}$, QY ~0.25

Q66M; x588 m610, EC ~52,000 $M^{-1}$, QY ~0.25

Blue-shifted variants:

Q66T+Q213L; x574 m595, EC ~34,000 $M^1$, QY ~0.25

Q66T; x564 m581, EC 23,000 $M^{-1}$, QY 0.25

Q66S; x558 m578, dimmer than Q66T

Other interesting variants:

N42H+ Q66G; x504 m516, dim

V44M+Q66G; x504 m516, dim

Q66L; absorbance maximum at 502 nm, practically non-fluorescent

Figure 29:
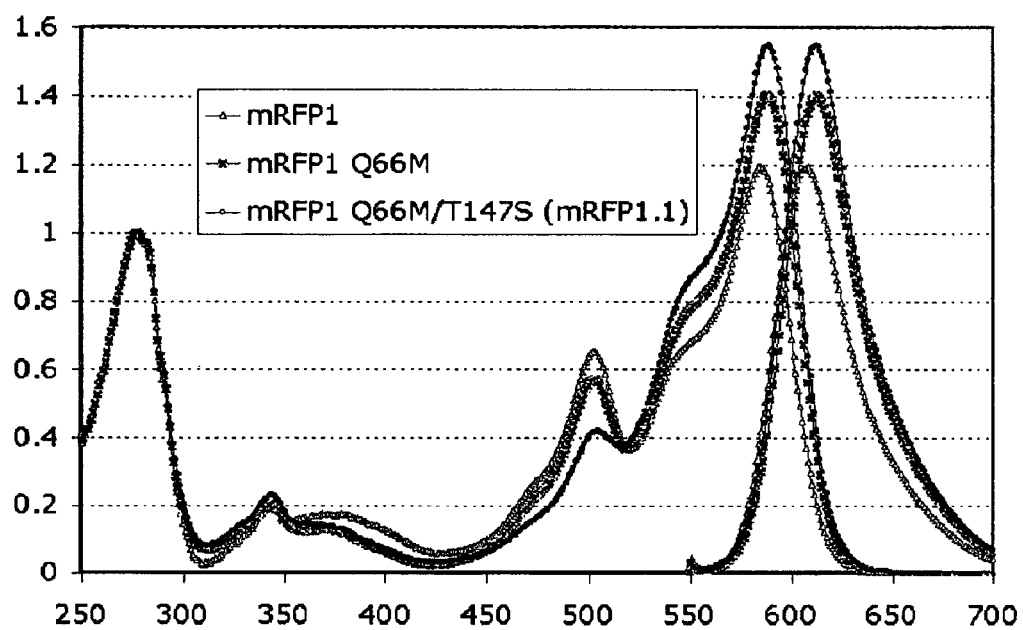
FIG. 29 shows the absorption spectrum of mRFP1, mRFP Q66M, and mRFP1.1. The absorption spectrum is normalized to the 280 nm peak which should approximate the total protein concentration. The emission spectrum (measured with excitation at 550 nm) is normalized to its respective absorption maximum for sake of representation.

The top mutant isolated from this library is mRFP1+Q66M/T147S, which has been designated mRFP 1.1. Although this variant does not improve the quantum yield relative to mRFP1, mRFP1.1 is ~30% brighter than mRFP1 due to an improved EC. This improvement is due to an apparent increase in the fraction of the protein that forms the mature red chromophore at the expense of the non-fluorescent species that absorbs at 502 nm (see FIG. 29, presenting the absorption and emission spectrum of mRFP1.1). The beneficial T147S mutant arose from an error during PCR amplification of the cDNA due to the use of Taq polymerase. The Q66M mutation has previously been shown to improve the fluorescence of the dimeric I125R variant of DsRed (Baird, G. S. (2001) Ph.D. Thesis, University of California, San Diego). The amino acid sequence of mRFP1.1 is shown in FIG. 30 (SEQ ID NO: 79), while the nucleotide sequence of mRFP1.1 is provided in FIG. 31 (SEQ ID NO: 80).

All publications, GenBank Accession Number sequence submissions, patents and published patent applications mentioned in the above specification are herein incorporated by reference in their entirety. Various modifications and variations of the described compositions and methods of the invention will be apparent to those skilled in the art without departing from the scope and spirit of the invention. Although the invention has been described in connection with various specific embodiments, it should be understood that the invention as claimed should not be unduly limited to such specific embodiments. Indeed, various modifications of the described modes for carrying out the invention which are obvious to those skilled in protein chemistry or molecular biological arts or related fields are intended to be within the scope of the following claims.

What is claimed is:

1. An isolated polynucleotide encoding a variant of a red fluorescent protein (RFP) of SEQ ID NO: 1 having a propensity to form tetrameric structures, comprising at least two amino acid alterations with respect to SEQ ID NO: 1, at least one of said at least two amino acid alterations resulting in increased efficiency of maturation compared to the efficiency of maturation of wild-type DsRed of SEQ ID NO:1, and at least one of said at least two amino acid alterations comprising an alteration at the AB interface, at the AC interface, or at the AB and AC interfaces of the wild-type DsRed amino acid sequence of SEQ ID NO: 1, comprising a substitution at an amino acid position selected from the group consisting of 125, 127, 153, 162, 164, 174, 175, 180, 192, 194, 222, 223, 224, and 225 within the wild-type DsRed amino acid sequence of SEQ ID NO: 1 and resulting in a reduced propensity to form tetramers compared to the propensity to form tetramers of wild type DsRed of SEQ ID NO:1.

2. The isolated polynucleotide of claim 1 encoding a DsRed variant of SEQ ID NO: 1, wherein said DsRed variant has an amino acid substitution at position 66 or position 147 resulting in higher fluorescence intensity at red wavelength compared to the fluorescence intensity at red wavelength of SEQ ID NO: 1.

3. The polynucleotide of claim 2 encoding a DsRed variant comprising a substitution at position 66 within SEQ ID NO: 1.

4. The polynucleotide of claim 2 wherein the amino acid substitution resulting in higher fluorescence intensity at red wavelength compared to the fluorescence intensity at red wavelength of SEQ ID NO: 1 is a Q66M substitution.

5. The polynucleotide of claim 2 encoding a DsRed variant comprising a substitution at position 147 within SEQ ID NO:1.

6. The polynucleotide of claim 2 encoding a DsRed variant comprising a T147S substitution within SEQ ID NO:1.

7. The polynucleotide of claim 4 encoding a DsRed variant comprising a T147S substitution within SEQ ID NO:1.

8. The polynucleotide of claim 7 encoding a DsRed variant comprising one or more substitutions at the AB interface, at the AC interface, or at the AB and AC interfaces of the wild-type DsRed amino acid sequence of SEQ ID NO:1, further comprising a substitution selected from the group consisting of substitutions at amino acid positions 70, 83, 117, 118, 124, 131, 150, 156, 175, 177 and 195 within the wild-type DsRed amino acid sequence of SEQ ID NO:1.

9. The polynucleotide of claim 8 encoding a DsRed variant comprising one or more substitutions at an amino acid position selected from the group consisting of 42, 44, 71, 83, 124, 150, 163, 175, 177, 179, 195, 197, 217, 2, 5, 6, 125, 127, 180, 153, 162, 164, 174, 192, 194, 222, 223, 224, 225, 21, 41, 117, and 156 within the wild-type DsRed amino acid sequence of SEQ ID NO:1.

10. The polynucleotide of claim 9 encoding a DsRed variant comprising one or more substitutions selected from the group consisting of N42Q, V44A, V71A, K83L, F124L, L150M, K163M, V175A, F177V, S179T, V195T, S197I, T217A, R2A, K5E, N6D, I125R, V127T, I180T, R153E, H162K, A164R, L174D, Y192A, Y194K, H222S, L223T, F224G, L225A, T21S, H41T, C117E, and V156A within the wild-type DsRed amino acid sequence of SEQ ID NO:1.

11. The polynucleotide of claim 1 encoding a DsRed variant comprising one or more substitutions at the AB interface, at the AC interface, or at the AB and AC interfaces of the wild-type DsRed amino acid sequence of SEQ ID NO:1, further comprising a substitution selected from the group consisting of substitutions at amino acid positions 70, 83, 117, 118, 124, 131, 150, 156, 175, 177 and 195 within the wild-type DsRed amino acid sequence of SEQ ID NO:1.

12. The polynucleotide of claim 11 encoding a DsRed variant comprising one or more substitutions at the AB interface, at the AC interface, or at the AB and AC interfaces of the wild-type DsRed amino acid sequence of SEQ ID NO:1, further comprising a substitution selected from the group consisting of substitutions at amino acid positions 2, 5, 6, 21, 41, 42, 44, 71, 163, 179, 197, and 217 within the wild-type DsRed amino acid sequence of SEQ ID NO: 1.

13. The polynucleotide of claim 1 encoding a DsRed variant comprising one or more substitutions from the group consisting of N42Q, V44A, V71A, K83L, F124L, L150M, K163M, V175A, F177V, S179T, V195T, S197I, T217A, R2A, K5E, N6D, I125R, V127T, I180T, R153E, H162K, A164R, L174D, Y192A, Y194K, H222S, L223T, F224G, L225A, T21S, H41T, C117E, and V156A within the wild-type DsRed amino acid sequence of SEQ ID NO:1.

14. The polynucleotide of claim 10 encoding a DsRed variant mRFP1.1 of SEQ ID NO:79.

15. An isolated polynucleotide encoding a DsRed variant comprising a Q66M substitution within the wild-type DsRed amino acid sequence of SEQ ID NO:1.

16. The polynucleotide of claim 15 encoding a DsRed variant that is tetrameric.

17. The polynucleotide of claim 15 encoding a DsRed variant that is monomeric.

18. A polynucleotide encoding a fusion protein, comprising a DsRed variant encoded by the polynucleotide of claim 1 operatively joined to a polypeptide of interest.

19. A polynucleotide encoding a fusion protein, comprising a DsRed variant encoded by the polynucleotide of claim 2 operatively joined to a polypeptide of interest.

20. A polynucleotide encoding a fusion protein, comprising a DsRed variant encoded by the polynucleotide of claim 4 operatively joined a polypeptide of interest.

21. A polynucleotide encoding a fusion protein, comprising a DsRed variant encoded by the polynucleotide of claim 7 operatively joined to a polypeptide of interest.

22. A polynucleotide encoding a fusion protein, comprising a DsRed variant encoded by the polynucleotide of claim 14 operatively joined to a polypeptide of interest.

23. A polynucleotide encoding a fusion protein, comprising a DsRed protein variant encoded by the polynucleotide of claim 15 operatively joined to a polypeptide of interest.

24. A polynucleotide encoding a fusion protein, comprising a DsRed variant encoded by the polynucleotide of claim 16 operatively joined to a polypeptide of interest.

25. An isolated polynucleotide encoding a tandem dimer of DsRed, comprising a first DsRed variant of SEQ ID NO:1 and a second DsRed variant of SEQ ID NO:1, at least one of which DsRed variants comprises an amino acid alteration with respect to the amino acid sequence of SEQ ID NO:1 resulting in increased efficiency of maturation compared to the efficiency of maturation of wild type DsRed of SEQ ID NO:1, wherein said first DsRed variant is operatively linked by a peptide linker to said second DsRed variant.

26. The polynucleotide of claim 25 encoding a tandem dimer of DsRed, in which at least one of said DsRed variants comprises a Q66M substitution within the wild-type DsRed sequence of SEQ ID NO:1.

27. The polynucleotide of claim 25 encoding a tandem dimer of DsRed, in which at least one of said DsRed variants comprises a T147S substitution within the wild-type DsRed sequence of SEQ ID NO:1.

28. The polynucleotide of claim 25 wherein said peptide linker is about 10 to about 25 amino acids long.

29. The polynucleotide of claim 25 wherein said peptide linker is about 12 to about 22 amino acids long.

30. The polynucleotide of claim 25 wherein said peptide linker is selected from the group consisting of GHGTGSTGSGSS (SEQ ID NO:17), RMGSTSGSTKGQL (SEQ ID NO: 18), and RMGSTSGSGKPGSGEGSTKGQL (SEQ ID NO:19).

31. A kit comprising the polynucleotide of claim 1.

32. A kit comprising a polypeptide encoded by the polynucleotide of claim 1.

33. A vector comprising the polynucleotide of claim 1.

34. A host cell comprising the vector of claim 33.

35. A vector comprising the polynucleotide of claim 3.

36. A host cell comprising the vector of claim 35.

37. A vector comprising the polynucleotide of claim 5.

38. A host cell comprising the vector of claim 37.

39. A vector comprising the polynucleotide of claim 7.

40. A host cell comprising the vector of claim 39.

41. A vector comprising the polynucleotide of claim 14.

42. A host cell comprising the vector of claim 41.

43. A vector comprising the polynucleotide of claim 15.

44. A host cell comprising the vector of claim 43.

* * * * *

SEQUENCE LISTING

<160> NUMBER OF SEQ ID NOS: 80

<210> SEQ ID NO 1
<211> LENGTH: 225
<212> TYPE: PRT
<213> ORGANISM: Discosoma sp.
<220> FEATURE:
<221> NAME/KEY: misc_feature
<222> LOCATION: (1)...(225)
<223> OTHER INFORMATION: wild-type DsRed

<400> SEQUENCE: 1

Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
210                 215                 220

Leu
225

<210> SEQ ID NO 2
<211> LENGTH: 678
<212> TYPE: DNA
<213> ORGANISM: Discosoma sp.
<220> FEATURE:
<221> NAME/KEY: misc_feature
<222> LOCATION: (1)...(678)
<223> OTHER INFORMATION: wild-type DsRed

<400> SEQUENCE: 2
atgaggtctt ccaagaatgt tatcaaggag ttcatgaggt ttaaggttcg catggaagga     60
acggtcaatg ggcacgagtt tgaaatagaa ggcgaaggag aggggaggcc atacgaaggc    120
cacaataccg taaagcttaa ggtaaccaag gggggaccct tgccatttgc ttgggatatt    180

-continued

```
ttgtcaccac aatttcagta tggaagcaag gtatatgtca agcaccctgc cgacatacca   240
gactataaaa agctgtcatt tcctgaagga tttaaatggg aaagggtcat gaactttgaa   300
gacggtggcg tcgttactgt aacccaggat tccagtttgc aggatggctg tttcatctac   360
aaggtcaagt tcattggcgt gaactttcct tccgatggac tgttatgca aaagaagaca   420 atgggctggg aagccagcac tgagcgtttg tatcctcgtg atggcgtgtt gaaggagag   480 attcataagg ctctgaagct gaaagacggt ggtcattacc tagttgaatt caaaagtatt   540
tacatggcaa agaagcctgt gcagctacca gggtactact atgttgactc caaactggat   600
ataacaagcc acaacgaaga ctatacaatc gttgagcagt atgaaagaac cgagggacgc   660
caccatctgt tcctttaa                                                 678
```

<210> SEQ ID NO 3
<211> LENGTH: 681
<212> TYPE: DNA
<213> ORGANISM: Artificial Sequence
<220> FEATURE:
<223> OTHER INFORMATION: nucleotide sequence encoding DsRed with mammalian codon usage

<400> SEQUENCE: 3

```
atggtgcgct cctccaagaa cgtcatcaag gagttcatgc gcttcaaggt gcgcatggag   60
ggcaccgtga acggccacga gttcgagatc gagggcgagg gcgagggccg ccctacgag   120 ggccacaaca ccgtgaagct gaaggtgacc aagggcggcc ccctgccctt cgcctgggac   180
atcctgtccc cccagttcca gtacggctcc aaggtgtacg tgaagcaccc cgccgacatc   240
cccgactaca agaagctgtc cttccccgag ggcttcaagt gggagcgcgt gatgaacttc   300
gaggacggcg gcgtggtgac cgtgacccag gactcctccc tgcaggacgg ctgcttcatc   360
tacaaggtga agttcatcgg cgtgaacttc ccctccgacg gccccgtaat gcagaagaag   420
accatgggct gggaggcctc caccgagcgc ctgtaccccc gcgacggcgt gctgaagggc   480
gagatccaca aggccctgaa gctgaaggac ggcggccact acctggtgga gttcaagtcc   540
atctacatgg ccaagaagcc cgtgcagctg cccggctact actacgtgga ctccaagctg   600
gacatcaccc cccacaacga ggactacacc atcgtggagc agtacgagcg caccgagggc   660
cgccaccacc tgttcctgta g                                              681
```

<210> SEQ ID NO 4
<211> LENGTH: 225
<212> TYPE: PRT
<213> ORGANISM: Artificial Sequence
<220> FEATURE:
<223> OTHER INFORMATION: DsRed polypeptide variant "T1"

<400> SEQUENCE: 4

```
Met Ala Ser Ser Glu Asp Val Ile Lys Glu Phe Met Arg Phe Lys Val
 1               5                  10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
```

```
                         85                  90                  95
Met Asn Phe Glu Asp Gly Gly Val Val Thr Val Thr Gln Asp Ser Ser
            100                 105                 110

Leu Gln Asp Gly Ser Phe Ile Tyr Lys Val Lys Phe Ile Gly Val Asn
            115                 120                 125

Phe Pro Ser Asp Gly Pro Val Met Gln Lys Lys Thr Met Gly Trp Glu
            130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
                180                 185                 190

Tyr Tyr Val Asp Ser Lys Leu Asp Ile Thr Ser His Asn Glu Asp Tyr
            195                 200                 205

Thr Ile Val Glu Gln Tyr Glu Arg Ala Glu Gly Arg His His Leu Phe
210                 215                 220

Leu
225

<210> SEQ ID NO 5
<211> LENGTH: 678
<212> TYPE: DNA
<213> ORGANISM: Artificial Sequence
<220> FEATURE:
<223> OTHER INFORMATION: Polynucleotide encoding DsRed polypeptide
      variant "T1"

<400> SEQUENCE: 5
atggcctcct ccgaggacgt catcaaggag ttcatgcgct tcaaggtgcg catggagggc      60
tccgtgaacg gccacgagtt cgagatcgag ggcgagggcg agggccgccc ctacgagggc     120
acccagaccg ccaagctgaa ggtgaccaag ggcggccccc tgcccttcgc ctgggacatc     180
ctgtcccccc agttccagta cggctccaag gtgtacgtga agcaccccgc cgacatcccc     240
gactacaaga agctgtcctt ccccgagggc ttcaagtggg agcgcgtgat gaacttcgag     300
gacggcggcg tggtgaccgt gacccaggac tcctccctgc aggacggctc cttcatctac     360
aaggtgaagt tcatcggcgt gaacttcccc tccgacggcc ccgtaatgca gaagaagact     420
atgggctggg aggcctccac cgagcgcctg taccccgcg acggcgtgct gaagggcgag     480
atccacaagg ccctgaagct gaaggacggc ggccactacc tggtggagtt caagtccatc     540
tacatggcca agaagcccgt gcagctgccc ggctactact acgtggactc caagctggac     600
atcacctccc acaacgagga ctacaccatc gtggagcagt acgagcgcgc cgagggccgc     660
caccacctgt tcctgtag                                                   678

<210> SEQ ID NO 6
<211> LENGTH: 226
<212> TYPE: PRT
<213> ORGANISM: Artificial Sequence
<220> FEATURE:
<223> OTHER INFORMATION: DsRed polypeptide variant "dimer2"

<400> SEQUENCE: 6

Met Val Ala Ser Ser Glu Asp Val Ile Lys Glu Phe Met Arg Phe Lys
1               5                   10                  15

Val Arg Met Glu Gly Ser Val Asn Gly His Glu Phe Glu Ile Glu Gly
            20                  25                  30
```

-continued

Glu Gly Glu Gly Arg Pro Tyr Glu Gly Thr Gln Thr Ala Lys Leu Lys
            35                  40                  45

Val Thr Lys Gly Gly Pro Leu Pro Phe Ala Trp Asp Ile Leu Ser Pro
 50                  55                  60

Gln Phe Gln Tyr Gly Ser Lys Ala Tyr Val Lys His Pro Ala Asp Ile
 65                  70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Val Val Thr Val Thr Gln Asp Ser
            100                 105                 110

Ser Leu Gln Asp Gly Thr Leu Ile Tyr Lys Val Lys Phe Arg Gly Thr
            115                 120                 125

Asn Phe Pro Pro Asp Gly Pro Val Met Gln Lys Lys Thr Met Gly Trp
            130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
            195                 200                 205

Tyr Thr Ile Val Glu Gln Tyr Glu Arg Ser Glu Gly Arg His His Leu
 210                 215                 220

Phe Leu
225

<210> SEQ ID NO 7
<211> LENGTH: 681
<212> TYPE: DNA
<213> ORGANISM: Artificial Sequence
<220> FEATURE:
<223> OTHER INFORMATION: Polynucleotide encoding DsRed polypeptide
      variant "dimer2"

<400> SEQUENCE: 7
atggtggcct cctccgagga cgtcatcaaa gagttcatgc gcttcaaggt gcgcatggag      60
ggctccgtga acggccacga gttcgagatc gagggcgagg gcgagggccg cccctacgag     120
ggcacccaga ccgccaagct gaaggtgacc aagggcggcc ccctgccctt cgcctgggac     180
atcctgtccc cccagttcca gtacggctcc aaggcgtacg tgaagcaccc cgccgacatc     240
cccgactaca agaagctgtc cttccccgag ggcttcaagt gggagcgcgt gatgaacttc     300
gaggacggcg gcgtggtgac cgtgacccag gactcctccc tgcaggacgg cacgctgatc     360
tacaaggtga agttccgcgg caccaacttc ccccccgacg gccccgtaat gcagaagaag     420
accatgggct gggaggcctc caccgagcgc ctgtaccccc gcgacggcgt gctgaagggc     480
gagatccacc aggccctgaa gctgaaggac ggcggccact acctggtgga gttcaagacc     540
atctacatgg ccaagaagcc cgtgcagctg cccggctact actacgtgga caccaagctg     600
gacatcacct cccacaacga ggactacacc atcgtggaac agtacgagcg ctccgagggc     660
cgccaccacc tgttcctgta g                                                681

<210> SEQ ID NO 8
<211> LENGTH: 225
<212> TYPE: PRT

<213> ORGANISM: Artificial Sequence
<220> FEATURE:
<223> OTHER INFORMATION: DsRed polypeptide variant "mRFP1"

<400> SEQUENCE: 8

```
Met Ala Ser Ser Glu Asp Val Ile Lys Glu Phe Met Arg Phe Lys Val
 1               5                  10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
 50                  55                  60

Phe Gln Tyr Gly Ser Lys Ala Tyr Val Lys His Pro Ala Asp Ile Pro
 65                  70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Glu
130                 135                 140

Ala Ser Thr Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Thr Asp Ile Lys Leu Asp Ile Thr Ser His Asn Glu Asp Tyr
        195                 200                 205

Thr Ile Val Glu Gln Tyr Glu Arg Ala Glu Gly Arg His Ser Thr Gly
210                 215                 220

Ala
225
```

<210> SEQ ID NO 9
<211> LENGTH: 678
<212> TYPE: DNA
<213> ORGANISM: Artificial Sequence
<220> FEATURE:
<223> OTHER INFORMATION: Polunucleotide encoding DsRed polypeptide
      variant "mRFP1"

<400> SEQUENCE: 9

```
atggcctcct ccgaggacgt catcaaggag ttcatgcgct tcaaggtgcg catggagggc      60
tccgtgaacg gccacgagtt cgagatcgag ggcgagggcg agggccgccc ctacgagggc     120
acccagaccg ccaagctgaa ggtgaccaag ggcggccccc tgcccttcgc ctgggacatc     180
ctgtcccctc agttccagta cggctccaag gcctacgtga agcaccccgc cgacatcccc     240
gactacttga agctgtcctt ccccgagggc ttcaagtggg agcgcgtgat gaacttcgag     300
gacggcggcg tggtgaccgt gacccaggac tcctccctgc aggacggcga gttcatctac     360
aaggtgaagc tgcgcggcac caacttcccc tccgacggcc ccgtaatgca gaagaagacc     420
atgggctggg aggcctccac cgagcggatg taccccgagg acggcgccct gaagggcgag     480
atcaagatga ggctgaagct gaaggacggc ggccactacg acgccgaggt caagaccacc     540
```

```
tacatggcca agaagcccgt gcagctgccc ggcgcctaca agaccgacat caagctggac    600
atcacctccc acaacgagga ctacaccatc gtggaacagt acgagcgcgc cgagggccgc    660
cactccaccg gcgcctaa                                                  678
```

<210> SEQ ID NO 10
<211> LENGTH: 238
<212> TYPE: PRT
<213> ORGANISM: Aequorea victoria

<400> SEQUENCE: 10

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 11
<211> LENGTH: 239
<212> TYPE: PRT
<213> ORGANISM: Artificial Sequence
<220> FEATURE:
<223> OTHER INFORMATION: Enhanced Cyan Fluorescent Protein (ECFP)

<400> SEQUENCE: 11

```
Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45
```

-continued

```
Cys Thr Thr Gly Lys Leu Pro Val Pro Trp Pro Thr Leu Val Thr Thr
 50                  55                  60

Leu Thr Trp Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235
```

<210> SEQ ID NO 12
<211> LENGTH: 239
<212> TYPE: PRT
<213> ORGANISM: Artificial Sequence
<220> FEATURE:
<223> OTHER INFORMATION: Enhanced Yellow Fluorescent Protein (EYFP)
      Variant V68L/Q69K

<400> SEQUENCE: 12

```
Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
                 20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Phe Gly Tyr Gly Leu Lys Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175
```

```
Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 13
<211> LENGTH: 239
<212> TYPE: PRT
<213> ORGANISM: Artificial Sequence
<220> FEATURE:
<223> OTHER INFORMATION: Enhanced Green Fluorescent Protein (EGFP)

<400> SEQUENCE: 13

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 14
<211> LENGTH: 239
<212> TYPE: PRT
<213> ORGANISM: Artificial Sequence
<220> FEATURE:
<223> OTHER INFORMATION: Enhanced Cyan Fluorescent Protein (ECFP)

<400> SEQUENCE: 14

Met Val Ser Lys Gly Glu Glu Leu Phe Thr Gly Val Val Pro Ile Leu
```

```
                1               5                   10                  15
            Val Glu Leu Asp Gly Asp Val Asn Gly His Arg Phe Ser Val Ser Gly
                            20                  25                  30

Glu Gly Glu Gly Asp Ala Thr Tyr Gly Lys Leu Thr Leu Lys Phe Ile
                            35                  40                  45

Cys Thr Thr Gly Lys Leu Pro Val Pro Trp Pro Thr Leu Val Thr Thr
                        50                  55                  60

Leu Thr Trp Gly Val Gln Cys Phe Ser Arg Tyr Pro Asp His Met Lys
            65                  70                  75                  80

Gln His Asp Phe Phe Lys Ser Ala Met Pro Glu Gly Tyr Val Gln Glu
                            85                  90                  95

Arg Thr Ile Phe Phe Lys Asp Asp Gly Asn Tyr Lys Thr Arg Ala Glu
                            100                 105                 110

Val Lys Phe Glu Gly Asp Thr Leu Val Asn Arg Ile Glu Leu Lys Gly
                        115                 120                 125

Ile Asp Phe Lys Glu Asp Gly Asn Ile Leu Gly His Lys Leu Glu Tyr
                        130                 135                 140

Asn Tyr Ile Ser His Asn Val Tyr Ile Thr Ala Asp Lys Gln Lys Asn
            145                 150                 155                 160

Gly Ile Lys Ala His Phe Lys Ile Arg His Asn Ile Glu Asp Gly Ser
                            165                 170                 175

Val Gln Leu Ala Asp His Tyr Gln Gln Asn Thr Pro Ile Gly Asp Gly
                            180                 185                 190

Pro Val Leu Leu Pro Asp Asn His Tyr Leu Ser Thr Gln Ser Ala Leu
                        195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
            225                 230                 235

<210> SEQ ID NO 15
<211> LENGTH: 239
<212> TYPE: PRT
<213> ORGANISM: Artificial Sequence
<220> FEATURE:
<223> OTHER INFORMATION: Enhanced Yellow Fluorescent Protein (EYFP)

<400> SEQUENCE: 15

Met Val Ser Lys Gly Glu Glu Leu Phe Thr Gly Val Val Pro Ile Leu
            1                   5                   10                  15

Val Glu Leu Asp Gly Asp Val Asn Gly His Lys Phe Ser Val Ser Gly
                            20                  25                  30

Glu Gly Glu Gly Asp Ala Thr Tyr Gly Lys Leu Thr Leu Lys Phe Ile
                            35                  40                  45

Cys Thr Thr Gly Lys Leu Pro Val Pro Trp Pro Thr Leu Val Thr Thr
                        50                  55                  60

Phe Gly Tyr Gly Val Gln Cys Phe Ala Arg Tyr Pro Asp His Met Lys
            65                  70                  75                  80

Gln His Asp Phe Phe Lys Ser Ala Met Pro Glu Gly Tyr Val Gln Glu
                            85                  90                  95

Arg Thr Ile Phe Phe Lys Asp Asp Gly Asn Tyr Lys Thr Arg Ala Glu
                            100                 105                 110

Val Lys Phe Glu Gly Asp Thr Leu Val Asn Arg Ile Glu Leu Lys Gly
                        115                 120                 125

Ile Asp Phe Lys Glu Asp Gly Asn Ile Leu Gly His Lys Leu Glu Tyr
```

```
            130                 135                 140
Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
                195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235

<210> SEQ ID NO 16
<211> LENGTH: 9
<212> TYPE: PRT
<213> ORGANISM: Artificial Sequence
<220> FEATURE:
<223> OTHER INFORMATION: Linker Polypeptide

<400> SEQUENCE: 16

Arg Met Gly Thr Gly Ser Gly Gln Leu
1               5

<210> SEQ ID NO 17
<211> LENGTH: 12
<212> TYPE: PRT
<213> ORGANISM: Artificial Sequence
<220> FEATURE:
<223> OTHER INFORMATION: Linker Polypeptide

<400> SEQUENCE: 17

Gly His Gly Thr Gly Ser Thr Gly Ser Gly Ser Ser
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Linker Polypeptide

<400> SEQUENCE: 18

Arg Met Gly Ser Thr Ser Gly Ser Thr Lys Gly Gln Leu
1               5                   10

<210> SEQ ID NO 19
<211> LENGTH: 22
<212> TYPE: PRT
<213> ORGANISM: Artificial Sequence
<220> FEATURE:
<223> OTHER INFORMATION: Linker Polypeptide

<400> SEQUENCE: 19

Arg Met Gly Ser Thr Ser Gly Ser Gly Lys Pro Gly Ser Gly Glu Gly
1               5                   10                  15

Ser Thr Lys Gly Gln Leu
            20

<210> SEQ ID NO 20
<211> LENGTH: 225
<212> TYPE: PRT
```

<213> ORGANISM: Artificial Sequence
<220> FEATURE:
<223> OTHER INFORMATION: DsRed with I125R

<400> SEQUENCE: 20

```
Met Arg Ser Ser Lys Asn Val Ile Lys Glu Phe Met Arg Phe Lys Val
 1               5                  10                  15

Arg Met Glu Gly Thr Val Asn Gly His Glu Phe Glu Ile Glu Gly Glu
             20                  25                  30

Gly Glu Gly Arg Pro Tyr Glu Gly His Asn Thr Val Lys Leu Lys Val
         35                  40                  45

Thr Lys Gly Gly Pro Leu Pro Phe Ala Trp Asp Ile Leu Ser Pro Gln
     50                  55                  60

Phe Gln Tyr Gly Ser Lys Val Tyr Val Lys His Pro Ala Asp Ile Pro
 65                  70                  75                  80

Asp Tyr Lys Lys Leu Ser Phe Pro Glu Gly Phe Lys Trp Glu Arg Val
                 85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Arg Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225
```

<210> SEQ ID NO 21
<211> LENGTH: 716
<212> TYPE: DNA
<213> ORGANISM: Aequorea victoria
<220> FEATURE:
<221> NAME/KEY: misc_feature
<222> LOCATION: (1)...(716)
<223> OTHER INFORMATION: polynucleotide encoding wild type Green
      Fluorescent Protein (GFP)

<400> SEQUENCE: 21

```
atgagtaaag gagaagaact tttcactgga gttgtcccaa ttcttgttga attagatggt      60
gatgttaatg ggcacaaatt ttctgtcagt ggagagggtg aaggtgatgc aacatacgga     120
aaacttaccc ttaaatttat ttgcactact ggaaaactac ctgttccatg gccaacactt     180
gtcactactt tctcttatgg tgttcaatgc ttttcaagat acccagatca tatgaaacag     240
catgactttt tcaagagtgc catgcccgaa ggttatgtac aggaaagaac tatattttc      300 aaagatgacg ggaactacaa gacacgtgct gaagtcaagt ttgaaggtga taccttgtt      360 aatagaatcg agttaaaagg tattgatttt aagaagatg gaaacattct tggacacaaa      420
ttggaataca actataactc acacaatgta tacatcatgg cagacaaaca aaagaatgga     480
```

```
atcaaagtta acttcaaaat tagacacaac attgaagatg aaagcgttca actagcagac      540
cattatcaac aaaatactcc aattggcgat ggccctgtcc ttttaccaga caaccattac      600
ctgtccacac aatctgccct ttcgaaagat cccaacgaaa agagagacca catggtcctt      660
cttgagtttg taacagctgc tgggattaca catggcatgg atgaactata caaata         716
```

<210> SEQ ID NO 22
<211> LENGTH: 33
<212> TYPE: PRT
<213> ORGANISM: Artificial Sequence
<220> FEATURE:
<223> OTHER INFORMATION: 6xHis Tag

<400> SEQUENCE: 22

Met Arg Gly Ser His His His His His His Gly Met Ala Ser Met Thr
 1               5                  10                  15

Gly Gly Gln Gln Met Gly Arg Asp Leu Tyr Asp Asp Asp Lys Asp
            20                  25                  30

Pro

<210> SEQ ID NO 23
<211> LENGTH: 681
<212> TYPE: DNA
<213> ORGANISM: Artificial Sequence
<220> FEATURE:
<223> OTHER INFORMATION: nucleotide sequence encoding DsRed with
      mammalian codon usage

<400> SEQUENCE: 23

```
atggtgcgct cctccaagaa cgtcatcaag gagttcatgc gcttcaaggt gcgcatggag      60
ggcaccgtga acggccacga gttcgagatc gagggcgagg gcgagggccg ccctacgag      120 ggccacaaca ccgtgaagct gaaggtgacc aagggcggcc ccctgccctt cgcctgggac      180
atcctgtccc cccagttcca gtacggctcc aaggtgtacg tgaagcaccc cgccgacatc      240
cccgactaca agaagctgtc cttccccgag ggcttcaagt gggagcgcgt gatgaacttc      300
gaggacggcg gcgtggtgac cgtgacccag gactcctccc tgcaggacgg ctgcttcatc      360
tacaaggtga agttcatcgg cgtgaacttc ccctccgacg gccccgtaat gcagaagaag      420
accatgggct gggaggcctc caccgagcgc ctgtaccccc gcgacggcgt gctgaagggc      480
gagatccaca aggccctgaa gctgaaggac ggcggccact acctggtgga gttcaagtcc      540
atctacatgg ccaagaagcc cgtgcagctg cccggctact actacgtgga ctccaagctg      600
gacatcacct cccacaacga ggactacacc atcgtggagc agtacgagcg caccgagggc      660
cgccaccacc tgttcctgta g                                               681
```

<210> SEQ ID NO 24
<211> LENGTH: 225
<212> TYPE: PRT
<213> ORGANISM: Artificial Sequence
<220> FEATURE:
<223> OTHER INFORMATION: DsRed polypeptide variant "T1" with I125R
      mutation

<400> SEQUENCE: 24

Met Ala Ser Ser Glu Asp Val Ile Lys Glu Phe Met Arg Phe Lys Val
 1               5                  10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
            35                  40                  45

Thr Lys Gly Gly Pro Leu Pro Phe Ala Trp Asp Ile Leu Ser Pro Gln
        50                  55                  60

Phe Gln Tyr Gly Ser Lys Val Tyr Val Lys His Pro Ala Asp Ile Pro
 65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Ser Phe Ile Tyr Lys Val Lys Phe Arg Gly Val Asn
        115                 120                 125

Phe Pro Ser Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Ala Glu Gly Arg His His Leu Phe
    210                 215                 220

Leu
225

<210> SEQ ID NO 25
<211> LENGTH: 42
<212> TYPE: DNA
<213> ORGANISM: Artificial Sequence
<220> FEATURE:
<223> OTHER INFORMATION: Mutagenic primer

<400> SEQUENCE: 25
cagtccaagc tgagcaaaga ccccaacgag aagcgcgatc ac        42

<210> SEQ ID NO 26
<211> LENGTH: 42
<212> TYPE: DNA
<213> ORGANISM: Artificial Sequence
<220> FEATURE:
<223> OTHER INFORMATION: Mutagenic primer

<400> SEQUENCE: 26
gtgatcgcgc ttctcgttgg ggtctttgct cagcttggac tg        42

<210> SEQ ID NO 27
<211> LENGTH: 36
<212> TYPE: DNA
<213> ORGANISM: Artificial Sequence
<220> FEATURE:
<223> OTHER INFORMATION: Mutagenic primer

<400> SEQUENCE: 27
cacatggtcc tgaaggagtt cgtgaccgcc gccggg        36

<210> SEQ ID NO 28
<211> LENGTH: 36
<212> TYPE: DNA

```
<213> ORGANISM: Artificial Sequence
<220> FEATURE:
<223> OTHER INFORMATION: Mutagenic primer

<400> SEQUENCE: 28
cccggcggcg gtcacgaact ccttcaggac catgtg                    36

<210> SEQ ID NO 29
<211> LENGTH: 36
<212> TYPE: DNA
<213> ORGANISM: Artificial Sequence
<220> FEATURE:
<223> OTHER INFORMATION: Mutagenic primer

<400> SEQUENCE: 29
cacatggtcc tgctggagcg cgtgaccgcc gccggg                    36

<210> SEQ ID NO 30
<211> LENGTH: 36
<212> TYPE: DNA
<213> ORGANISM: Artificial Sequence
<220> FEATURE:
<223> OTHER INFORMATION: Mutagenic primer

<400> SEQUENCE: 30
cccggcggcg gtcacgcgct ccagcaggac catgtg                    36

<210> SEQ ID NO 31
<211> LENGTH: 36
<212> TYPE: DNA
<213> ORGANISM: Artificial Sequence
<220> FEATURE:
<223> OTHER INFORMATION: Mutagenic primer

<400> SEQUENCE: 31
cacatcgtcc tgaaggagcg cgtgaccgcc gccggg                    36

<210> SEQ ID NO 32
<211> LENGTH: 36
<212> TYPE: DNA
<213> ORGANISM: Artificial Sequence
<220> FEATURE:
<223> OTHER INFORMATION: Mutagenic primer

<400> SEQUENCE: 32
cccggcggcg gtcacgcgct ccttcaggac catgtg                    36

<210> SEQ ID NO 33
<211> LENGTH: 33
<212> TYPE: DNA
<213> ORGANISM: Artificial Sequence
<220> FEATURE:
<223> OTHER INFORMATION: Mutagenic primer

<400> SEQUENCE: 33
tacaaggtga agttcaaggg cgtgaacttc ccc                       33

<210> SEQ ID NO 34
<211> LENGTH: 33
<212> TYPE: DNA
<213> ORGANISM: Artificial Sequence
<220> FEATURE:
<223> OTHER INFORMATION: Mutagenic primer

<400> SEQUENCE: 34
ggggaagttc acgcccttga acttcacctt gta                       33
```

<210> SEQ ID NO 35
<211> LENGTH: 33
<212> TYPE: DNA
<213> ORGANISM: Artificial Sequence
<220> FEATURE:
<223> OTHER INFORMATION: Mutagenic primer

<400> SEQUENCE: 35
tacaaggtga agttccgcgg cgtgaacttc ccc                         33

<210> SEQ ID NO 36
<211> LENGTH: 33
<212> TYPE: DNA
<213> ORGANISM: Artificial Sequence
<220> FEATURE:
<223> OTHER INFORMATION: Mutagenic primer

<400> SEQUENCE: 36
ggggaagttc acgccgcgga acttcacctt gta                         33

<210> SEQ ID NO 37
<211> LENGTH: 86
<212> TYPE: DNA
<213> ORGANISM: Artificial Sequence
<220> FEATURE:
<223> OTHER INFORMATION: Chimeric primer encoding polypeptide linker
      sequence.

<400> SEQUENCE: 37
ccggatcccc tttggtgctg ccctctccgc tgccaggctt gccgctgccg ctggtgctgc    60
caaggaacag atggtggcgt ccctcg                                 86

<210> SEQ ID NO 38
<211> LENGTH: 18
<212> TYPE: PRT
<213> ORGANISM: Artificial Sequence
<220> FEATURE:
<223> OTHER INFORMATION: Artificial Linker Sequence

<400> SEQUENCE: 38

Gly Ser Thr Ser Gly Ser Gly Lys Pro Gly Ser Gly Glu Gly Ser Thr
 1               5                  10                  15

Lys Gly

<210> SEQ ID NO 39
<211> LENGTH: 86
<212> TYPE: DNA
<213> ORGANISM: Artificial Sequence
<220> FEATURE:
<223> OTHER INFORMATION: Chimeric primer with altered codon usage.

<400> SEQUENCE: 39
ccggatcccc cttggtgctg ccctccccgc tgccgggctt cccgctcccg ctggtgctgc    60
ccaggaacag gtggtggcgg ccctcg                                 86

<210> SEQ ID NO 40
<211> LENGTH: 24
<212> TYPE: DNA
<213> ORGANISM: Artificial Sequence
<220> FEATURE:
<223> OTHER INFORMATION: Primer containing engineered restriction site.

<400> SEQUENCE: 40
gtacgacgat gacgataagg atcc                                              24

<210> SEQ ID NO 41
<211> LENGTH: 24
<212> TYPE: DNA
<213> ORGANISM: Artificial Sequence
<220> FEATURE:
<223> OTHER INFORMATION: Vector backbone primer

<400> SEQUENCE: 41
gtacgacgat gacgataagg atcc                                              24

<210> SEQ ID NO 42
<211> LENGTH: 24
<212> TYPE: DNA
<213> ORGANISM: Artificial Sequence
<220> FEATURE:
<223> OTHER INFORMATION: Vector backbone primer

<400> SEQUENCE: 42
gcagccggat caagcttcga attc                                              24

<210> SEQ ID NO 43
<211> LENGTH: 46
<212> TYPE: DNA
<213> ORGANISM: Artificial Sequence
<220> FEATURE:
<223> OTHER INFORMATION: Mutagenic Primer

<400> SEQUENCE: 43
cgcccctacg agggccacmw saccvycaag ctgaaggtga ccaagg                      46

<210> SEQ ID NO 44
<211> LENGTH: 46
<212> TYPE: DNA
<213> ORGANISM: Artificial Sequence
<220> FEATURE:
<223> OTHER INFORMATION: Mutagenic Primer

<400> SEQUENCE: 44
ccttggtcac cttcagcttg rbggtswkgt ggccctcgta ggggcg                      46

<210> SEQ ID NO 45
<211> LENGTH: 42
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 19, 20, 22
<223> OTHER INFORMATION: n = A,T,C or G

<400> SEQUENCE: 45
cagttccagt acggctccnn knyctacgtg aagcaccccg cc                          42

<210> SEQ ID NO 46
<211> LENGTH: 42
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 21, 23, 24
<223> OTHER INFORMATION: n = A,T,C or G

<400> SEQUENCE: 46

```
ggcggggtgc ttcacgtagr nmnnggagcc gtactggaac tg                      42

<210> SEQ ID NO 47
<211> LENGTH: 48
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 13, 31
<223> OTHER INFORMATION: n = A,T,C or G

<400> SEQUENCE: 47
caggacggcr vsntsatcta caaggtgaag ntscgcggca ccaacttc                48

<210> SEQ ID NO 48
<211> LENGTH: 48
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 18, 36
<223> OTHER INFORMATION: n = A,T,C or G

<400> SEQUENCE: 48
gaagttggtg ccgcgsanct tcaccttgta gatsansbyg ccgtcctg                48

<210> SEQ ID NO 49
<211> LENGTH: 46
<212> TYPE: DNA
<213> ORGANISM: Artificial Sequence
<220> FEATURE:
<223> OTHER INFORMATION: Mutagenic Primer

<400> SEQUENCE: 49
ggcgtgctga agggcgagvy ccacmwsgcc ctgaagctga aggacg                  46

<210> SEQ ID NO 50
<211> LENGTH: 46
<212> TYPE: DNA
<213> ORGANISM: Artificial Sequence
<220> FEATURE:
<223> OTHER INFORMATION: Mutagenic Primer

<400> SEQUENCE: 50
cgtccttcag cttcagggcs wkgtggrbct cgcccttcag cacgcc                  46

<210> SEQ ID NO 51
<211> LENGTH: 31
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 14
<223> OTHER INFORMATION: n = A,T,C or G

<400> SEQUENCE: 51
ggtggagttc aagnccatct acatggccaa g                                  31

<210> SEQ ID NO 52
<211> LENGTH: 31
<212> TYPE: DNA
```

<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 18
<223> OTHER INFORMATION: n = A,T,C or G

<400> SEQUENCE: 52
cttggccatg tagatggnct tgaactccac c           31

<210> SEQ ID NO 53
<211> LENGTH: 34
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 17
<223> OTHER INFORMATION: n = A,T,C or G

<400> SEQUENCE: 53
ctactactac gtggacncca agctggacat cacc           34

<210> SEQ ID NO 54
<211> LENGTH: 34
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 18
<223> OTHER INFORMATION: n = A,T,C or G

<400> SEQUENCE: 54
ggtgatgtcc agcttgkngt ccacgtagta gtag           34

<210> SEQ ID NO 55
<211> LENGTH: 34
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 17, 18
<223> OTHER INFORMATION: n = A,T,C or G

<400> SEQUENCE: 55
ctactactac gtggacnnka agctggacat cacc           34

<210> SEQ ID NO 56
<211> LENGTH: 34
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 17, 18
<223> OTHER INFORMATION: n = A,T,C or G

<400> SEQUENCE: 56
ggtgatgtcc agcttmnngt ccacgtagta gtag           34

<210> SEQ ID NO 57
<211> LENGTH: 27

```
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 13
<223> OTHER INFORMATION: n = A,T,C or G

<400> SEQUENCE: 57
cagtacgagc gcnccgaggg ccgccac                                27

<210> SEQ ID NO 58
<211> LENGTH: 27
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 15
<223> OTHER INFORMATION: n = A,T,C or G

<400> SEQUENCE: 58
gtggcggccc tcggngcgct cgtactg                                27

<210> SEQ ID NO 59
<211> LENGTH: 39
<212> TYPE: DNA
<213> ORGANISM: Artificial Sequence
<220> FEATURE:
<223> OTHER INFORMATION: Mutagenic Primer

<400> SEQUENCE: 59
aagcaccccg ccgacatccc cgactacwwk aagctgtcc                   39

<210> SEQ ID NO 60
<211> LENGTH: 42
<212> TYPE: DNA
<213> ORGANISM: Artificial Sequence
<220> FEATURE:
<223> OTHER INFORMATION: Mutagenic Primer

<400> SEQUENCE: 60
gatgtcggcg gggtgcttca cgtagrccyt ggagccgtac tg               42

<210> SEQ ID NO 61
<211> LENGTH: 39
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 7
<223> OTHER INFORMATION: n = A,T,C or G

<400> SEQUENCE: 61
gtgaagntsc gcggcaccaa cttccccycc gacggcccc                   39

<210> SEQ ID NO 62
<211> LENGTH: 48
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 18
```

<223> OTHER INFORMATION: n = A,T,C or G

<400> SEQUENCE: 62
gaagttggtg ccgcgsanct tcaccttgta gatgaasbyg ccgtcctg    48

<210> SEQ ID NO 63
<211> LENGTH: 66
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 34, 40
<223> OTHER INFORMATION: n = A,T,C or G

<400> SEQUENCE: 63
ctgtaccccc gcgacggcgt gctgaagggc gagnhcargn wsargctgaa gctgaaggac    60
ggcggc    66

<210> SEQ ID NO 64
<211> LENGTH: 66
<212> TYPE: DNA
<213> ORGANISM: Artificial Sequence
<220> FEATURE:
<223> OTHER INFORMATION: Mutagenic Primer

<400> SEQUENCE: 64
cttcagcacg ccgtcgcggg ggtacaggcg ctcggtgsts bbsbbccagc ccatrgtctt    60
cttctg    66

<210> SEQ ID NO 65
<211> LENGTH: 42
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 13
<223> OTHER INFORMATION: n = A,T,C or G

<400> SEQUENCE: 65
tccaccgagc rsntstaccc cvasgacggc rbcctgaagg gc    42

<210> SEQ ID NO 66
<211> LENGTH: 42
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 18
<223> OTHER INFORMATION: n = A,T,C or G

<400> SEQUENCE: 66
gccgtcstbg gggtasansy gctcggtgga ggsctcccag cc    42

<210> SEQ ID NO 67
<211> LENGTH: 39
<212> TYPE: DNA
<213> ORGANISM: Artificial Sequence
<220> FEATURE:
<223> OTHER INFORMATION: Mutagenic Primer

<400> SEQUENCE: 67

```
ctgaagggcg agatcargmw sargctgaag ctgaaggac          39

<210> SEQ ID NO 68
<211> LENGTH: 39
<212> TYPE: DNA
<213> ORGANISM: Artificial Sequence
<220> FEATURE:
<223> OTHER INFORMATION: Mutagenic Primer

<400> SEQUENCE: 68
gtccttcagc ttcagcytsw kcytgatctc gcccttcag          39

<210> SEQ ID NO 69
<211> LENGTH: 39
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 13, 19
<223> OTHER INFORMATION: n = A,T,C or G

<400> SEQUENCE: 69
ggccactacv vcnycgagny caagaccayc tacatggcc          39

<210> SEQ ID NO 70
<211> LENGTH: 39
<212> TYPE: DNA
<213> ORGANISM: Artificial Sequence
<220> FEATURE:
<223> OTHER INFORMATION: Mutagenic Primer
<220> FEATURE:
<221> NAME/KEY: misc_feature
<222> LOCATION: 21, 27
<223> OTHER INFORMATION: n = A,T,C or G

<400> SEQUENCE: 70
ggccatgtag rtggtcttgr nctcgrngbb gtagtggcc          39

<210> SEQ ID NO 71
<211> LENGTH: 39
<212> TYPE: DNA
<213> ORGANISM: Artificial Sequence
<220> FEATURE:
<223> OTHER INFORMATION: Mutagenic Primer

<400> SEQUENCE: 71
gtgcagctgc ccggcgccta cgccgtggac accaagctg          39

<210> SEQ ID NO 72
<211> LENGTH: 39
<212> TYPE: DNA
<213> ORGANISM: Artificial Sequence
<220> FEATURE:
<223> OTHER INFORMATION: Mutagenic Primer

<400> SEQUENCE: 72
cagcttggtg tccacggcgt aggcgccggg cagctgcac          39

<210> SEQ ID NO 73
<211> LENGTH: 36
<212> TYPE: DNA
<213> ORGANISM: Artificial Sequence
<220> FEATURE:
<223> OTHER INFORMATION: Mutagenic Primer
```

-continued

```
<400> SEQUENCE: 73
ggcrmstacr msrycgacry caagctggac atcacc                                 36

<210> SEQ ID NO 74
<211> LENGTH: 36
<212> TYPE: DNA
<213> ORGANISM: Artificial Sequence
<220> FEATURE:
<223> OTHER INFORMATION: Mutagenic Primer

<400> SEQUENCE: 74
cttgrygtcg ryskygtask ygccgggcag ctgcac                                 36

<210> SEQ ID NO 75
<211> LENGTH: 43
<212> TYPE: DNA
<213> ORGANISM: Artificial Sequence
<220> FEATURE:
<223> OTHER INFORMATION: Mutagenic Primer

<400> SEQUENCE: 75
cgaattctta skygccskyg ccgtggcggc cctcgghgcg ctc                         43

<210> SEQ ID NO 76
<211> LENGTH: 40
<212> TYPE: DNA
<213> ORGANISM: Artificial Sequence
<220> FEATURE:
<223> OTHER INFORMATION: Mutagenic Primer

<400> SEQUENCE: 76
gcttcgaatt cttacaggcc caggccgtgg cggccctcgg                             40

<210> SEQ ID NO 77
<211> LENGTH: 30
<212> TYPE: DNA
<213> ORGANISM: Artificial Sequence
<220> FEATURE:
<223> OTHER INFORMATION: Mutagenic Primer

<400> SEQUENCE: 77
aaggatccga tggcctcctc cgaggacgtc                                        30

<210> SEQ ID NO 78
<211> LENGTH: 33
<212> TYPE: DNA
<213> ORGANISM: Artificial Sequence
<220> FEATURE:
<223> OTHER INFORMATION: Mutagenic Primer

<400> SEQUENCE: 78
ttcgaattct taggcgccgg tggagtggcg gcc                                    33

<210> SEQ ID NO 79
<211> LENGTH: 225
<212> TYPE: PRT
<213> ORGANISM: Artificial Sequence
<220> FEATURE:
<223> OTHER INFORMATION: DsRed polypeptide variant "mRFP1.1"

<400> SEQUENCE: 79

Met Ala Ser Ser Glu Asp Val Ile Lys Glu Phe Met Arg Phe Lys Val
 1               5                  10                  15

Arg Met Glu Gly Ser Val Asn Gly His Glu Phe Glu Ile Glu Gly Glu
            20                  25                  30
```

```
Gly Glu Gly Arg Pro Tyr Glu Gly Thr Gln Thr Ala Lys Leu Lys Val
            35                  40                  45

Thr Lys Gly Gly Pro Leu Pro Phe Ala Trp Asp Ile Leu Ser Pro Gln
 50                  55                  60

Phe Met Tyr Gly Ser Lys Ala Tyr Val Lys His Pro Ala Asp Ile Pro
 65                  70                  75                  80

Asp Tyr Leu Lys Leu Ser Phe Pro Glu Gly Phe Lys Trp Glu Arg Val
                 85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
            115                 120                 125

Phe Pro Ser Asp Gly Pro Val Met Gln Lys Lys Thr Met Gly Trp Glu
130                 135                 140

Ala Ser Ser Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Thr Asp Ile Lys Leu Asp Ile Thr Ser His Asn Glu Asp Tyr
                195                 200                 205

Thr Ile Val Glu Gln Tyr Glu Arg Ala Glu Gly Arg His Ser Thr Gly
210                 215                 220

Ala
225

<210> SEQ ID NO 80
<211> LENGTH: 678
<212> TYPE: DNA
<213> ORGANISM: Artificial Sequence
<220> FEATURE:
<223> OTHER INFORMATION: Polynucleotide encoding DsRed polypeptide
      variant "mRFP1.1"

<400> SEQUENCE: 80
atggcctcct ccgaggacgt catcaaggag ttcatgcgct tcaaggtgcg catggagggc    60
tccgtgaacg gccacgagtt cgagatcgag ggcgagggcg agggccgccc ctacgagggc   120
acccagaccg ccaagctgaa ggtgaccaag ggcggccccc tgcccttcgc ctgggacatc   180
ctgtcccctc agttcatgta cggctccaag gcctacgtga agcacccgc cgacatcccc   240 gactacttga agctgtcctt ccccgagggc ttcaagtggg agcgcgtgat gaacttcgag   300
gacggcggcg tggtgaccgt gacccaggac tcctccctgc aggacggcga gttcatctac   360
aaggtgaagc tgcgcggcac caacttcccc tccgacggcc ccgtaatgca gaagaagacc   420
atgggctggg aggcctcctc cgagcggatg taccccgagg acggcgccct gaagggcgag   480
atcaagatga ggctgaagct gaaggacggc ggccactacg acgccgaggt caagaccacc   540
tacatggcca gaagcccgt gcagctgccc ggcgcctaca agaccgacat caagctggac   600
atcacctccc acaacgagga ctacaccatc gtggaacagt acgagcgcgc cgagggccgc   660
cactccaccg gcgcctaa                                                 678
```